(12) United States Patent
Sachdeva et al.

(10) Patent No.: US 10,166,088 B2
(45) Date of Patent: Jan. 1, 2019

(54) UNIFIED THREE DIMENSIONAL VIRTUAL CRANIOFACIAL AND DENTITION MODEL AND USES THEREOF

(71) Applicant: OraMetrix, Inc., Richardson, TX (US)

(72) Inventors: Rohit Sachdeva, Plano, TX (US); Peer Sporbert, Berlin (DE); Phillip Getto, Dallas, TX (US); Markus Kaufmann, Berlin (DE); Charles L. Abraham, Richardson, TX (US)

(73) Assignee: Ora Metrix, Inc., Richardson, TX (US)

(*) Notice: Subject to any disclaimer, the term of this patent is extended or adjusted under 35 U.S.C. 154(b) by 0 days.

(21) Appl. No.: 15/860,993

(22) Filed: Jan. 3, 2018

(65) Prior Publication Data

US 2018/0153646 A1 Jun. 7, 2018

Related U.S. Application Data

(60) Division of application No. 15/210,452, filed on Jul. 14, 2016, now Pat. No. 9,888,983, which is a division of application No. 13/107,913, filed on May 15, 2011, now Pat. No. 9,421,074, which is a
(Continued)

(51) Int. Cl.

| | |
|---|---|
| *A61C 7/00* | (2006.01) |
| *A61C 5/40* | (2017.01) |
| *G06T 17/00* | (2006.01) |
| *G06T 19/00* | (2011.01) |
| *A61B 5/055* | (2006.01) |
| *A61B 5/00* | (2006.01) |
| *A61B 6/03* | (2006.01) |
| *A61B 6/14* | (2006.01) |
| *A61B 6/00* | (2006.01) |
| *A61B 8/08* | (2006.01) |
| *A61C 7/12* | (2006.01) |
| *A61C 9/00* | (2006.01) |
| *A61C 13/08* | (2006.01) |
| *A61C 19/045* | (2006.01) |
| *G06T 19/20* | (2011.01) |
| *A61C 7/08* | (2006.01) |
| *A61C 7/14* | (2006.01) |
| *A61C 7/20* | (2006.01) |
| *A61B 1/24* | (2006.01) |
| *A61C 5/77* | (2017.01) |
| *G16H 40/20* | (2018.01) |
| *G16H 50/50* | (2018.01) |

(Continued)

(52) U.S. Cl.
CPC .............. *A61C 7/002* (2013.01); *A61B 1/24* (2013.01); *A61B 5/0013* (2013.01); *A61B 5/0077* (2013.01); *A61B 5/0088* (2013.01); *A61B 5/055* (2013.01); *A61B 5/4547* (2013.01); *A61B 6/032* (2013.01); *A61B 6/14* (2013.01); *A61B 6/4085* (2013.01); *A61B 8/0875* (2013.01); *A61C 5/40* (2017.02); *A61C 5/77* (2017.02); *A61C 7/08* (2013.01); *A61C 7/12* (2013.01); *A61C 7/14* (2013.01); *A61C 7/20* (2013.01); *A61C 9/0053* (2013.01); *A61C 13/0004* (2013.01); *A61C 13/082* (2013.01); *A61C 19/045* (2013.01); *G06F 19/00* (2013.01); *G06T 17/00* (2013.01); *G06T 19/00* (2013.01); *G06T 19/20* (2013.01); *G16H 40/20* (2018.01); *G16H 50/50* (2018.01); *G06T 2210/41* (2013.01); *G06T 2219/028* (2013.01)

(58) Field of Classification Search
CPC ....... G06T 3/0068; G06T 7/0012; G06T 7/30; G06T 7/337; G06T 7/344; G06T 19/00; G06T 19/20; G06T 2207/30036; G06T 2210/2004; A61C 7/002; A61C 9/0046; A61C 9/0053; A61B 5/4547; A61B 6/5229; A61B 6/5247
See application file for complete search history.

(56) References Cited

U.S. PATENT DOCUMENTS

| | | | |
|---|---|---|---|
| 5,431,562 A | 7/1995 | Andreiko et al. | ........... 433/24 |
| 6,632,089 B2 | 10/2003 | Rubbert et al. | .......... 433/24 |
| 6,648,640 B2 | 11/2003 | Rubbert et al. | .......... 433/24 |

(Continued)

FOREIGN PATENT DOCUMENTS

WO WO01/80761 A2 11/2001

OTHER PUBLICATIONS

Suzanne U. McCormick and Stephanie J, Drew, "Virtual Model Surgery for Efficient Planning and Surgical Performance", Journal of Oral and Maxillofacial Surgery, published Mar. 2011, vol. 69, No. 3, pp. 638-644.

*Primary Examiner* — Andrew W Johns
(74) *Attorney, Agent, or Firm* — McDonnell Boehnen Hulbert & Berghoff LLP

(57) ABSTRACT

A method and apparatus are disclosed enabling an orthodontist or a user to create an unified three dimensional virtual craniofacial and dentition model of actual, as-is static and functional anatomy of a patient, from data representing facial bone structure; upper jaw and lower jaw; facial soft tissue; teeth including crowns and roots; information of the position of the roots relative to each other; and relative to the facial bone structure of the patient; obtained by scanning as-is anatomy of craniofacial and dentition structures of the patient with a volume scanning device; and data representing three dimensional virtual models of the patient's upper and lower gingiva, obtained from scanning the patient's upper and lower gingiva either (a) with a volume scanning device, or (a) with a surface scanning device. Such craniofacial and dentition models of the patient can be used in optimally planning treatment of a patient.

8 Claims, 75 Drawing Sheets

Related U.S. Application Data continuation-in-part of application No. 12/772,208, filed on May 1, 2010, now Pat. No. 9,412,166.

(51) Int. Cl.
  *A61C 13/00* (2006.01)
  *G06F 19/00* (2018.01)

(56) References Cited

U.S. PATENT DOCUMENTS

| | | | |
|---|---|---|---|
| 7,027,642 B2 | 4/2006 | Rubbert et al. | 382/154 |
| 7,068,825 B2 | 6/2006 | Rubbert et al. | 382/128 |
| 7,080,979 B2 | 7/2006 | Rubbert et al. | 433/24 |
| 7,234,937 B2 | 6/2007 | Sachdeva et al. | 433/24 |
| 7,717,708 B2 | 5/2010 | Sachdeva et al. | 433/24 |
| 9,262,830 B2 * | 2/2016 | Bakker et al. | G06T 7/0024 |
| 9,421,074 B2 | 8/2016 | Sachdeva et al. | A61C 7/002 |
| 9,504,538 B2 | 11/2016 | Sachdeva et al. | A61C 7/002 |
| 9,561,088 B2 | 2/2017 | Sachdeva et al. | A61C 7/002 |
| 2009/0068617 A1 * | 3/2009 | Lauren | 433/213 |

* cited by examiner

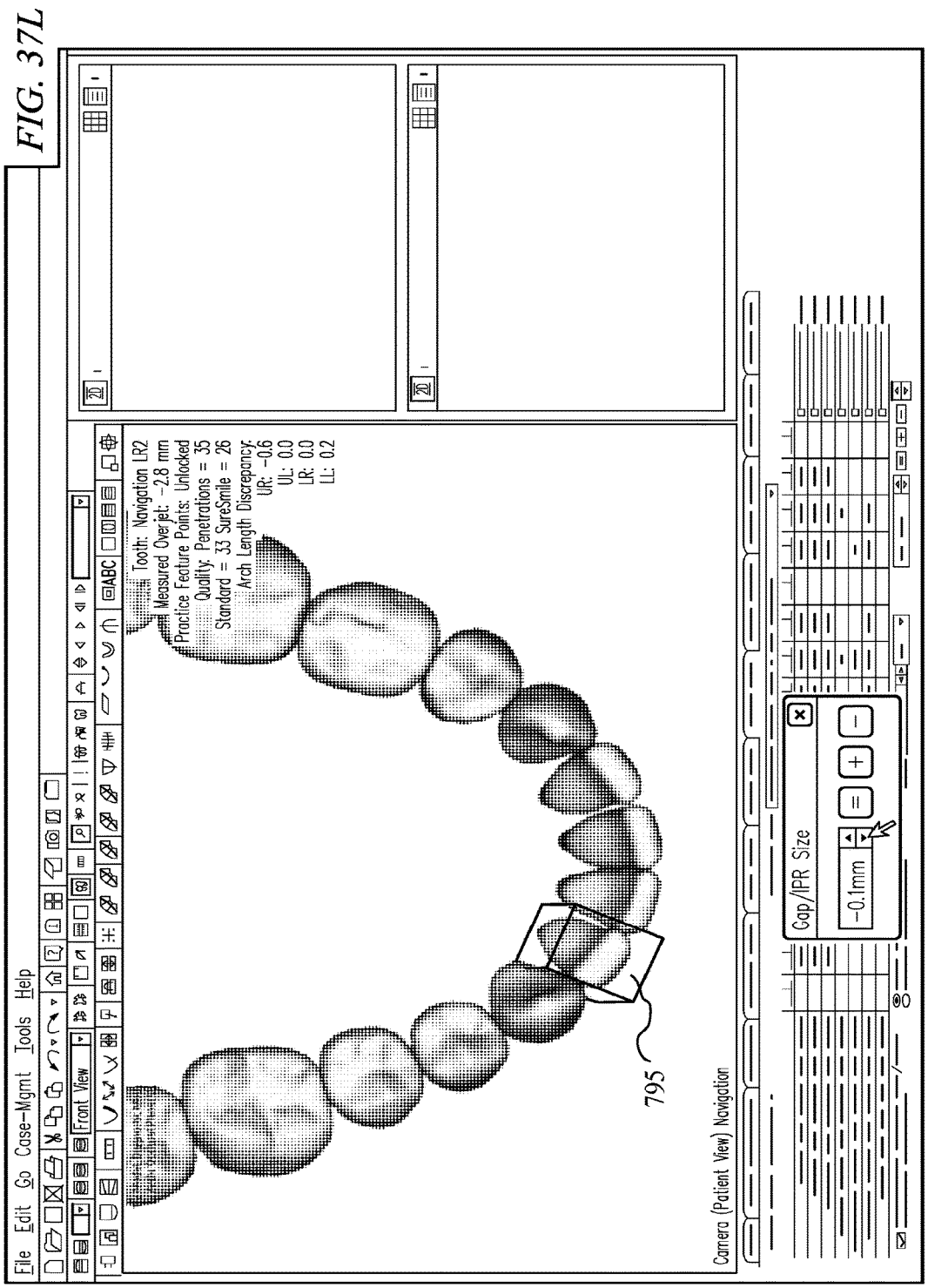

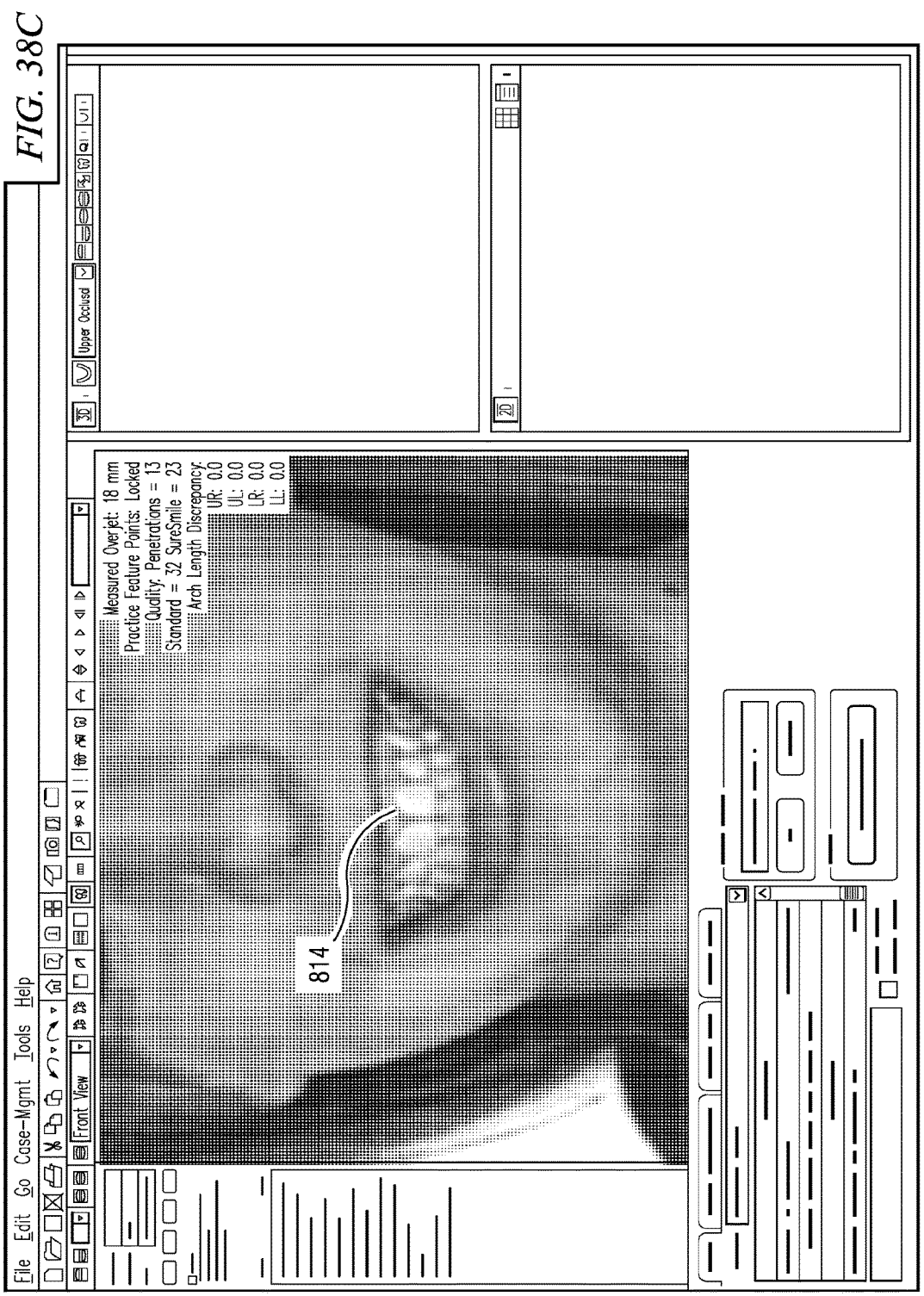

UNIFIED THREE DIMENSIONAL VIRTUAL CRANIOFACIAL AND DENTITION MODEL AND USES THEREOF

CROSS-REFERENCE TO RELATED APPLICATIONS

This application is a divisional application of application Ser. No. 15/210,452, filed Jul. 14, 2016, which is a divisional application of application Ser. No. 13/107,913, filed May 15, 2011, now issued as U.S. Pat. No. 9,421,074, which is a continuation-in-part of application Ser. No. 12/772,208, filed May 1, 2010, now issued as U.S. Pat. No. 9,412,166. This application is related to two other divisional applications of Ser. Nos. 13/107,913, 14/587,989, now issued as U.S. Pat. No. 9,504,538, and Ser. No. 14/588,100, now issued as U.S. Pat. No. 9,561,088, both filed on Dec. 31, 2014.

The subject matter of this application is related to the subject matter of the following applications. Priority to the related applications is not claimed under 35 U.S.C. § 120.

application Ser. No. 09/834,593, filed Apr. 13, 2001, now issued as U.S. Pat. No. 7,068,825;

application Ser. No. 09/835,007, filed Apr. 13, 2001, now issued as U.S. Pat. No. 7,027,642; application Ser. No. 09/834,413, filed Apr. 13, 2001, now issued as U.S. Pat. No. 7,080,979;

application Ser. No. 09/835,039, filed Apr. 13, 2001, now issued as U.S. Pat. No. 6,648,640;

application Ser. No. 09/834,593, filed Apr. 13, 2001, now issued as U.S. Pat. No. 7,068,825;

application Ser. No. 10/429,123, filed May 2, 2003, now issued as U.S. Pat. No. 7,234,937; and application Ser. No. 10/428,461, filed May 2, 2003, now issued as U.S. Pat. No. 7,717,708, which is a continuation-in-part of application Ser. No. 09/834,412, filed Apr. 13, 2001, now issued as U.S. Pat. No. 6,632,089.

The entire contents of each of the above listed patent application are incorporated by reference herein.

BACKGROUND OF THE INVENTION

A. Field of the Invention

This invention relates generally to the field of orthodontics. More particularly, the invention relates to generating a three dimensional unified virtual model of the craniofacial and dentition of a patient from volume scan and surface scan digital data; and using such model or portions thereof for planning orthodontic treatment of the patient, including surgery.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 5,431,562 to Andreiko et al. describes a computerized, appliance-driven approach to orthodontics. In this method, first certain shape information of teeth is acquired. A uniplanar target archform is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

U.S. Pat. No. 6,632,089 to Rubbert discloses an interactive, software-based treatment planning method to correct a malocclusion. The method can be performed on an orthodontic workstation in a clinic or at a remote location such as a lab or precision appliance manufacturing center. The workstation stores a virtual three-dimensional model of the dentition of a patient and patient records. The virtual model is manipulated by the user to define a target situation for the patient, including a target archform and individual tooth positions in the archform. Parameters for an orthodontic appliance, such as the location of orthodontic brackets and resulting shape of a customized orthodontic archwire, are obtained from the simulation of tooth movement to the target situation and the placement position of virtual brackets.

The key to planning optimal orthodontic, other and oral treatments is obtaining three dimensional images of actual roots of teeth of a patient. Practitioners have produced three dimensional models of roots for treatment planning from x-rays and tooth templates; however, there is no assurance that such three dimensional models of roots do really represent the anatomy of actual roots.

Suzanne U. McCornick and Stephanie J, Drew in an article published in Journal of Oral and Maxillofacial Surgery, "Virtual Model Surgery for Efficient Planning and Surgical Performance", published March 2011, Vol. 69, Number 3, pp. 638-644, disclose a modeling technique for creating a three dimensional computer based model of a patient for planning treatment for a patient. Their approach requires overlaying digital dental models obtained from a laser surface scanner over the CT/CBCT scan and align the skeletal components into natural head position using an orientation sensor. The laser scan model is obtained by scanning a stone model of the patient's teeth. Also a bite fork, with a face bow with radiographic markers, is used to obtain the information regarding the bite of the patient. While this approach shows some promising possibilities, it basically requires fusion of models produced by various devices in to a single composite model. The authors did not disclose any method for producing a three dimensional model of the patient's dentition enabling creation of three dimensional images of the patient's tooth roots.

In orthodontic treatment planning, virtual models of the dentition of a patient play a key role and are extremely important. By-and-large so far the models created from surface scan are used. These models lack in the areas or roots, bones and soft tissues. Therefore a need exists to for the virtual three dimensional models of dentition including tooth roots and surrounding anatomy which can be used in planning orthodontic treatment based upon very important information concerning three dimensional anatomy of craniofacial and dentition structures of a patient. The present invention meets this need.

SUMMARY OF THE INVENTION

Surface scans of a patient's dentition are obtained using in-vivo scanning or other types of scanning such as scanning an impression of the patient's dentition or scanning a physical model of the patient's dentition. There are number of scanning devices available to accomplish this task. Volume scans of the patient's dentition are obtained using Cone Beam Computed tomography (CBCT) or Magnetic Resonant Tomography (MM) imaging equipment. Surface scans provide data for modeling basically tooth crowns; whereas volume scans provide data for crowns as well as roots, bones, soft tissues and airways. The invention disclosed herein combines the surface scan data with the volume scan data to generate three dimensional models of a patient's dentition and surrounding anatomy including roots, bones, soft tissues, airways, etc. Both method and workstation for generating these virtual models are disclosed. The procedure can be summarized as follows:

a. obtain a intraoral surface scan or impression/plaster scan of a part or the dentition within the jaw of a patient;

b. obtain volume scan of the same patient's dentition including roots, bones, soft tissues, etc.

Note: both types of scans, i.e., surface and volume, have to represent the same patient in the same or similar condition.

c. generate a surface representation of the dentition from a the volume scan.

The surface representation can be generated by thresholding or by any other method to generate a surface from volume data. The scan data is processed to produce a mesh.

d. register the whole or a part of the surface scan into the surface extracted from volume scan data. This scan a\data is also processed to produce a mesh. The precondition for the registration is that an overlap between both types of scans, i.e., surface and volume, must exist that is sufficiently similar in both scans.

e. merging both meshes together, so that the data from the surface scan replaces the data built from the volume scan.

The workstation receives both types of scanning data and provides software tools for processing each type of data as well as for merging them together. The results are displayed on the workstation display.

The preferred embodiment of the invention discloses an apparatus comprising, in combination, a computer-readable medium storing data representing a unified three dimensional virtual craniofacial and dentition model of actual, as-is static and functional anatomy of a patient, the data comprising:

(a) data representing facial bone structure of the patient including the upper jaw and lower jaw;

(b) data representing facial soft tissue of the patient;

(c) data representing teeth including crowns and roots of the patient, the data including information of the position of the roots relative to each other and relative to the facial bone structure of the patient including the upper jaw and the lower jaw;

The data representing parts (a), (b) and (c) of unified three dimensional virtual craniofacial and dentition model of the patient are constructed solely from digital data obtained by scanning as-is anatomy of craniofacial and dentition structures of the patient with a volume scanning device;

(d) data representing three dimensional virtual models of the patient's upper and lower gingiva, wherein the data represent three dimensional virtual models of the patient's upper and lower gingiva are constructed from scanning the patient's upper and lower gingiva either (a) with a volume scanning device, or (a) with a surface scanning device; the data (d) subsequently associated with data (c); and (e) data representing function of the patient's jaw movements and smile; wherein the data representing function of the patient's jaw movements and smile are obtained through video imaging, jaw tracking, or photographs;

wherein data (a), (b), (c), (d) and (e) are represented in the medium as individual static and/or dynamic anatomical object(s) of the patient; and a viewing program for viewing data (a), (b) (c), (d) and (e) on a display of the workstation wherein data (a), (b) (c), (d) and (e) can be displayed individually or in any combination on command of a user of the workstation using the viewing program.

The preferred embodiment of the invention discloses an apparatus comprising, in combination, a computer-readable medium storing data representing a unified three dimensional virtual craniofacial and dentition model of actual, as-is static and functional anatomy of a patient, the data comprising:

(a) data representing facial bone structure of the patient including the upper jaw and lower jaw;

(b) data representing facial soft tissue of the patient;

(c) data representing teeth including crowns and roots of the patient, the data including information of the position of the roots relative to each other and relative to the facial bone structure of the patient including the upper jaw and the lower jaw;

The data representing parts (a), (b) and (c) of unified three dimensional virtual craniofacial and dentition model of the patient are constructed solely from digital data obtained by scanning as-is anatomy of craniofacial and dentition structures of the patient with a volume scanning device;

(d) data representing three dimensional virtual models of the patient's upper and lower gingiva, wherein the data represent three dimensional virtual models of the patient's upper and lower gingiva are constructed from scanning the patient's upper and lower gingiva either (a) with a volume scanning device, or (a) with a surface scanning device; the data (d) subsequently associated with data (c); and (e) data representing function of the patient's jaw movements and smile; wherein the data representing function of the patient's jaw movements and smile are obtained through video imaging, jaw tracking, or photographs;

wherein data (a), (b), (c), (d) and (e) are represented in the medium as individual static and/or dynamic anatomical object(s) of the patient; and a viewing program for viewing data (a), (b) (c), (d) and (e) on a display of the workstation wherein data (a), (b) (c), (d) and (e) can be displayed individually or in any combination on command of a user of the workstation using the viewing program.

Another preferred embodiment of the invention discloses method of planning comprehensive treatment of a patient, having a craniofacial deformity, skeletal abnormalities, soft tissue abnormalities, dental malocclusion, and dysfunction, by a practitioner, using a workstation comprising a computing platform having a graphical user interface, a processor and a computer storage medium containing digitized records pertaining to a patient, said digitized records including image data, and a set of software instructions providing graphical user interface tools for access to said digitized records, the method comprising the steps of:

(a) loading into the workstation a unified three dimensional virtual craniofacial and dentition model of said patient; wherein said unified three dimensional virtual craniofacial and dentition model comprises:

(i) facial bone structure including upper jaw and lower jaw;

(ii) facial soft tissue;

(iii) teeth including crowns and roots; wherein said roots are positioned relative to each other and relative to bones of said upper jaw and bones of said lower jaw;

(iv) upper and lower gingiva; and (v) data representing function of the patient's jaw movements and smile;

wherein said data representing function of the patient's jaw movements and smile are obtained through video imaging, jaw tracking, or photographs;

wherein the virtual model comprising elements from (i), (ii), (iii), (iv) and (v) are individual and separate data objects and viewable individually or in any combination via the graphical user interface;

(b) examining said unified three dimensional virtual craniofacial and dentition model of said patient;

(c) identifying one or more abnormalities requiring surgery for correcting said one or more abnormalities in said patient's craniofacial and/dentition;

(d) creating a post-surgery desired setup of said patient's teeth, including movements of one or more of said teeth and movements within said bone structure, for curing said malocclusion;

(e) creating a pre-surgical setup of said patient's teeth while retaining said movements of one or more of said teeth, but removing said movements within said bone structure; both from said post-surgery desired setup;

(f) creating a pre-surgical setup of said patient's teeth while retaining said movements of one or more of said teeth, but removing said movements within said bone structure;

(g) adjusting said movements of one or more of said teeth in said pre-surgical setup thereby allowing room for said surgery for removing said one or more abnormalities; and creating adjusted pre-surgical setup;

(h) designing orthodontic appliances for said patient in accordance with said adjusted pre-surgical setup;

(i) designing orthodontic appliances for said patient in accordance with said post-surgical setup;

(j) designing surgical appliances for said patient in accordance with said pre-surgical setup;

(k) designing surgical appliances for said patient in accordance with said post-surgical setup; and (l) sending data for manufacturing appliances.

Another preferred embodiment of the invention discloses a method of orthodontic treatment planning for a patient having tooth-roots abnormalities, using a workstation having a processing device, a storage device, and an user interface with a display, comprising the steps of:

(a) obtaining a three dimensional virtual model of dentition of the patient; wherein the virtual model of dentition is constructed solely from volume scanned digital images of actual craniofacial and dentition structure of the patient, and comprises the patient's teeth with three-dimensional crowns and three-dimensional roots and three-dimensional upper and lower jaw bones;

(b) identifying the tooth-roots abnormalities; and (c) planning corrective treatment steps to cure the tooth-roots abnormalities.

BRIEF DESCRIPTION OF THE DRAWINGS

Presently preferred embodiments of the invention are described below in reference to the appended drawings, wherein like reference numerals refer to like elements in the various views, and in which:

FIG. 2 shows a slice from a CBCT scan of a patient's dentition. Also shown in this figure is a photographic view of a tooth with a metal filling that distorts the CBCT data.

FIG. 3 shows a volume scan from CBCT imaging of the patient's dentition. Also shown is the same tooth with a metal filling previously shown in FIG. 2.

FIG. 4 shows a volume scan from CBCT with noise caused by slight movement of the dentition by the patient while scanning was in progress.

FIG. 5 shows a side view of both jaws of a patient with teeth, roots and jaw bones of the dentition of the patient developed from the CBCT volume scan data.

FIG. 6 shows a front view of both jaws of the patient with teeth, roots and jaw bones of the dentition of the patient developed from the CBCT volume scan data. The brackets placed on the patient's teeth are shown as well.

FIG. 7 shows surface scan data of the partial dentition of a patient. Also shown is the same tooth with a metal filling previously shown in FIG. 2.

FIG. 8 shows final modeling of teeth obtained from surface scanning of the dentition of a patient. While tooth crowns are displayed in the model, tooth roots and jaw bones are missing.

FIG. 9 shows a part of the surface scan data previously shown in FIG. 7 super imposed over the volume scan data previously shown in FIG. 3. Also shown is the same tooth with a metal filling previously shown in FIG. 2.

FIG. 10 shows another example of a part of surface scan data super imposed over volume scan data. Also shown in this figure is a photographic view of the mouth of the patient that was scanned.

FIG. 11 shows a finished model of the teeth with roots of a patient obtained by registering the mesh data from the surface scan with the mesh data from the volume scan of the dentition of a patient.

FIGS. 12 and 13 show different views of the teeth model shown in FIG. 11.

FIG. 14 shows the three-dimensional final model teeth with brackets placed on the teeth.

FIG. 15 shows front view upper and lower jaw-bones and teeth of a patient.

FIG. 16 shows right bucal view of upper and lower jaw-bones and teeth of a patient.

FIG. 17 shows front view of upper and lower jaws with a portion of the jaw-bone removed so that more of the teeth of the patient can be seen.

FIG. 18 shows front view of the upper and lower jaws and facial bone with modeled teeth, all obtained from the volume scan of the patient.

FIG. 19 shows left bucal view of the upper and lower jaws and facial bone with modeled teeth, all obtained from the volume scan of the patient.

FIG. 20 shows teeth with crowns and roots in three-dimensions modeled from the volume scan data of the patient.

FIG. 21 shows facial soft tissue model of the patient obtained from the volume scan data of the patient.

FIG. 22 shows a combination of facial tissue and teeth of the patient.

FIG. 23 shows ceph view of facial tissue plus jaw and facial bones and vertebra model of a patient with modeled teeth; all derived from the volume scan data of the patient.

FIG. 24 shows front view of the three dimensional craniofacial model of the patient, obtained by CBCT scanning showing bones and teeth. The figure also shows gingiva bite model of the patient registered with the jaws and teeth of the patient. This step is necessary because a jaw separating mouth piece is inserted in the patient's mouth while scanning with CBCT, which keeps the jaws of the patient open, and prevents scanning the bite. Therefore, the virtual model of the upper and lower gingiva of the patient, obtained from surface scanning data, as shown in FIG. 25, is registered with bones and teeth models of the patient obtained from the volume scan data.

FIG. 25 shows front view of the virtual model of the upper and lower gingiva, obtained from surface scanning data, as shown in FIG. 24 integrated with bones and teeth models of the patient derived from the volume scan data.

FIG. 26 shows front view of the three dimensional models of the brackets placed on the patients teeth obtained through volume scanning of the patient.

FIG. 27 shows another view of the layout of the bracket models presented in FIG. 26.

FIG. 28 shows the brackets in the form of line drawings.

FIG. 29 shows models of the specific brackets, derived from the bracket impressions, mounted on the models of the crowns of the patient.

FIG. 30 shows models of the specific brackets, derived from the bracket impressions, mounted on the models of the teeth of the patient, along with the models of the jaw and other facial bones of the patient.

FIG. 31 shows model of the patient's bite obtained through surface scanning.

FIG. 32 shows integration of the bite scan model with the jaw bones and teeth of the patient. The bite is shown in the closed position in this figure.

FIG. 33 shows bite in an open position along with the facial and jaw bone structures of the patient in the right bucal view.

FIG. 34 also shows from the right bucal view bite in a further open position compared to the bite in FIG. 33, along with the facial and jaw bone structures of the patient. Form the volume scan data, it is possible to identify the portion of the jaw bone which functions like a hinge for moving the jaw; and thereby simulate the movement of the jaws.

FIG. 35 shows a snap shot of the bite simulation from the left bucal view.

FIG. 36A shows image of patient's tooth crowns.

FIG. 36T shows the upper occlusal surfaces of the teeth and their roots below, three segments to plan for 3 piece maxillary surgery have been selected. The upper right segment has been expanded and its displacement value shown. Any number of segments can be chosen, and the site of the ostetotmy can be defined if the roots fall in to the ostetotmy site their movement can be planned presurgically away from the resection site to avoid damage. The segments can be moved in all three planes of space.

FIG. 37A shows both a 2-D view and a 3-D view of the mal-formed tooth, and the space on either side of the mal-formed tooth. This space can be closed orthodontically or the shape or the shape and form of the tooth can be restored.

FIG. 37L shows the selection of automatic veneer build up to resolve the crowding completely and to provide better shape and form. 3-D simulation planning has allowed the optimal planning of care from both restorative and orthodontic perspectives with minimal tooth movement and destruction of tooth.

FIG. 37N shows fractured incisal edge restored in normal shape and form.

FIG. 38C shows volumetric 3-D image of teeth and gingival tissue in relation to the patient's face in order to assess and plan for aesthetics.

DETAILED DESCRIPTION OF PREFERRED EMBODIMENT

Figure 1:
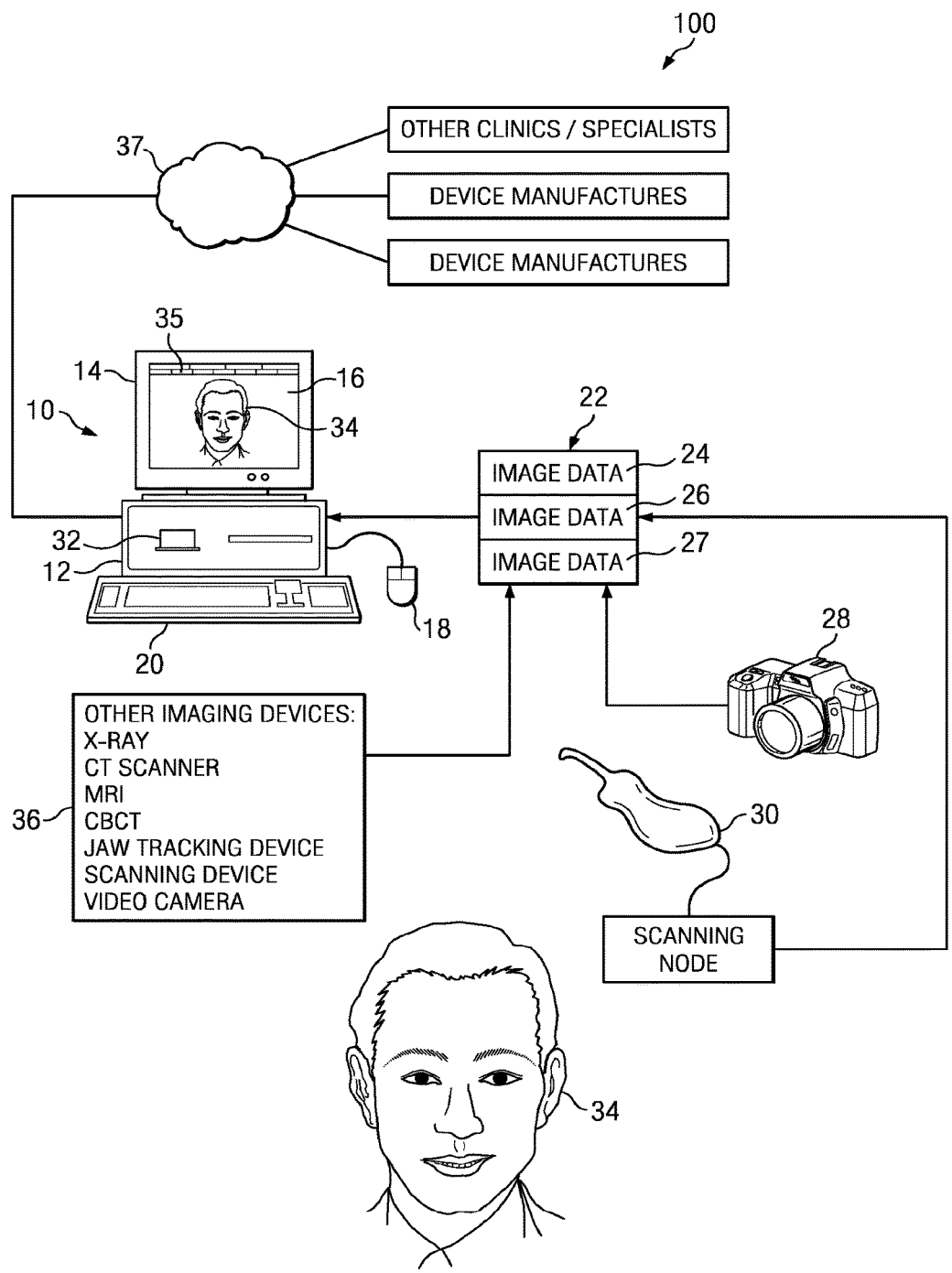
FIG. 1 is block diagram of a system for creating a three-dimensional virtual patient model and for diagnosis and planning treatment of the patient.

Before describing the features of this invention in detail, an overview of a unified workstation will be set forth initially. The workstation provides software features that create two dimensional and/or three-dimensional virtual patient model on a computer, which can be used for purposes of communication, diagnosis, treatment planning and design of customized appliances in accordance with a presently preferred embodiment.

The essence of the invention disclosed herein is the ability to capture images from various sources that provide volumetric images, surface images that are 3-D or 2-D in nature, and may be static or dynamic, such as from CBCT, CAT, MM, fMRT, ultrasound device, cameras that provide still photos, white light and laser based surface scanners, video cameras providing video images, tracking devices and digital camera. Images from these sources are combined as needed to create a unified simulation model of the craniofacial and dental facial complex, to facilitate diagnosis, communication, planning treatment and design of appliances for treating craniofacial and dento facial problems. With these images a composite structure of the face can be constructed with dynamic or static behavioral properties. One can also track function or jaw movement and simulate the functional movements, e.g., smile movement of the lower jaw etc.

The global positioning of the entire face with respect to its surroundings can be set by the user for planning purposes. In addition, the relative position of each of the structural elements, such as the upper jaw and its teeth when captured independently can be oriented with respect to any other structure such as the soft tissue face by using specific anatomical land marks or user defined reference planes, either in 2-D or 3-D space. Furthermore, the relationship of the lower jaw and its accompanying teeth can be registered with respect to the upper jaw using a combination of registration techniques. For instance, the bite registration can be recorded by taking an intraoral surface scan of the teeth together and using it as a template to register the relationship of the upper jaw and the lower jaw from a CBCT volumetric scan.

Most importantly from volumetric data, one can extract three dimensional structural data which may include crowns and roots of teeth, bone, soft tissue, e.g., gingiva and facial soft tissue and appliances attached to any of these structures, such as orthodontic brackets, implants, etc. Each of these structural elements can be independently manipulated in three dimensional space to construct a treatment plan, and design the appropriate device for correction of a problem. Furthermore, the interdependencies of the treatment between these various structural components can be modeled to design a holistic treatment plan. Specific relationships between the various structural components can be defined by choosing an appropriate reference plane and capturing the spatial relationships between specific structures. The treatment design may include repositioning, restoring, replacing of any of the structural elements in 2-D or 3-D space. Also function can be simulated or modeled based upon captured data to achieve the desired goals, e.g., the teeth with their roots can be appropriately positioned in the bone to withstand the stresses of jaw movement or the position of the jaw joint i.e. the condyle is in harmony with the position of the teeth to prevent any source of dysfunction or breakdown of the structural elements. Mechanical analysis, such as finite element method, may also be used to better understand the nature of stresses and strains imposed on the structural elements to design better treatment. All changes may be measured with respect to defined planes of reference to provide numerical output to design a variety of customized treatment devices, such as orthodontic brackets, orthodontic archwires, surgical bite splints, surgical fixation plates, implants, condylar prosthesis, bone screws, periodontal stents, mouth guards, bite plates, removable orthodontic appliances, crowns, bridges, dentures, partial dentures, obturataors, temporary anchorage devices from either natural or synthetic substances using printing devices, such as SLA or milling or robotic manufacturing. Any type of dental, orthodontic, restorative, prosthodontic or surgical device which may be tissue borne, dental borne, osseous borne, can be designed in combination, or singularly in serial or in parallel, e.g., indirect bonding trays that allow bonding of brackets, and are also designed to guide implant insertion. Furthermore, if the patient requires surgery, splints, fixation plates, boney screws may all be designed and manufactured simultaneously. The numerical output of the treatment plan can be used to drive navigational systems for performing any procedure. Simulations can be used to train and build skills or examine proficiency. The numerical output of the treatment design can be used to drive robots to perform surgical procedures. Furthermore this output can be used to create a solid model representation of the treatment plan using printing or milling techniques.

Template data or normative data stored in memory can be used to plan any of the structural changes or design of the devices. In addition, reference data from the non-affected structural elements may be used as templates to provide design parameters to plan and correct the affected side.

One can also replace or remove any of the structures to achieve the desired goal, e.g., extraction of teeth, root amputation, sinus lift, veneers, inter-proximal reduction, etc. The codependency of movement of one object and its effect on another can also be simulated for all three tissue types e.g. when the tooth moves how does it affect the gum soft tissue when the tooth moves where does the root move in reference to the bone or how does the bone change how does the face change when the bones move. All types of planning can be executed by different modalities or professionals in an interactive manner asynchronously or synchronously.

In summary, the invention disclosed herein provides the ability to plan crowns with roots thereby optimizing the planning by changing the root position so that the crown planned is designed such that axial forces are transmitted to the roots to add to the stability of the crown minimizing aberrant forces that can lead to root fracture, crown fracture, and breakdown of the periodontium or bone. Similarly for surgical patients one can plan root positions so that the surgeon can cut between the roots and prevent damage besides planning the movement of the bones. Similarly for implants one can move the roots in a desirable location so that the implant when inserted doesn't damage the roots. The user can also size the implants correctly so that they don't encroach on root space. All this planning would be impossible if the roots were not made separate objects that could move. Finally one can move the roots preferentially to create bone. As one extrudes a root one can create bone. Similarly one can change the gum tissue architecture by moving roots and for orthodontic movement one can avoid moving roots where there is no bone or selectively move teeth to prevent root collision or move roots away from areas where there is lack of bone into where there is as one plans to move them towards their final destination. Again not only can one plan tooth movement but bone movement and soft tissue gum and face as well to achieve the goals. One can alter the spatial position of all the objects which are extracted, change their shape form and volume to restore and or reconstruct. One can sculpt or remove selectively any region gum soft issue bone dentition. Although one can use a fusion technique, the preferred embodiment is to extract the data from the CBCT for bone and dentition with roots at a minimum. One can take partial intramural scans where distortion is expected, e.g., large metal crowns or fillings or one can scan an impression in those areas or plaster limited to the region of interest.

The images of the roots can be taken with CBCT and affixed to crowns taken by scanning intramurally impressions or models. The preferred process does not require fusing a model of the dentition into the crank facial structure. All needed information can be captured in one shot and extract individual features. The invention disclosed herein captures the dental and osseous and soft tissue as one and segregate them in to individual components for planning treatment. The optimization of the treatment plan can be achieved by using different approaches, e. g., correcting crowding by minimizing tooth movement and planning veneers or minimizing tooth preparation for veneer construction by positioning the teeth appropriately. This can be said for any structure and the decision can be driven by the patients need, time constraints, cost risk benefit, skill of operator, etc.

Many of the details and computer user interface tools which a practitioner may use in adjusting tooth position, designing appliance shape and location, managing space between teeth, and arriving at a finish tooth position using interaction with a computer storing and displaying a virtual model of teeth are set forth in the prior application Ser. No. 09/834,412 filed Apr. 13, 2001, and in published OraMetrix patent application WO 01/80761, the contents of which are incorporated by reference herein. Other suites of tools and functions are possible and within the scope of the invention. Such details will therefore be omitted from the present discussion.

General Description

A unified workstation environment and computer system for diagnosis, treatment planning and delivery of therapeutics, especially adapted for treatment of craniofacial structures, is described below. In one possible example, the system is particularly useful in diagnosis and planning treatment of an orthodontic patient. Persons skilled in the art will understand that the invention, in its broader aspects, is applicable to other craniofacial disorders or conditions requiring surgery, prosthodontic treatment, restorative treatment, etc.

A presently preferred embodiment is depicted in FIG. 1. The overall system 100 includes a general-purpose computer system 10 having a processor (CPU 12) and a user interface 14, including screen display 16, mouse 18 and keyboard 20. The system is useful for planning treatment for a patient 34.

The system 100 includes a computer storage medium or memory 22 accessible to the general-purpose computer system 10. The memory 22, such as a hard disk memory or attached peripheral devices, stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-rays, MRI or ultrasound images, CT scanner, CBCT scanner, jaw tracking device, scanning device, video camera, etc., from other imaging devices 36. The other imaging devices need not be located at the location or site of the workstation system 100. Rather, the imaging of the patient 34 with one or other imaging devices 36 could be performed in a remotely located clinic or hospital, in which case the image data is obtained by the workstation 100 over the Internet 37 or some other communications medium, and stored in the memory 22.

The system 100 further includes a set of computer instructions stored on a machine-readable storage medium. The instructions may be stored in the memory 22 accessible to the general-purpose computer system 10. The machine-readable medium storing the instructions may alternatively be a hard disk memory 32 for the computer system 10, external memory devices, or may be resident on a file server on a network connected to the computer system, the details of which are not important. The set of instructions, described in more detail below, comprise instructions for causing the general computer system 10 to perform several functions related to the generation and use of the virtual patient model in diagnostics, therapeutics and treatment planning.

These functions include a function of automatically, and/or with the aid of operator interaction via the user interface 14, superimposing the first set 24 of digital data and the second set 26 of digital data so as to provide a composite, combined digital representation of the craniofacial anatomical structures in a common coordinate system. This composite, combined digital representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data could be intra-oral 3D scan data obtained from the hand-held scanner 30, CT scan data, X-Ray data, MRI, etc. In the example of FIG. 1, the hand-held scanner 30 acquires a series of images containing 3D information and this information is used to generate a 3D model in the scanning node 31, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model. These data sets are superimposed with each other, with appropriate scaling as necessary to place them in registry with each other and at the same scale. The resulting representation can be stored as a 3D point cloud representing not only the surface on the patient but also interior structures, such as tooth roots, bone, and other structures. In one possible embodiment, the hand-held in-vivo scanning device is used which also incorporates a color CCD camera to capture either individual images or video.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is cable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient. The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in an dynamic format (i.e., during movement of anatomical structures relative to each other, such as chewing, occlusion, growth, etc.). To facilitate such modeling and simulations, teeth may be modeled as independent, individually moveable 3 dimensional virtual objects, using the techniques described in the above-referenced OraMetrix published PCT application, WO 01/80761.

The workstation environment provided by this invention provides a powerful system and for purposes of diagnosis, treatment planning and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial, pre-treatment position to provide the desired result. This leads directly to a patient treatment plan.

These simulation tools, in a preferred embodiment, comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays useful in this invention are described in the patent application of Rudger Rubbert et al., Ser. No. 09/835,039 filed Apr. 13, 2001, the contents of which are incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized flat planar archwire, and customized bracket placement jigs, as described in the above-referenced Andreiko et al. patents. Alternatively, the initial and final tooth positions can be used to derive data sets representing intermediate tooth positions, which are used to fabricate transparent aligning shells for moving teeth to the final position, as described in the above-referenced Chisti et al. patents. The data can also be used to place brackets and design a customized archwire as described in the previously cited application Ser. No. 09/835,039. To facilitate sharing of the virtual patient model among specialists and device manufacturers, the system 100 includes software routines and appropriate hardware devices for transmitting the virtual patient model or some subset thereof over a computer network. The system's software instructions are preferably integrated with a patient management program having a scheduling feature for scheduling appointments for the patient. The patient management program provides a flexible scheduling of patient appointments based on progress of treatment of the craniofacial anatomical structures. The progress of treatment can be quantified. The progress of treatment can be monitored by periodically obtaining updated three-dimensional information regarding the progress of treatment of the craniofacial features of the patient, such as by obtaining updated scans of the patient and comparison of the resulting 3D model with the original 3D model of the patient prior to initiation of treatment.

Thus, it is contemplated that system described herein provides a set of tools and data acquisition and processing subsystems that together provides a flexible, open platform or portal to a variety of possible therapies and treatment modalities, depending on the preference of the patient and the practitioner. For example, a practitioner viewing the model and using the treatment planning tools may determine that a patient may benefit from a combination of customized orthodontic brackets and wires and removable aligning devices. Data from the virtual patient models is provided to diverse manufacturers for coordinated preparation of customized appliances. Moreover, the virtual patient model and powerful tools described herein provide a means by which the complete picture of the patient can be shared with other specialists (e.g., dentists, maxilla-facial or oral surgeons, cosmetic surgeons, other orthodontists) greatly enhancing the ability of diverse specialists to coordinate and apply a diverse range of treatments to achieve a desired outcome for the patient. In particular, the overlay or superposition of a variety of image information, including 2D X-Ray, 3D teeth image data, photographic data, CT scan data, and other data, and the ability to toggle back and forth between these views and simulate changes in position or shape of craniofacial structures, and the ability to share this virtual patient model across existing computer networks to other specialists and device manufacturers, allows the entire treatment of the patient to be simulated and modeled in a computer. Furthermore, the expected results can be displayed beforehand to the patient and changes made depending on the patient input.

With the above general description in mind, additional details of presently preferred components and aspects of the inventive system and the software modules providing the functions referenced above will be described next.

Integrated 3-D Modeling of Patient's Dentition from Surface Scanning and CBCT Imaging The invention disclosed herein enables orthodontists to accurately measure complex three dimensional anatomy during diagnosis and treatment planning of orthodontic patients. The invention enables orthodontists or users to capture 3D scans with intraoral scanners as well as cone beam computed tomography (CBCT) that can capture highly precise digital scans. The resulting digital images are downloaded to a computer, and combined in order to create comprehensive 3-D models of the patient's dentition, roots, bones and soft tissues thereby creating 3-D digital teeth model and surrounding anatomy of pre-treatment mouth. The invention provides substantial improvement over the traditional two dimensional imaging modalities such as x-rays, photographs, cephalometric tracing for diagnosis and treatment planning.

In a preferred embodiment of the invention, scanning is done in-vivo using a white light scanner, and is non-invasive. Scanner is reference independent, so the object being scanned can move while being scanned and the scanned data will still be useful. Scanning can be performed again to get the modeling information that might be missing. In order to perform bite registration, it does not require wax bite. This type of scanning does not allow reconstruction of data. Pano and Ceph should be taken separately and imported into the image management software.

When needed, a partial scan can be taken. The scanning captures only the coronal portion of the tooth in 3-D. However, gingiva is viewable with this type of scanning. Scanning can be performed with orthodontic brackets, made of either plastic or metal or a combination, placed on the patient's teeth; as well as with one or more teeth crowns having metal fillings. Tooth separators are not required in order to perform scanning. Excessive voids in scan data can affect tooth modeling. This type of scanning can be used for creating 3D models of teeth from raw scan data for diagnostic, therapeutic and final outcome evaluation.

In contrast, CBCT imaging is invasive, and requires tooth separators. In order to perform bite registration, a wax bite or bite block is required. Multiple slices taken by CBCT can be reconstructed to look like 3-D images of teeth, jaws and even soft tissue; and Pano and Ceph can also be reconstructed from the data captured by CBCT. Partial scan is not possible with CBCT. CBCT images capture crown, root, surrounding bone and soft tissues which can be put together in three dimensions. Although gingiva can be viewed with CBCT images, the root anatomy obtained is preferred. There are several limitations while using CBCT for imaging the patient's dentition, such as for example, (a) the brackets are limited generally to plastic brackets since metal brackets cause image distortion, (b) metal crown fillings by-and-large cannot be handled since fillings larger than 4 mm creates noise causing image distortion and (c) a patient cannot move during the CBCT imaging procedure since any motion during imaging causes blurring of image making it unusable. Additionally, wax bite or bite blocks used as separators to prevent opposing teeth from coming in contact during the CBCT imaging procedure. Excessive 'noise' caused by large metal objects in patient's mouth causes distortion of images adversely affecting tooth modeling.

CBCT imaging can also be used for creating 3D models of teeth from raw image data for diagnostic, therapeutic and final outcome evaluation. Furthermore, X-rays can be reconstructed from CBCT images.

Surface scanning as well as volume scanning by CBCT or MM imaging each has some short-comings. However, they can be used in a complimentary manner to produce 3-D digital models of patient's dentition including teeth with roots, bones and soft tissues such as gingival, and with excellent quality.

FIGS. 2-6 show data from the CBCT volume scan of a patient at different stages of processing.

Figure 2:
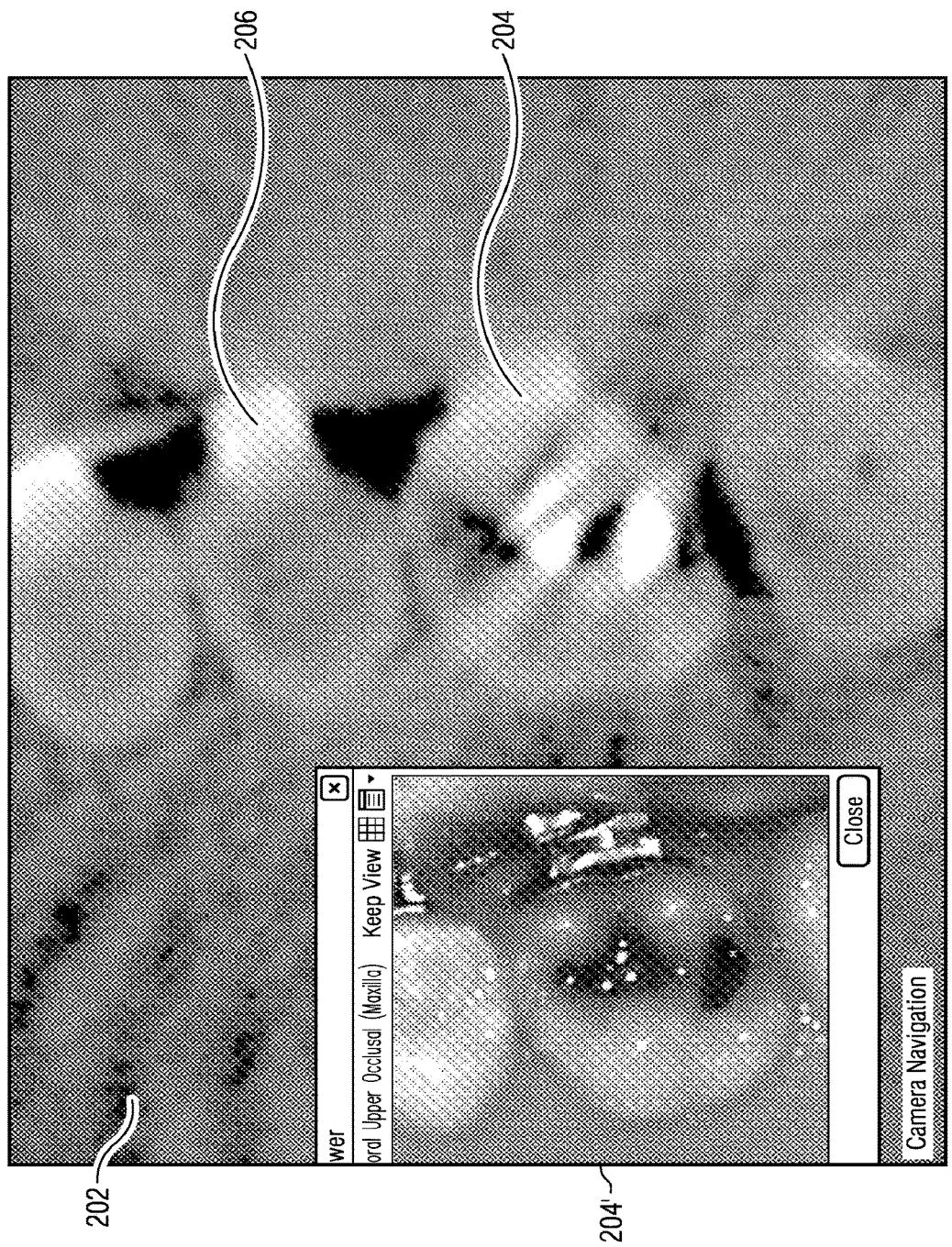
FIGS. 2-6 show data from the CBCT volume scan of a patient at different stages of processing.

FIG. 2 shows a slice 302 from a CBCT scan of a patient's dentition. Also shown in this figure is a photographic view of a tooth 204' with a metal filling that distorts the CBCT data. CBCT image 204 of tooth 204' is damaged in slice 302 due to the metal filling. Other teeth, for example image 206 of a tooth without metal filling comes out undamaged.

Figure 3:
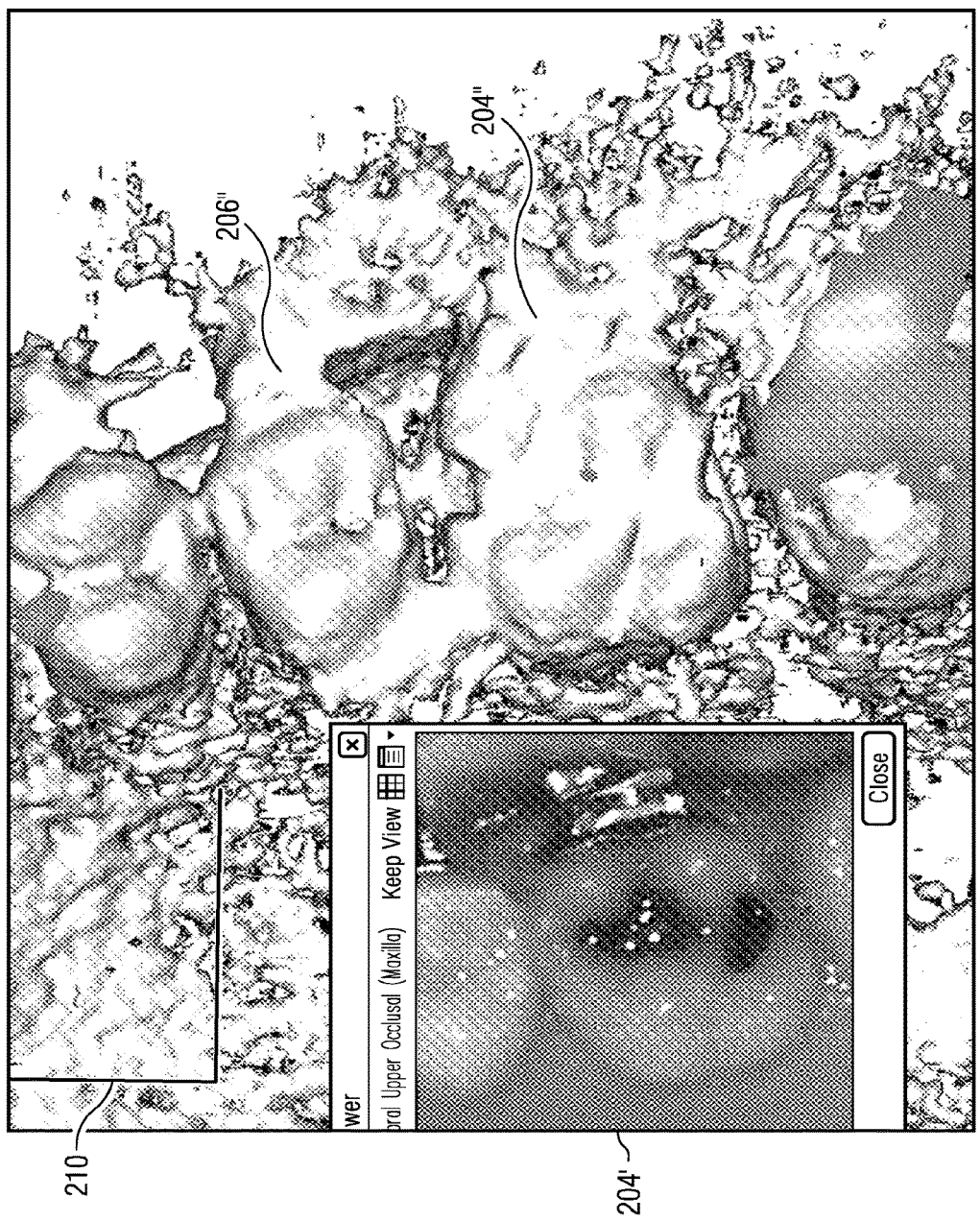

FIG. 3 shows a volume scan 210 from CBCT imaging of the patient's dentition. Also shown is the same tooth 204' with a metal filling previously shown in FIG. 2. The image 204" of the tooth 204' with the metal filling comes out damaged; whereas, image 206" of a tooth without metal filling is acceptable.

Figure 4:
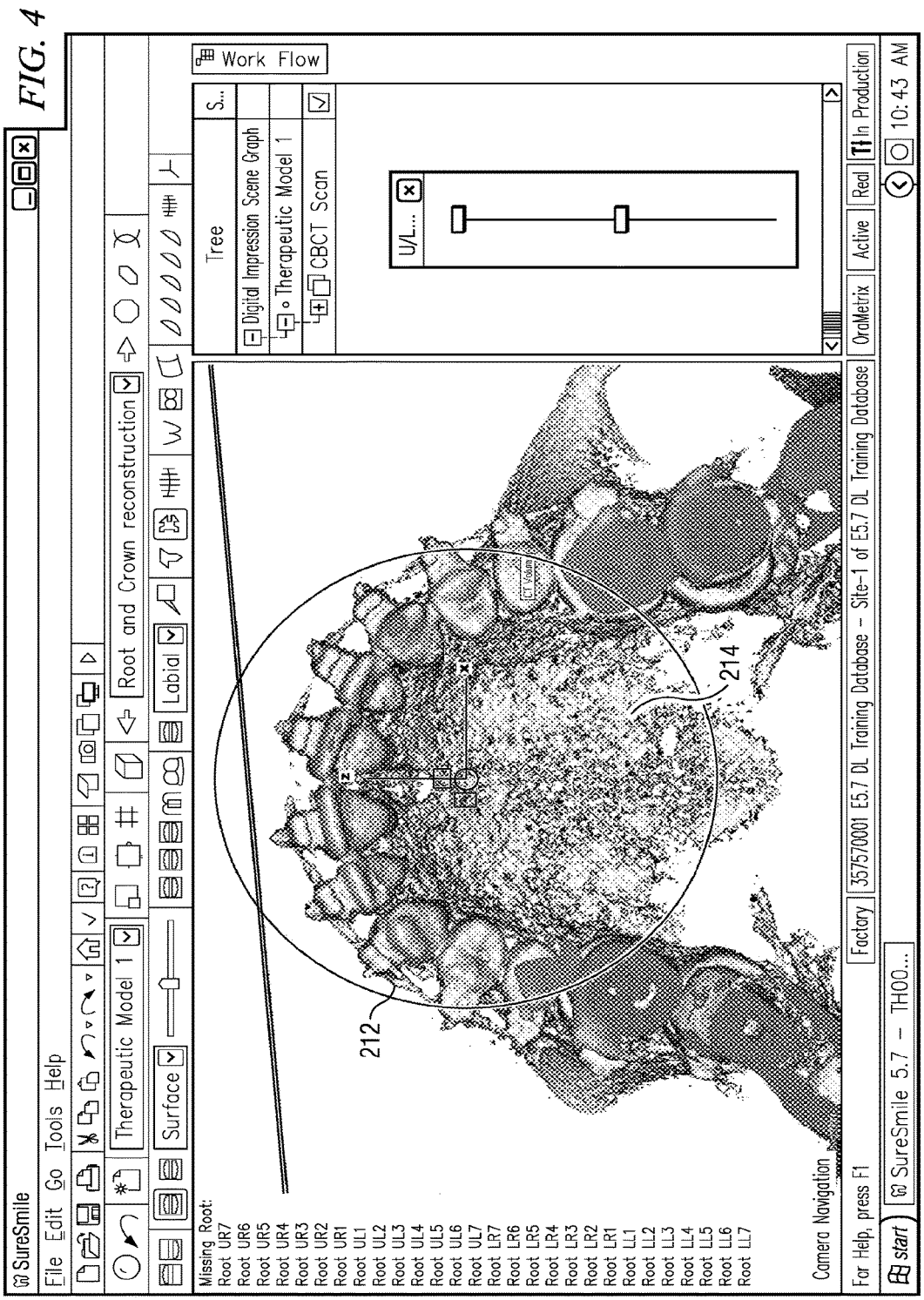

FIG. 4 shows a volume scan 212 from CBCT imaging with noise 214 caused by slight movement of the dentition by the patient while imaging was in progress.

Although other types of deficiencies are not shown by way of figures, one skilled in art would appreciate that volume scanning with CBCT or Mill has certain inherent disadvantages.

Figure 5:
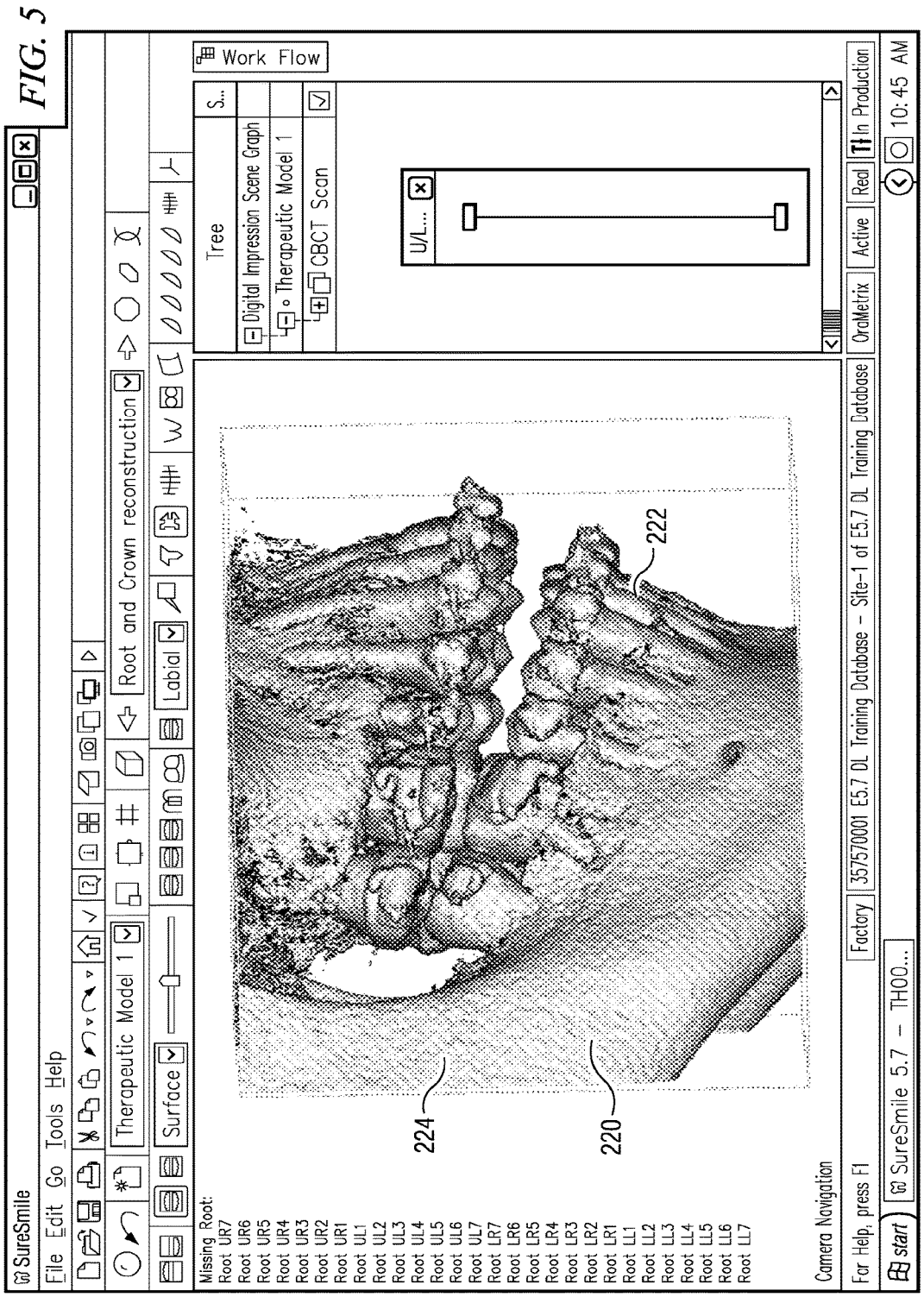

FIG. 5 shows a side view 220 of both jaws of a patient with teeth with roots 222 and jaw bones 224 of the dentition of the patient developed from the CBCT volume scan data.

Figure 6:
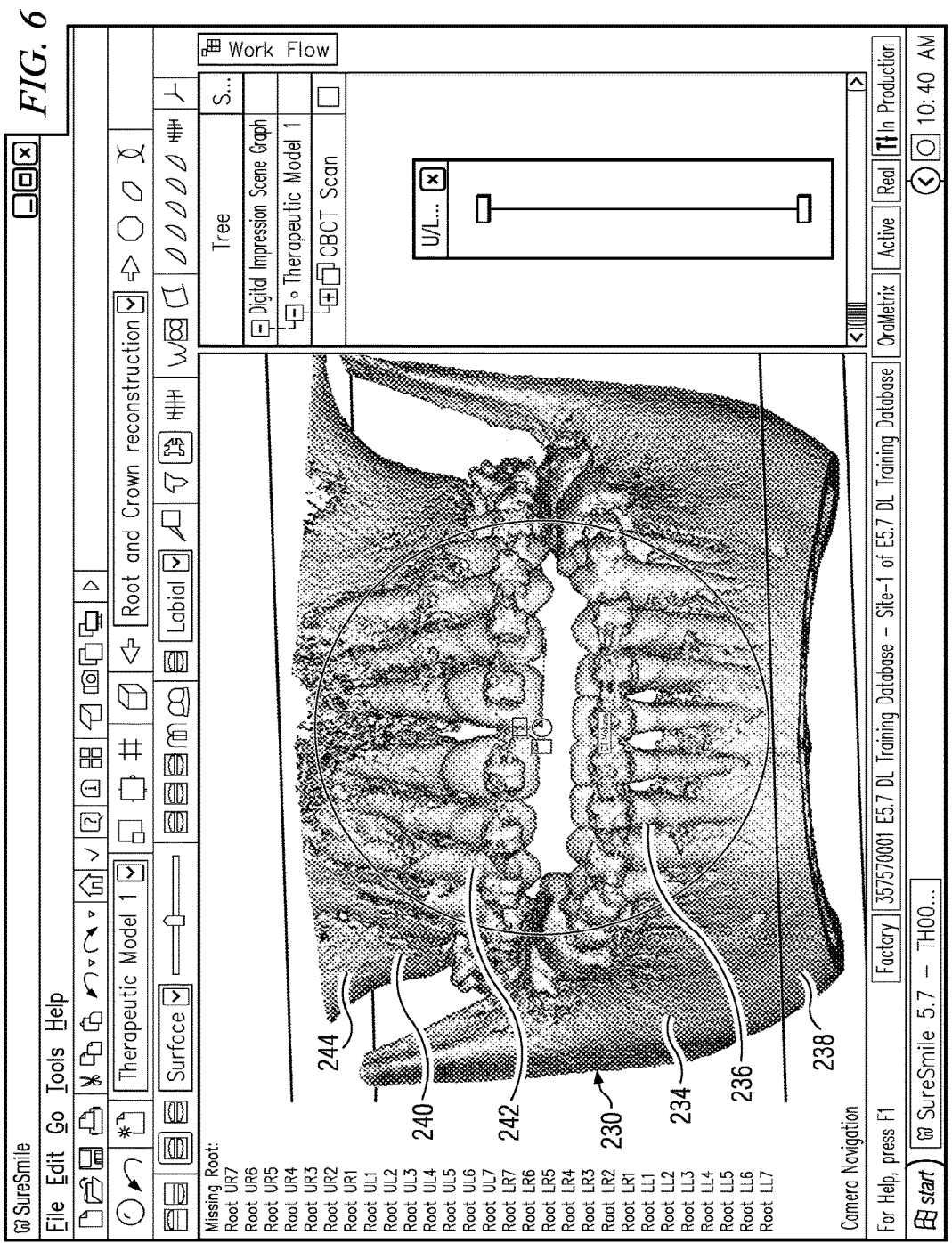

FIG. 6 shows a front view 230 of both jaws of the patient, lower jaw 234 and upper jaw 240, with teeth and roots 236 in the lower jaw and 242 in the upper jaw, and jaw bones 238 of the lower jaw and 244 of the upper jaw of the dentition of the patient developed from the CBCT volume scan data. The brackets placed on the patient's teeth are shown as well.

Figure 7:
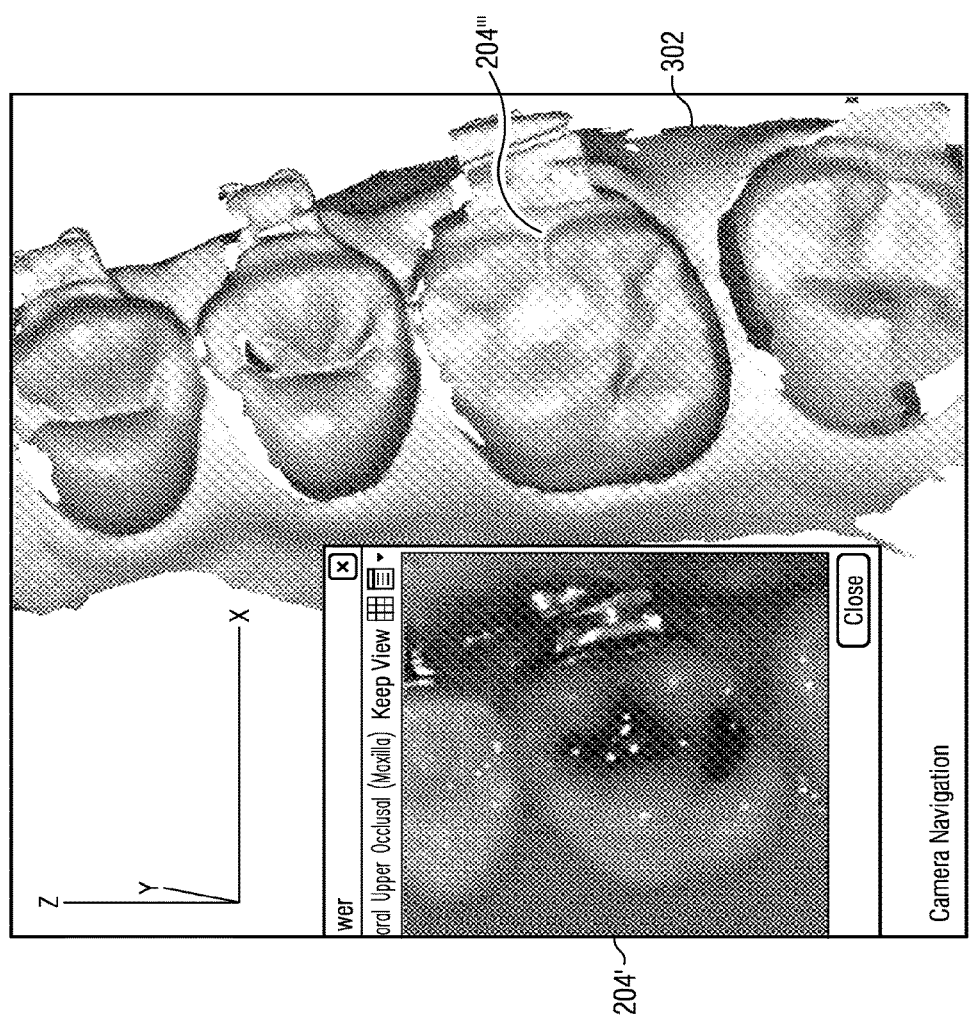
FIGS. 7-8 show data from surface scan of a patient at different stages of processing.

FIGS. 7-6 show data from surface scan of a patient at different stages of processing.

FIG. 7 shows surface scan 302 of the partial dentition of a patient. Also shown is the same tooth 204' with a metal filling previously shown in FIG. 2. Surface scan 204' corresponding to tooth 204' is perfectly acceptable even though the tooth has metal fillings.

Figure 8:
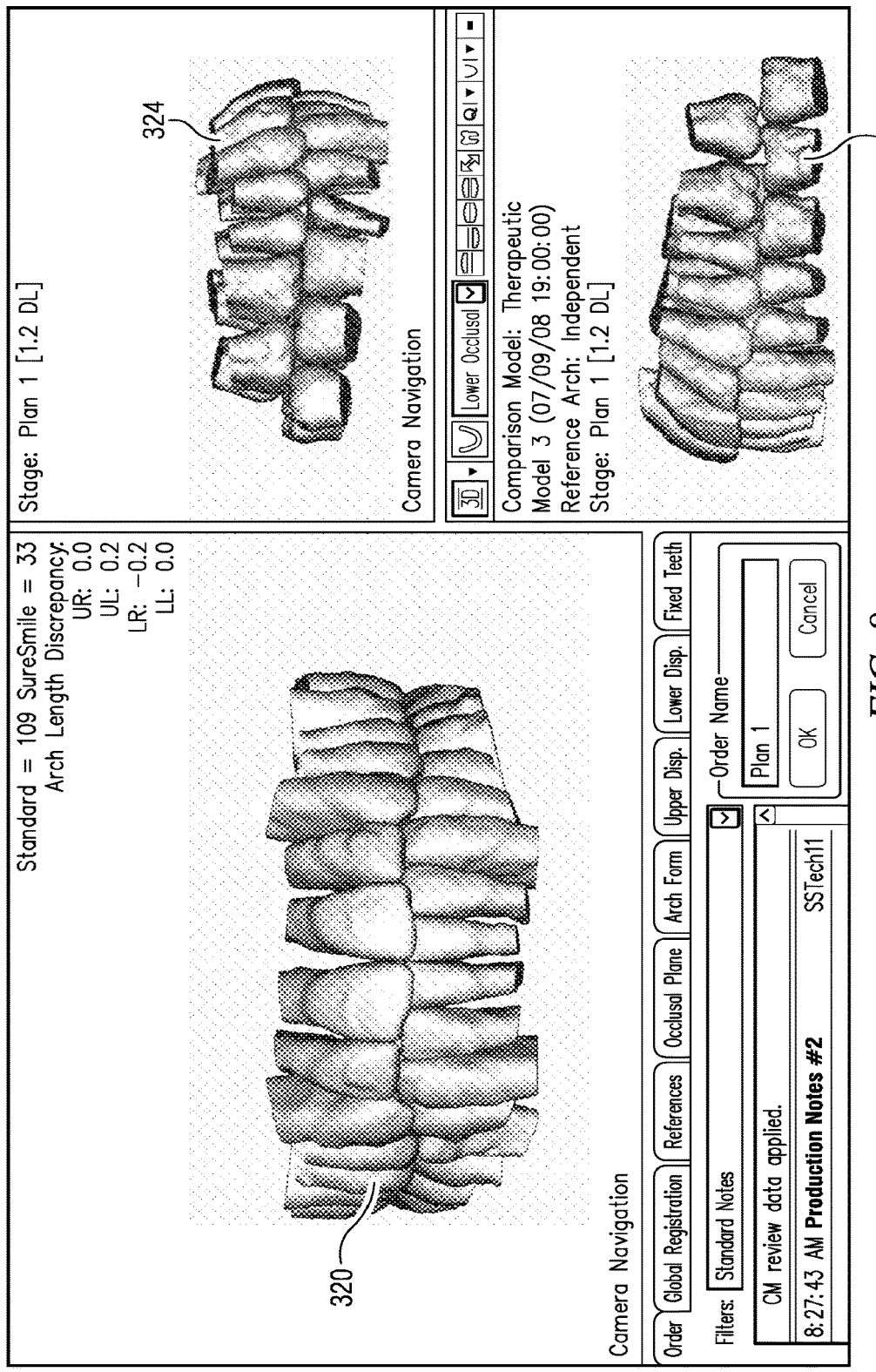

FIG. 8 shows final modeling of teeth, in front view 320 and side views 324 and 328, obtained from surface scanning of the dentition of a patient. While tooth crowns are displayed in the model, tooth roots and jaw bones are missing.

FIGS. 9-14 show data from the CBCT volume scan of a patient being combined with the data from surface scan of the same patient at different stages of processing.

Figure 9:
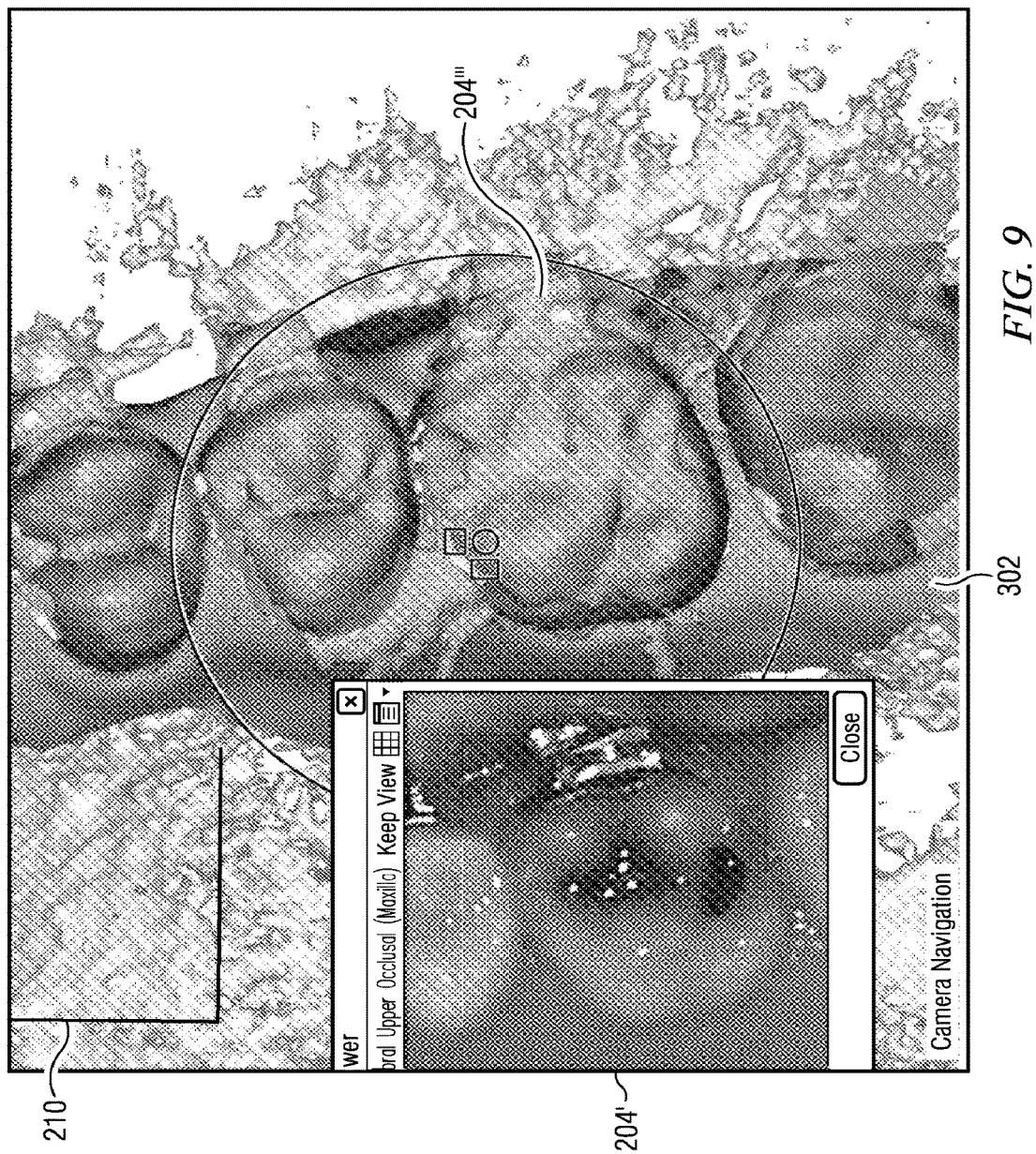
FIGS. 9-14 show data from the CBCT volume scan of a patient being combined with the data from surface scan of the same patient at different stages of processing.

FIG. 9 shows a part of the surface scan data 302 previously shown in FIG. 7 super imposed over the volume scan data 210 previously shown in FIG. 3. Also shown is the same tooth 204' with a metal filling previously shown in FIG. 2. Because of the surface scan data, tooth representation 204" of tooth 204' is acceptable in this case.

Figure 10:
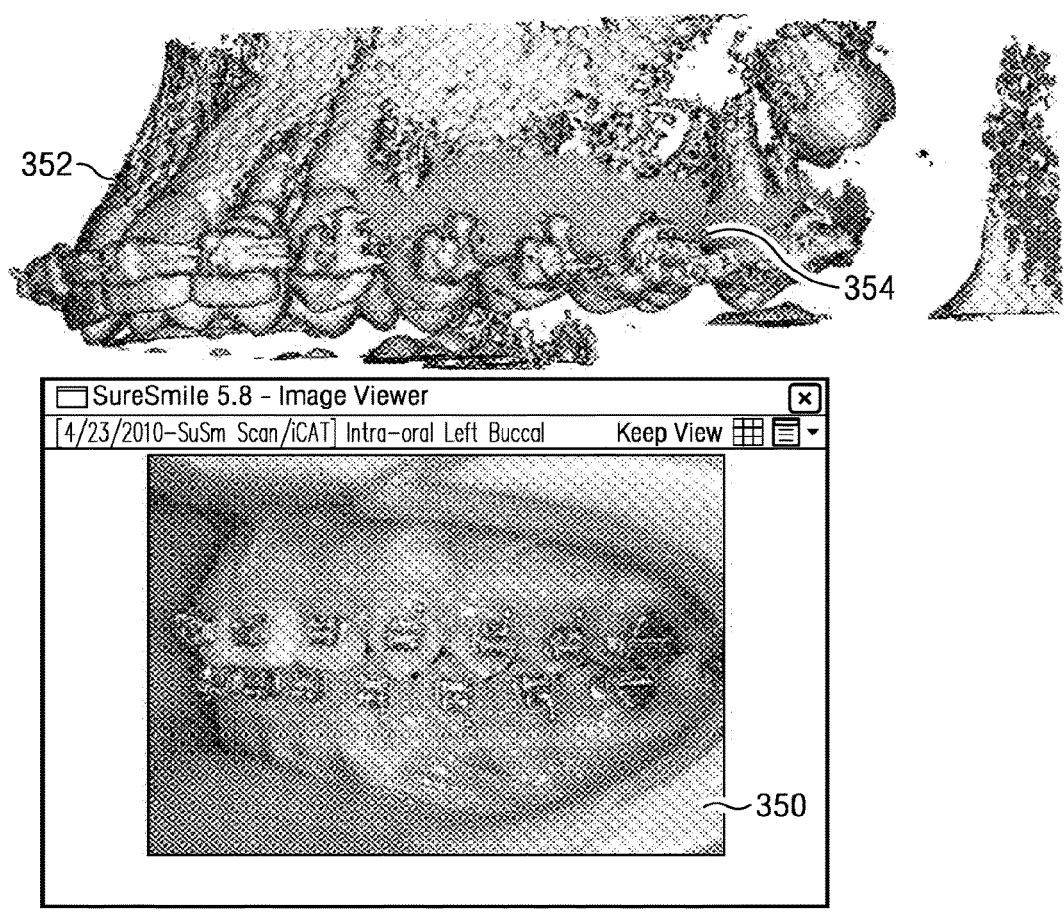

FIG. 10 shows another example 354 of a part of surface scan data super imposed over volume scan data 352. Also shown in this figure is a photographic view of the mouth 350 of the patient that was scanned.

Figure 11:
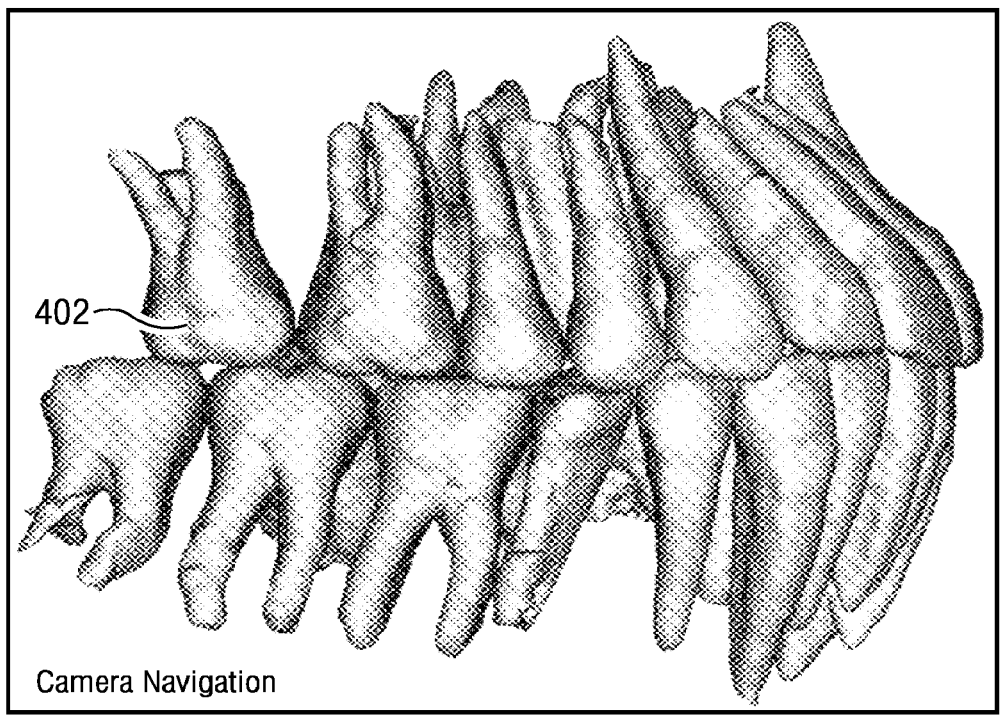

FIG. 11 shows a finished model 402 of the teeth with roots of a patient obtained by registering the mesh data from the surface scan with the mesh data from the volume scan of the dentition of a patient.

Figure 12:
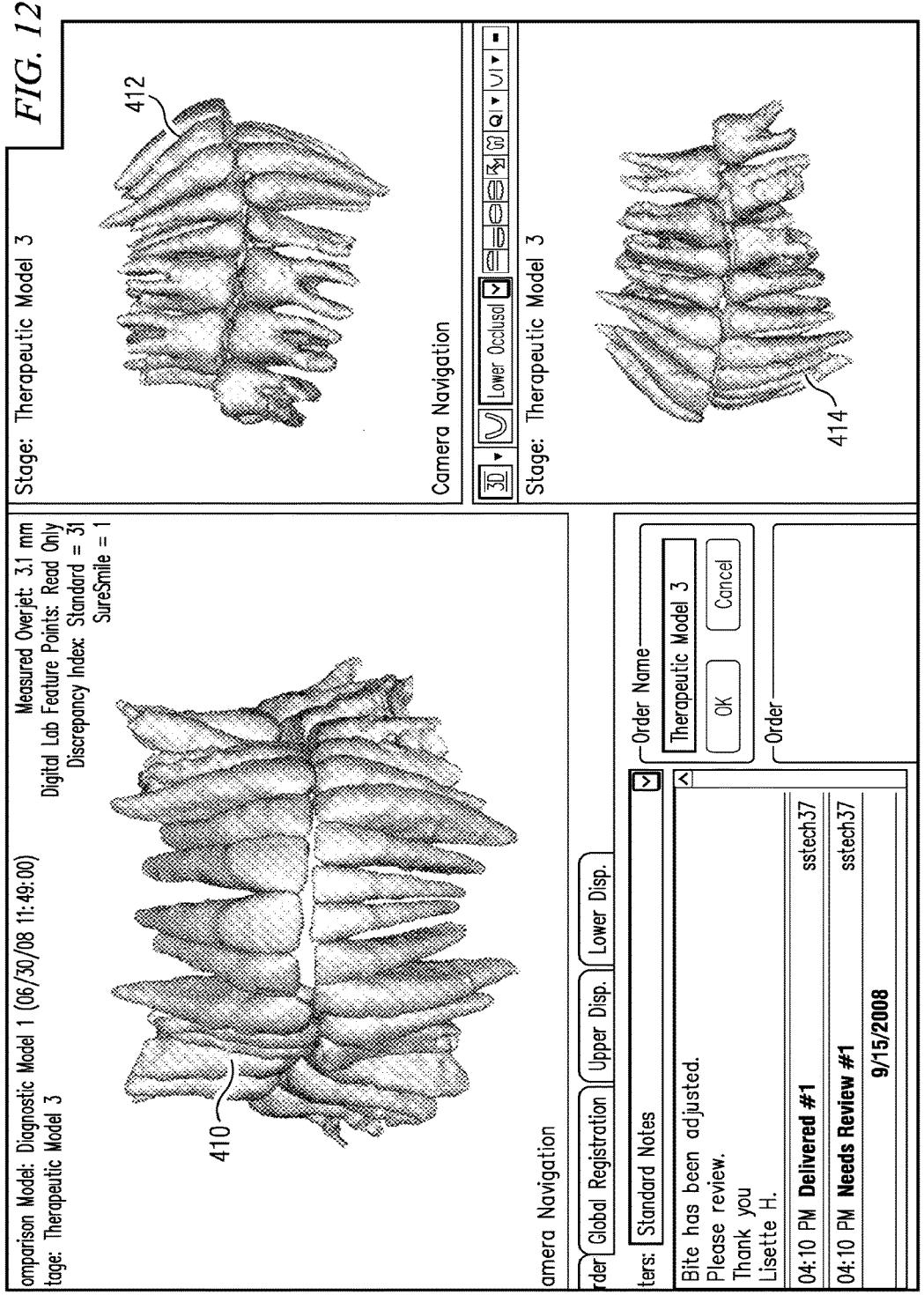
Figure 13:
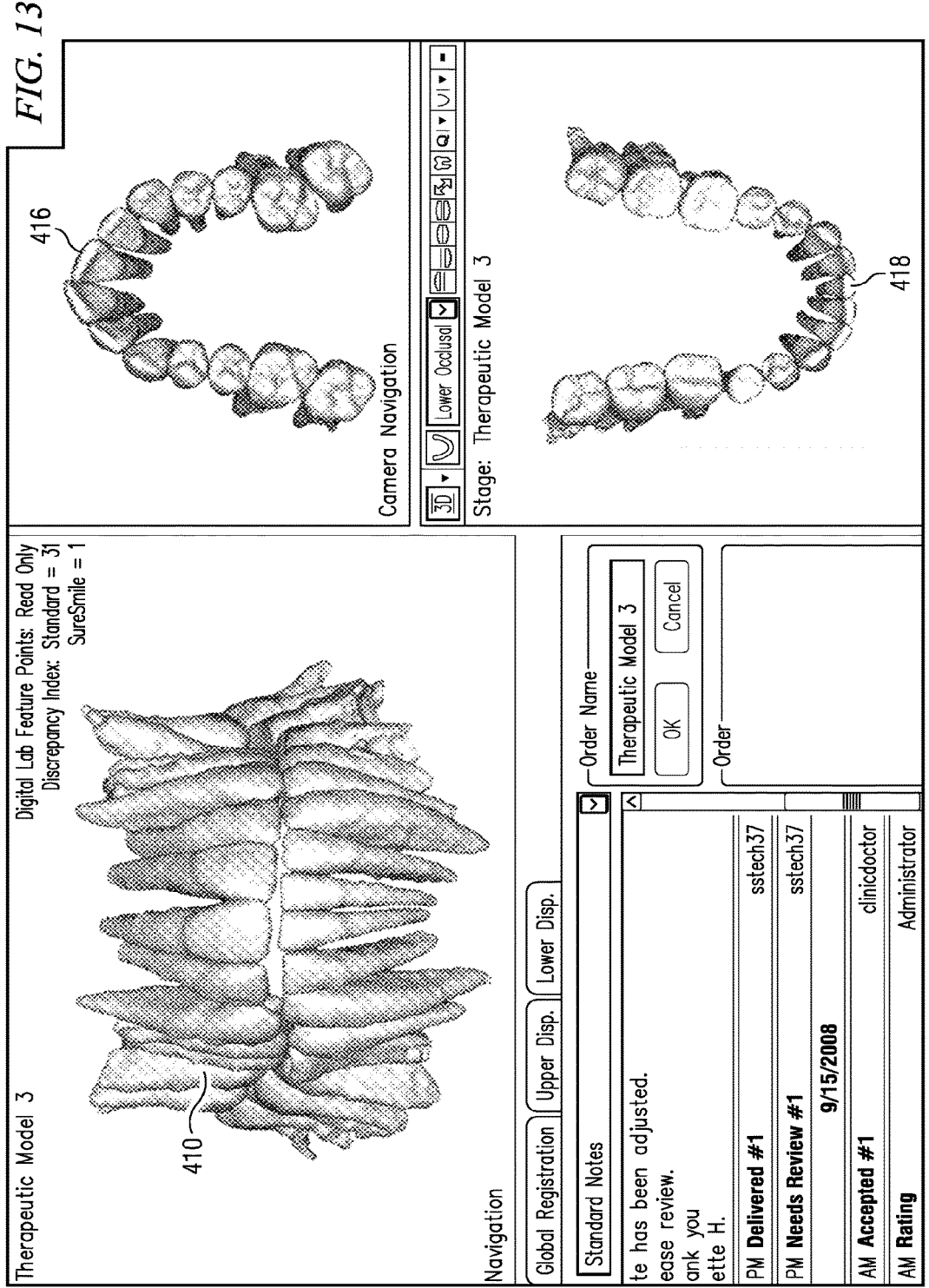

FIGS. 12 and 13 show different views 410, 412, 414, 416 and 418 of the teeth model shown in FIG. 11.

Figure 14:
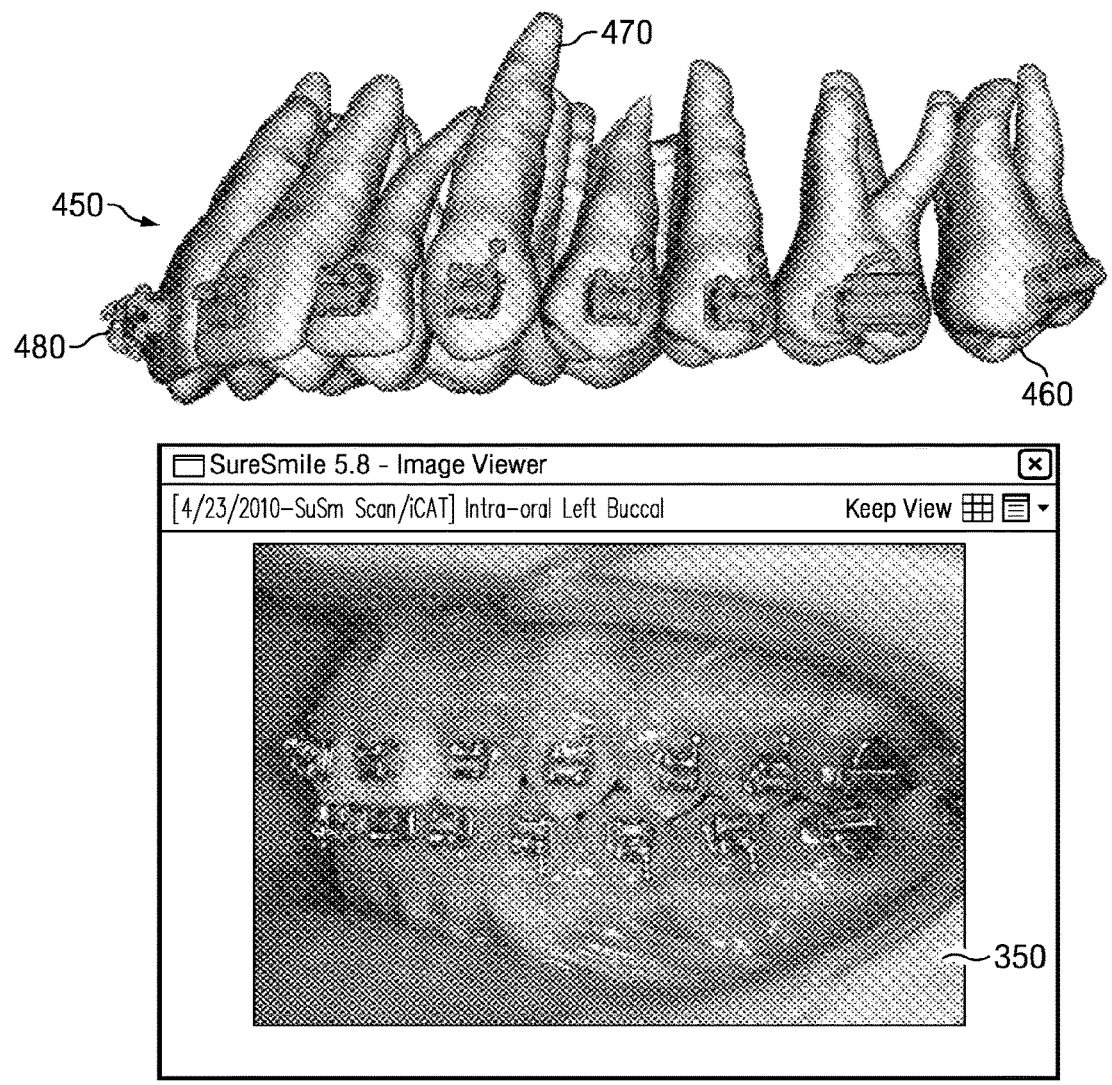

FIG. 14 shows the three-dimensional final model 450 teeth with crowns 460 and roots 470 having brackets 480 placed on the teeth.

FIGS. 15-23 show various views of unified three dimensional virtual craniofacial and dentition model derived from the volume scan data.

The preferred embodiment of the invention discloses an apparatus comprising, in combination, a computer-readable medium storing data representing a unified three dimensional virtual craniofacial and dentition model of actual, as-is static and functional anatomy of a patient, the data comprising:

(a) data representing facial bone structure of the patient including the upper jaw and lower jaw;

(b) data representing facial soft tissue of the patient;

(c) data representing teeth including crowns and roots of the patient, the data including information of the position of the roots relative to each other and relative to the facial bone structure of the patient including the upper jaw and the lower jaw;

The data representing parts (a), (b) and (c) of unified three dimensional virtual craniofacial and dentition model of the patient are constructed solely from digital data obtained by scanning as-is anatomy of craniofacial and dentition structures of the patient with a volume scanning device;

(d) data representing three dimensional virtual models of the patient's upper and lower gingiva, wherein the data represent three dimensional virtual models of the patient's upper and lower gingiva are constructed from scanning the patient's upper and lower gingiva either (a) with a volume scanning device, or (a) with a surface scanning device; the data (d) subsequently associated with data (c); and (e) data representing function of the patient's jaw movements and smile; wherein the data representing function of the patient's jaw movements and smile are obtained through video imaging, jaw tracking, or photographs;

wherein data (a), (b), (c), (d) and (e) are represented in the medium as individual static and/or dynamic anatomical object(s) of the patient; and a viewing program for viewing data (a), (b) (c), (d) and (e) on a display of the workstation wherein data (a), (b) (c), (d) and (e) can be displayed individually or in any combination on command of a user of the workstation using the viewing program.

Figure 15:
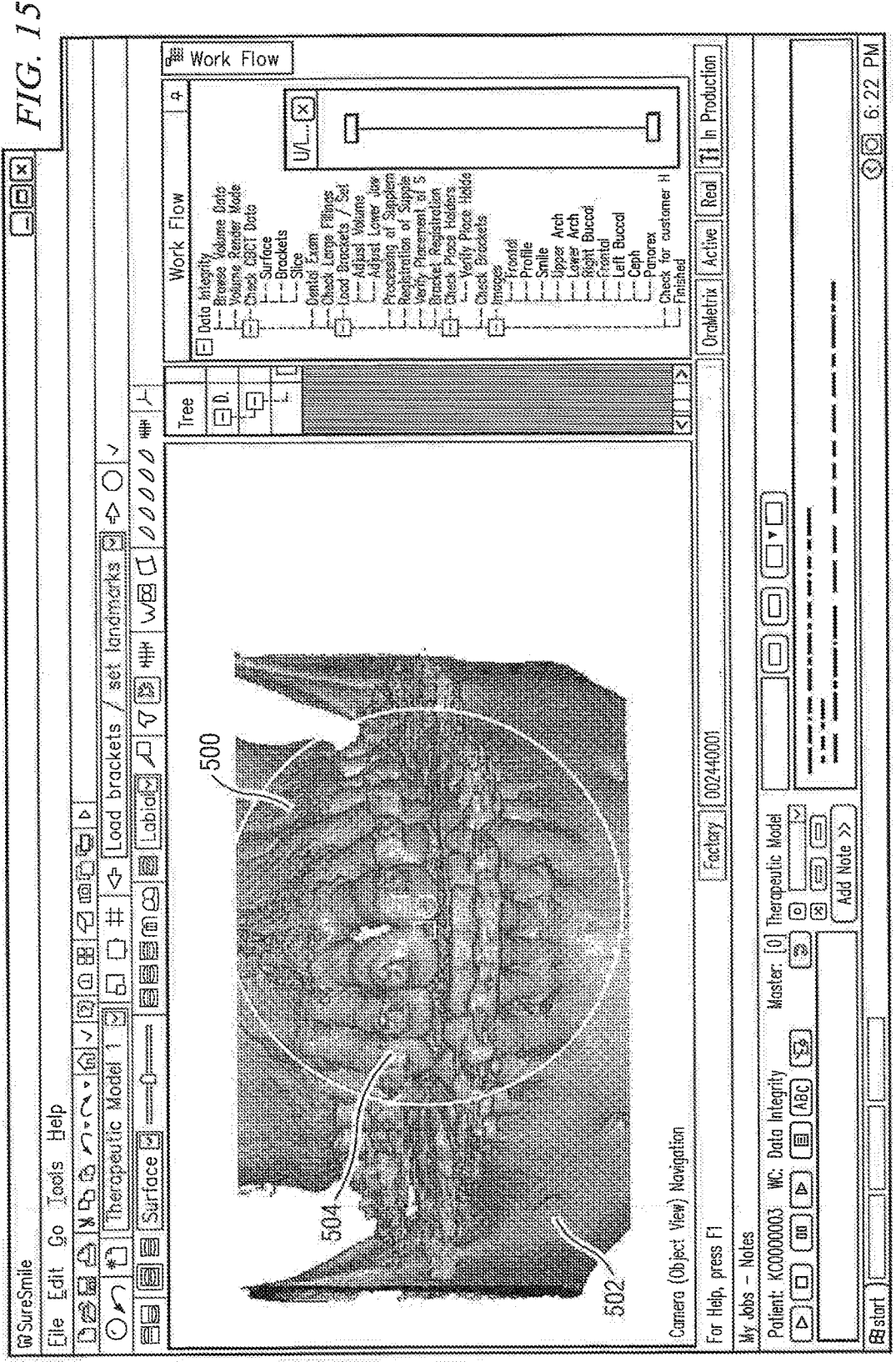
FIGS. 15-23 show various views of unified three dimensional virtual craniofacial and dentition model derived from the volume scan data.

FIG. 15 shows front view of upper jaw bone 500 and lower jaw bone 502 and teeth 504 of a patient.

Figure 16:
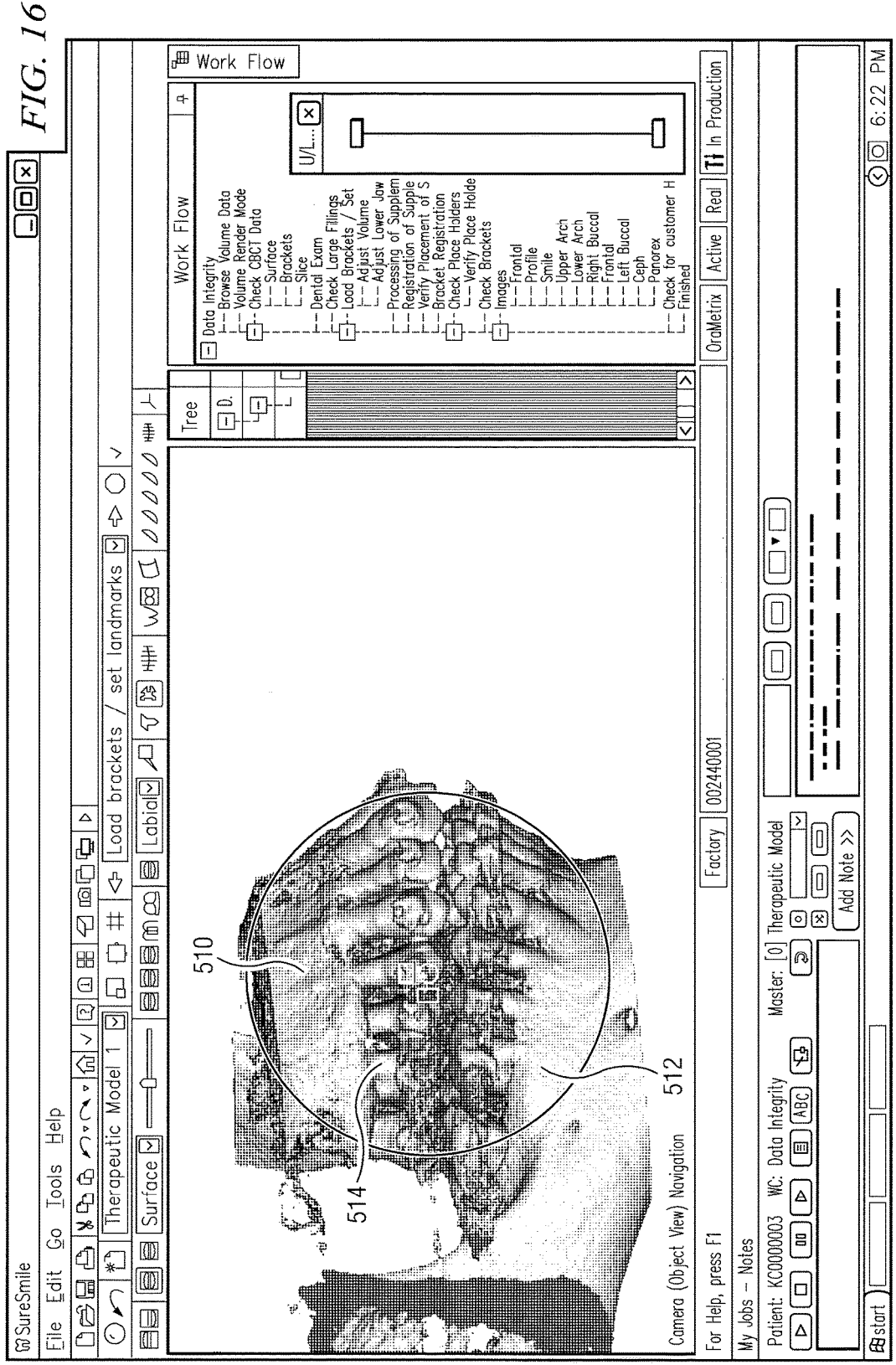

FIG. 16 shows right bucal view of upper jaw bone 510 and lower jaw bone 512 and teeth 514 of a patient.

Figure 17:
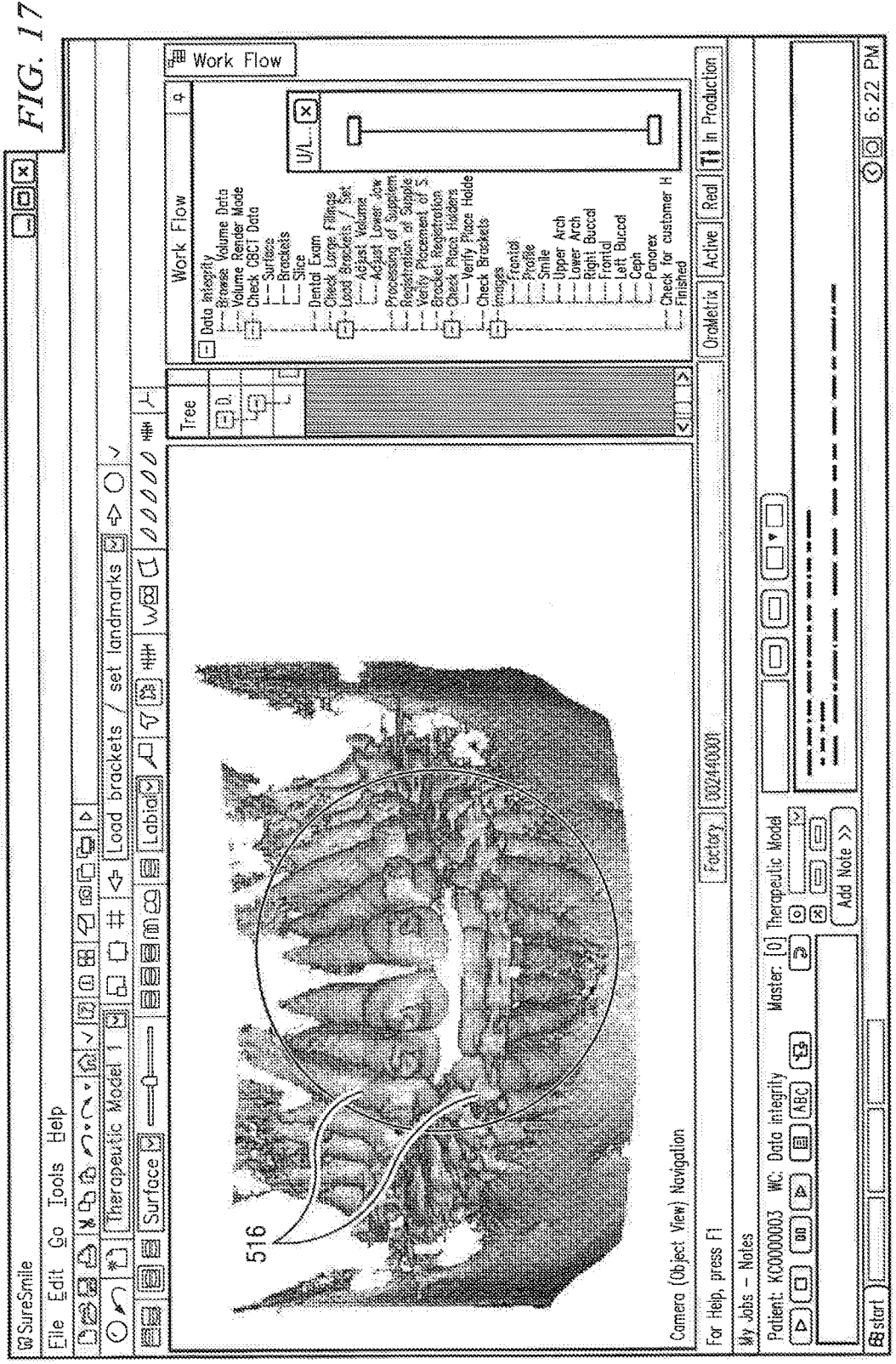

FIG. 17 shows front view of upper jaw and lower jaw with a portion of the jaw-bone removed so that more of the teeth 516 of the patient can be seen.

Figure 18:
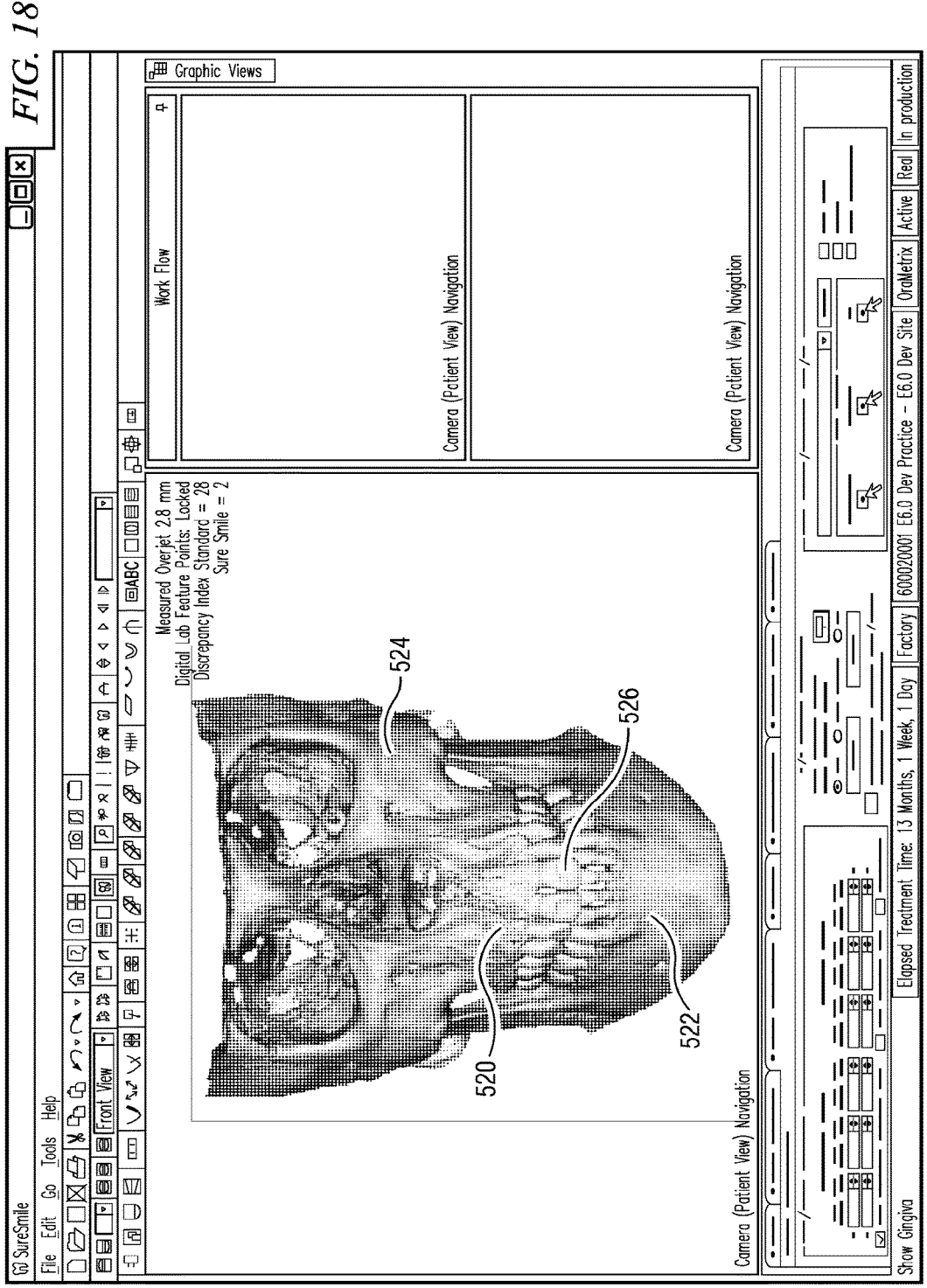

FIG. 18 shows front view of the upper jaw 520 and lower jaw 522 and facial bone 524 with modeled teeth 526, all obtained from the volume scan of the patient.

Figure 19:
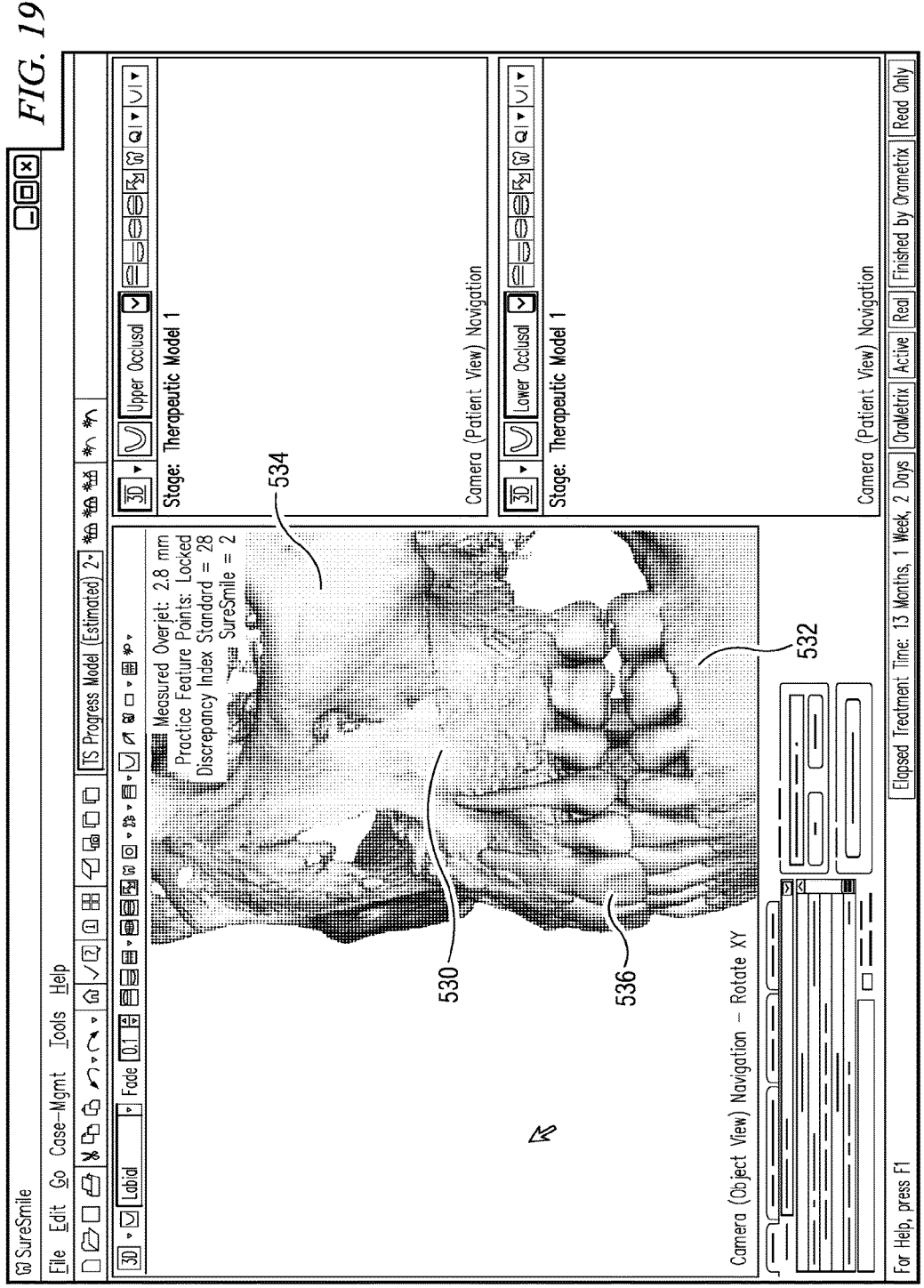

FIG. 19 shows left bucal view of the upper jaw 530 and lower jaw 532 and facial bone 534 with modeled teeth 536, all obtained from the volume scan of the patient.

Figure 20:
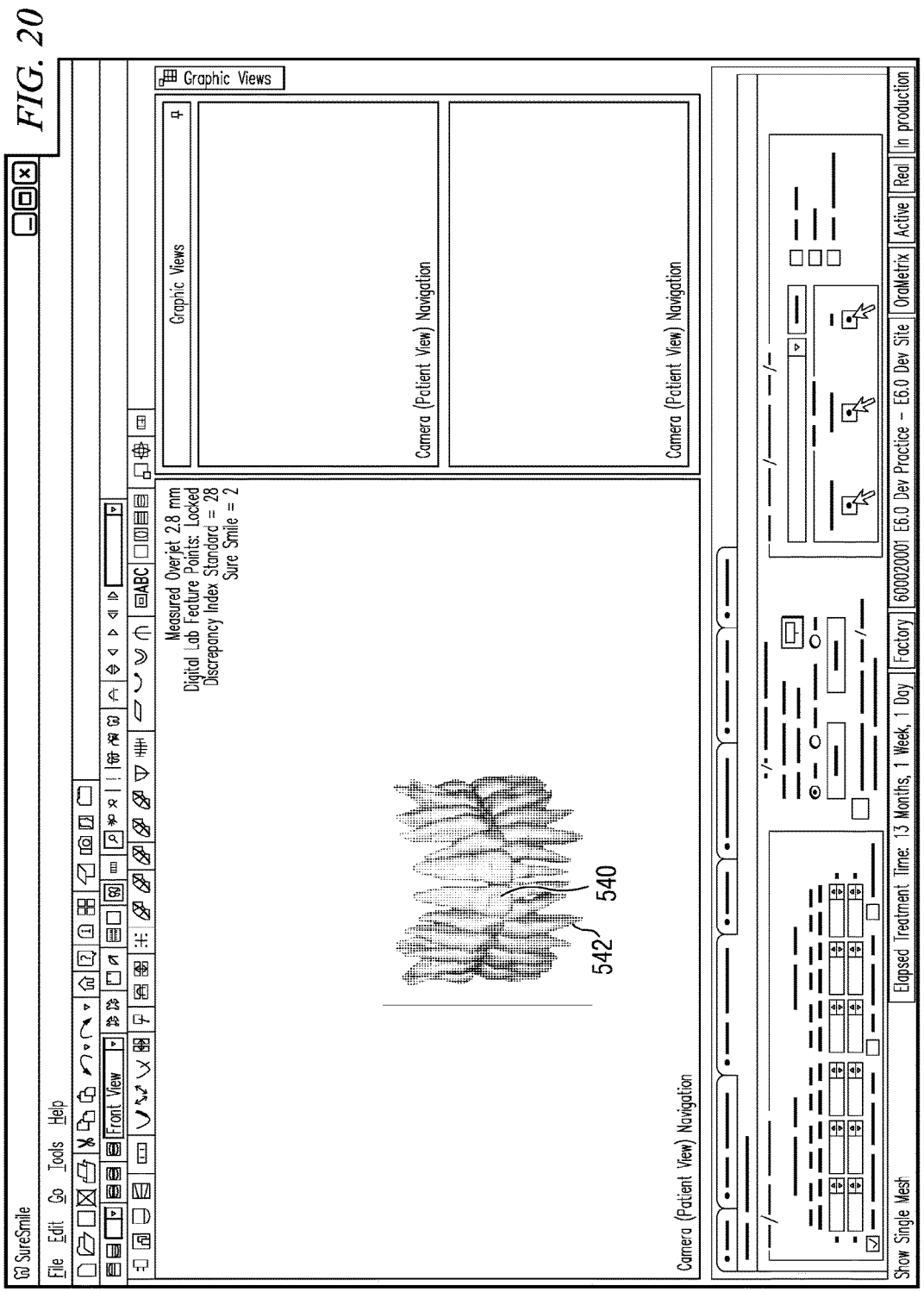

FIG. 20 shows teeth with crowns 540 and roots 542 in three-dimensions modeled from the volume scan data of the patient.

Figure 21:
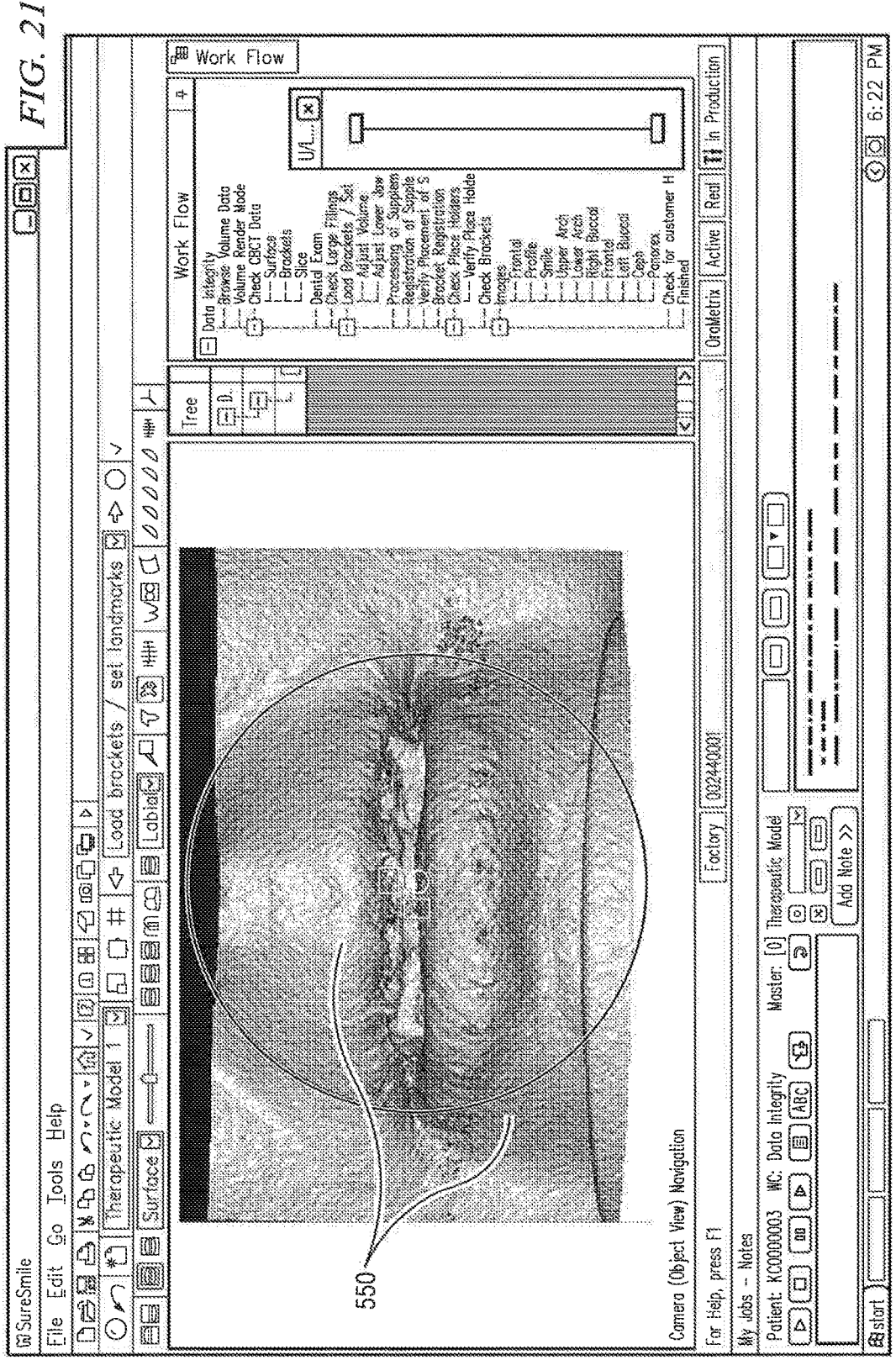

FIG. 21 shows facial soft tissue model 550 of the patient obtained from the volume scan data of the patient.

Figure 22:
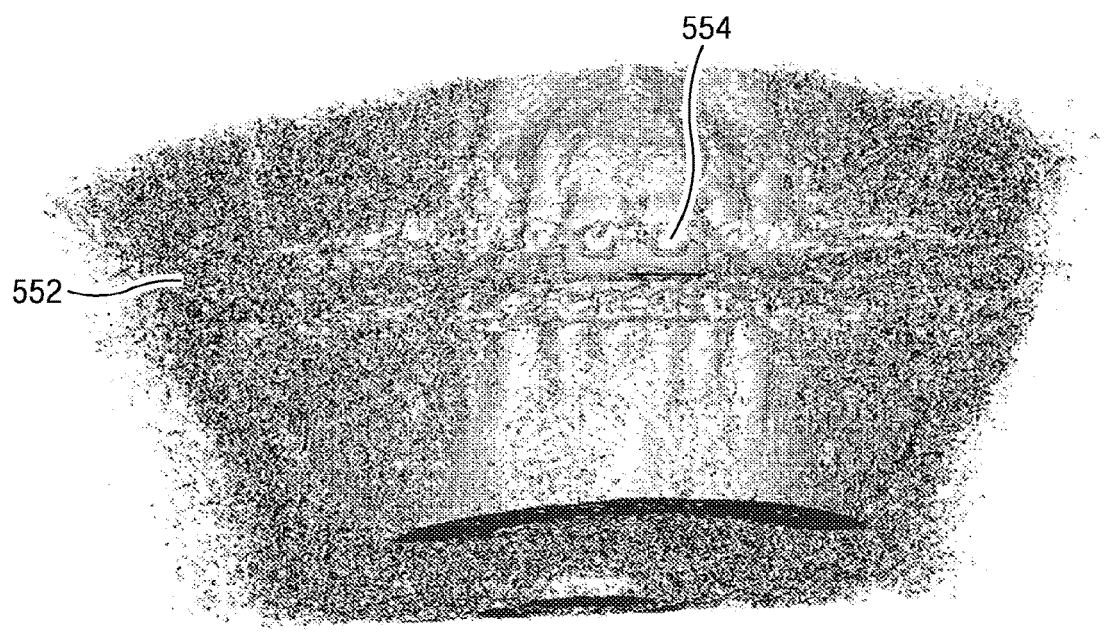

FIG. 22 shows a combination of facial tissue 552 and teeth 554 of the patient.

Figure 23:
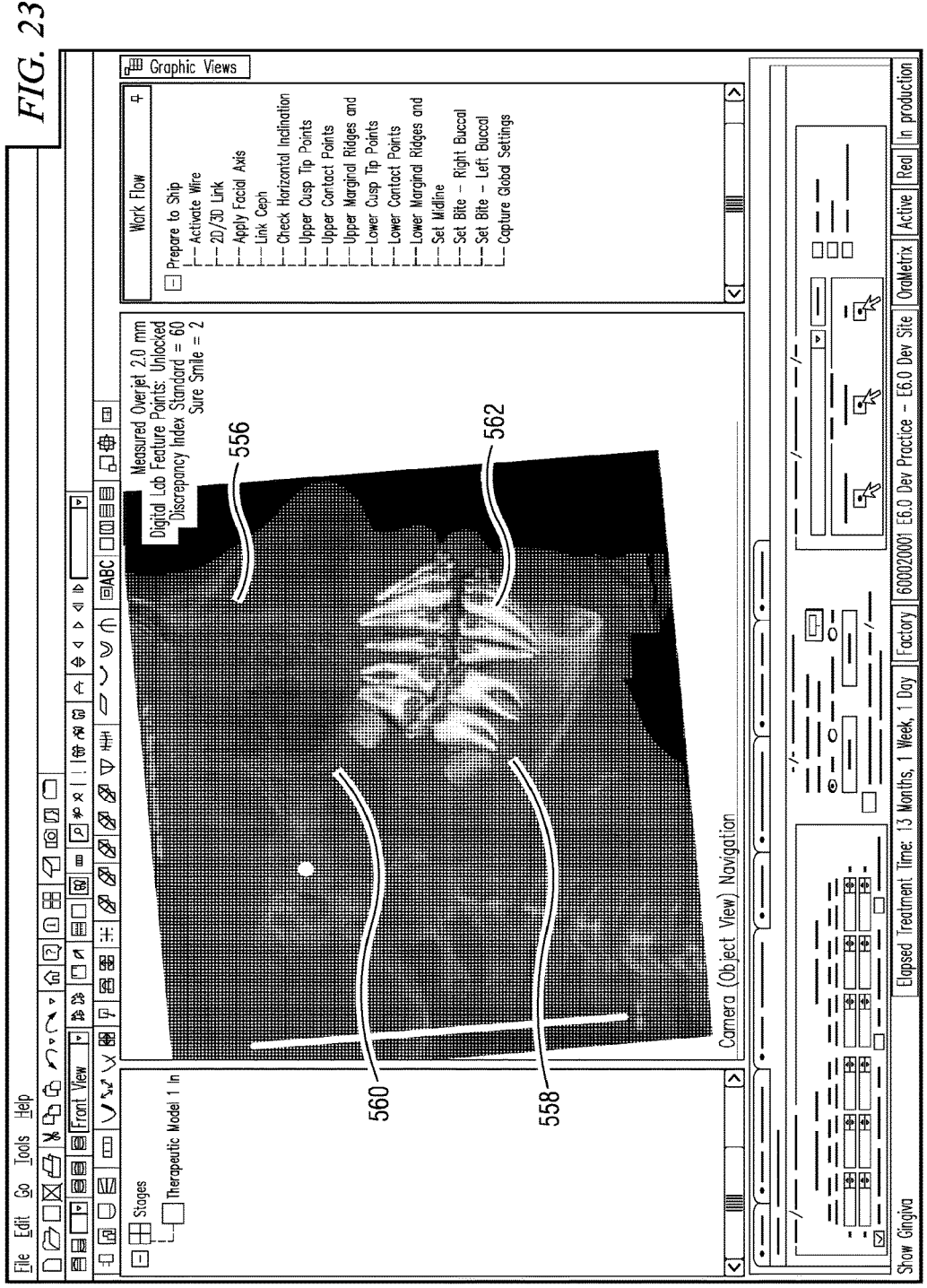

FIG. 23 shows ceph view of facial tissue 556 plus jaw bone 558 and facial bone 560 and of a patient with modeled teeth 562; all derived from the volume scan data of the patient.

Figure 24:
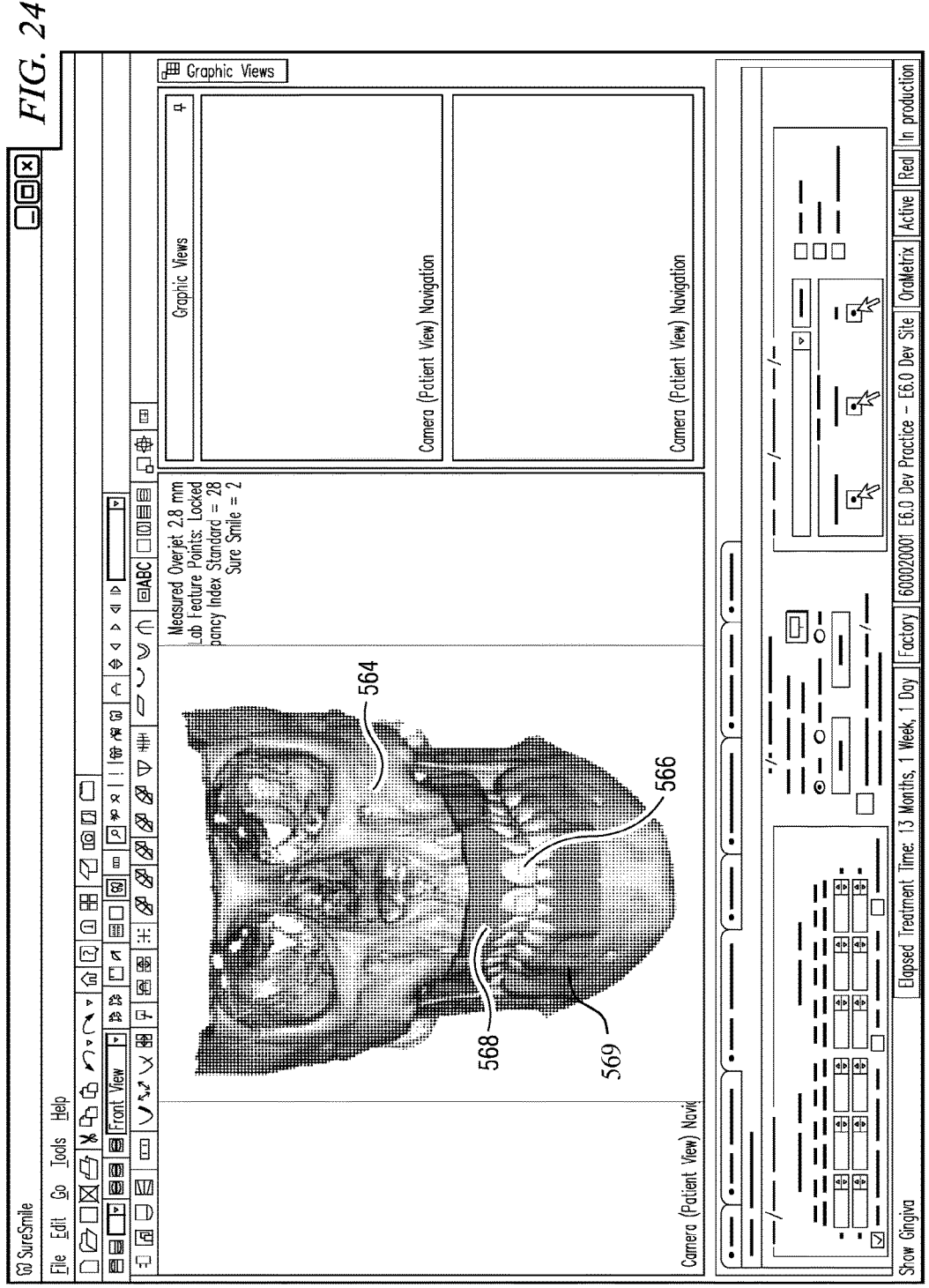
FIGS. 24-25 show modeling of gum tissue and its integration with the jaw bones and teeth of a patient.
Figure 25:
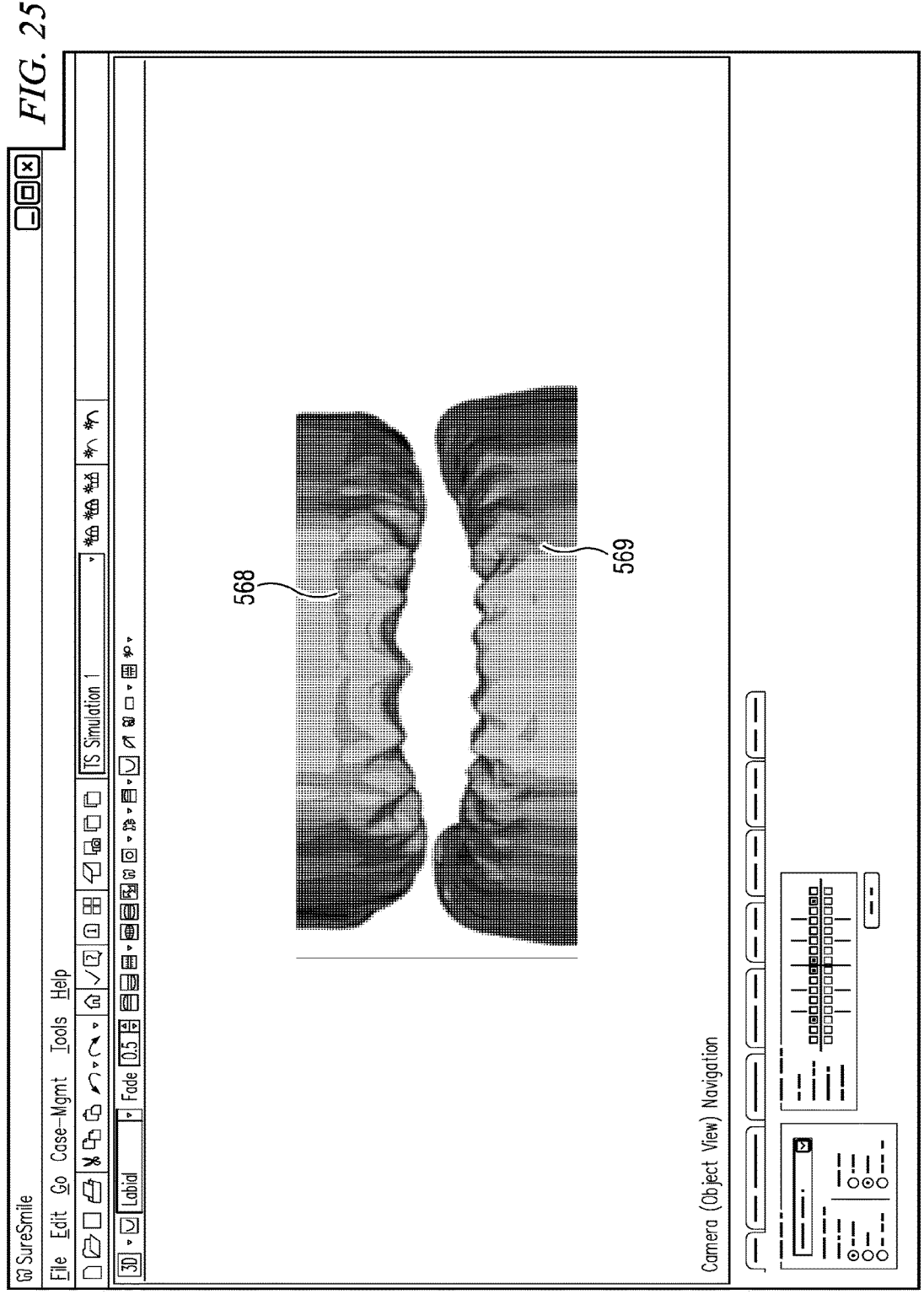

FIGS. 24-25 show modeling of gum tissue and its integration with the jaw bones and teeth of a patient.

FIG. 24 shows front view of the three dimensional craniofacial model of the patient, obtained by CBCT scanning showing bones 564 and teeth 566. The figure also shows gingiva bite model 568 and 569 of the patient registered with the jaws and teeth of the patient. This step is necessary because a jaw separating mouth piece is inserted in the patient's mouth while scanning with CBCT, which keeps the jaws of the patient open, and prevents scanning the bite. Therefore, the virtual model of the upper 568 and lower 569 gingiva of the patient, obtained from surface scanning data, as shown in FIG. 25, is registered with bones and teeth models of the patient obtained from the volume scan data.

FIG. 25 shows the virtual model of the upper gingiva 568 and lower gingiva 569 of the patient obtained by surface scanning of the patient's bite.

FIGS. 26-30 show modeling of brackets bonded to the patients teeth through volume scanning.

Figure 26:
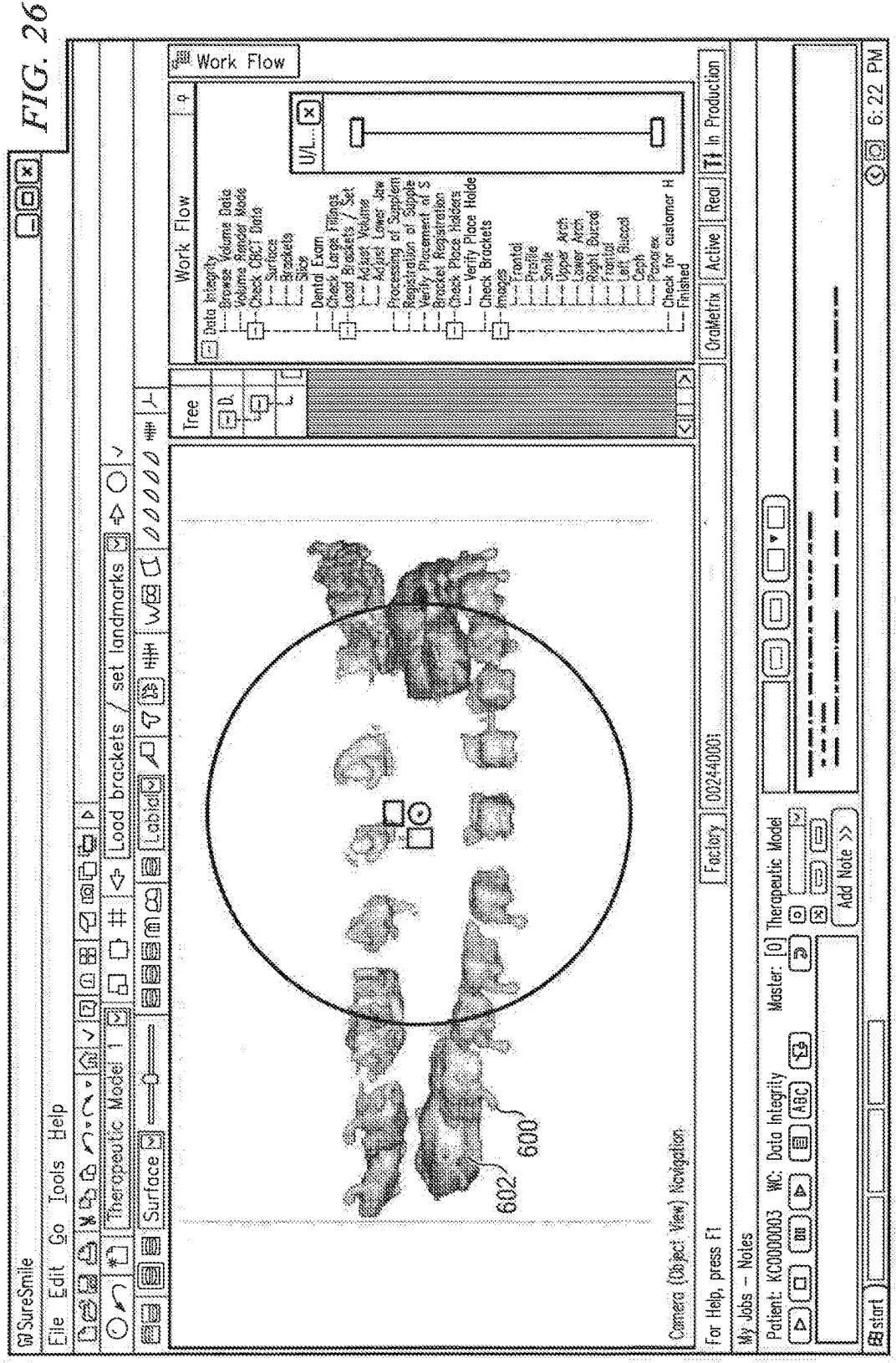
FIGS. 26-30 show modeling of brackets bonded to the patients teeth through volume scanning.

FIG. 26 shows front view of the three dimensional models of the brackets 600 placed on the patients teeth 602 obtained through volume scanning of the patient.

Figure 27:
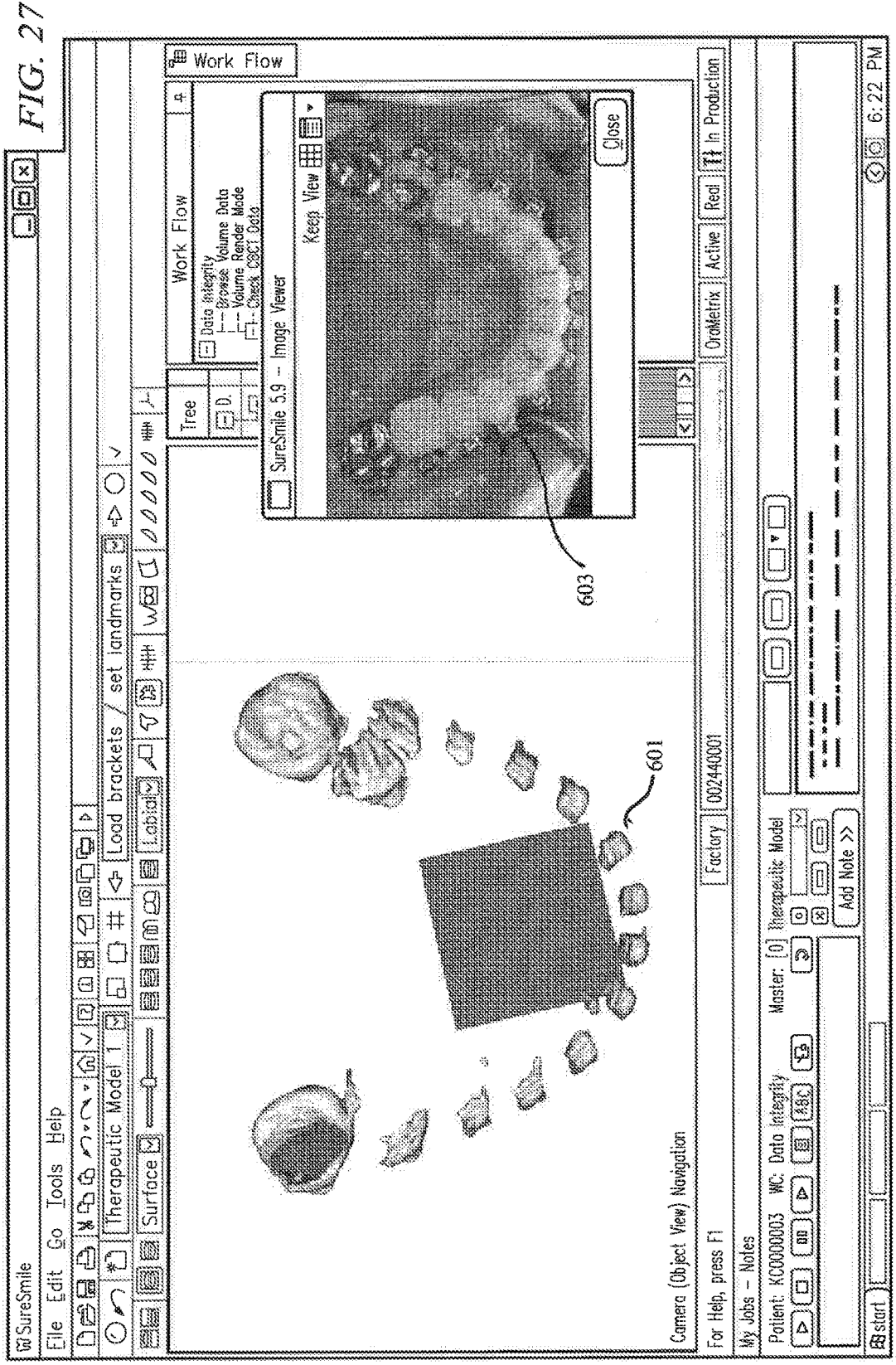

FIG. 27 shows another view of the layout of the bracket models 601 and 603 presented in FIG. 26.

Figure 28:
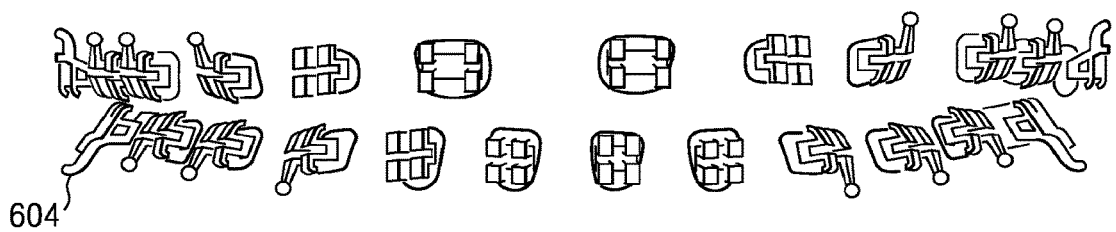

FIG. 28 shows the brackets in the form of line drawings 604.

Figure 29:
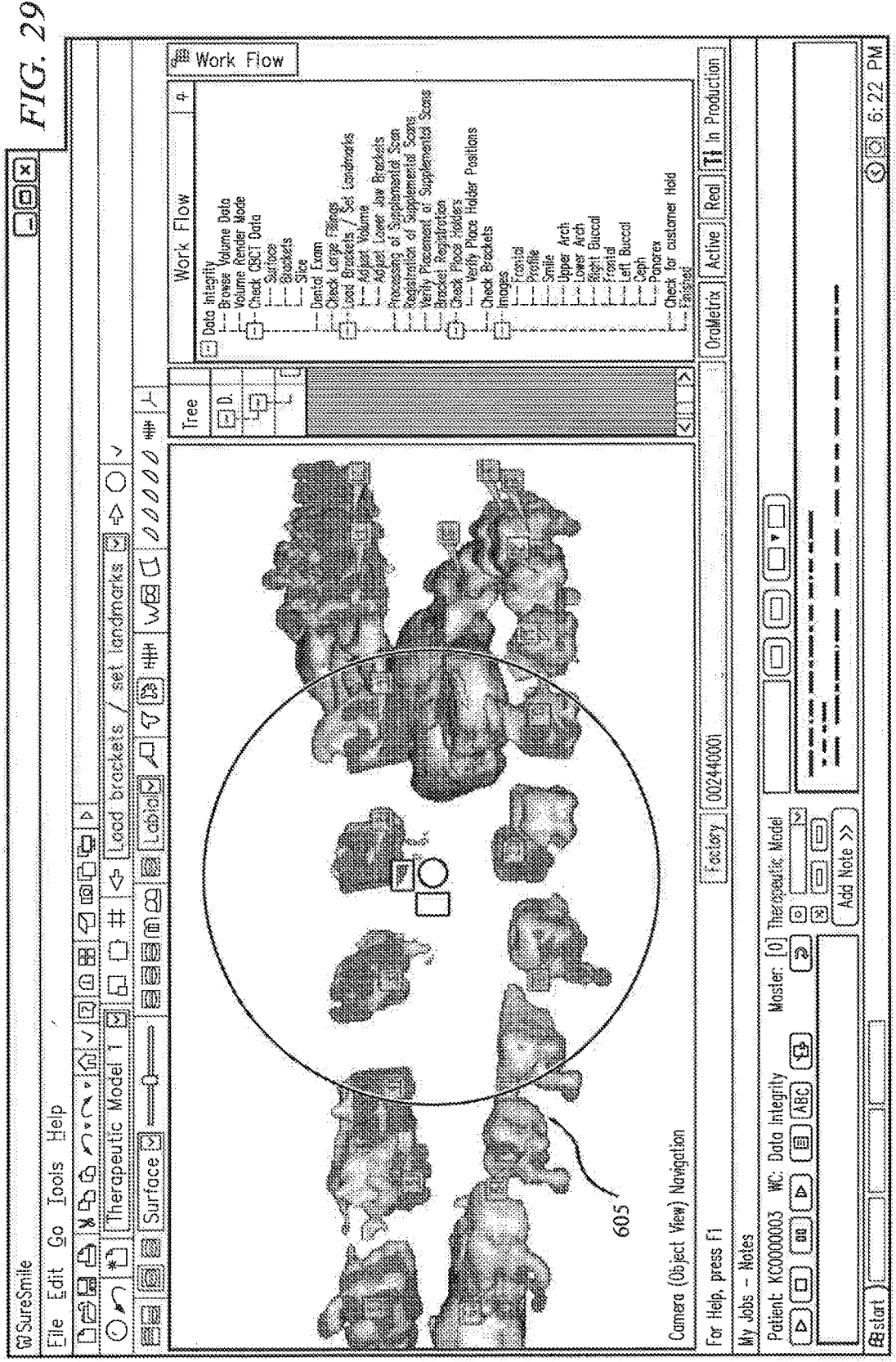

FIG. 29 shows models of the specific brackets, derived from the images of the scanned brackets, mounted on the models of the crowns 605 of the patient.

Figure 30:
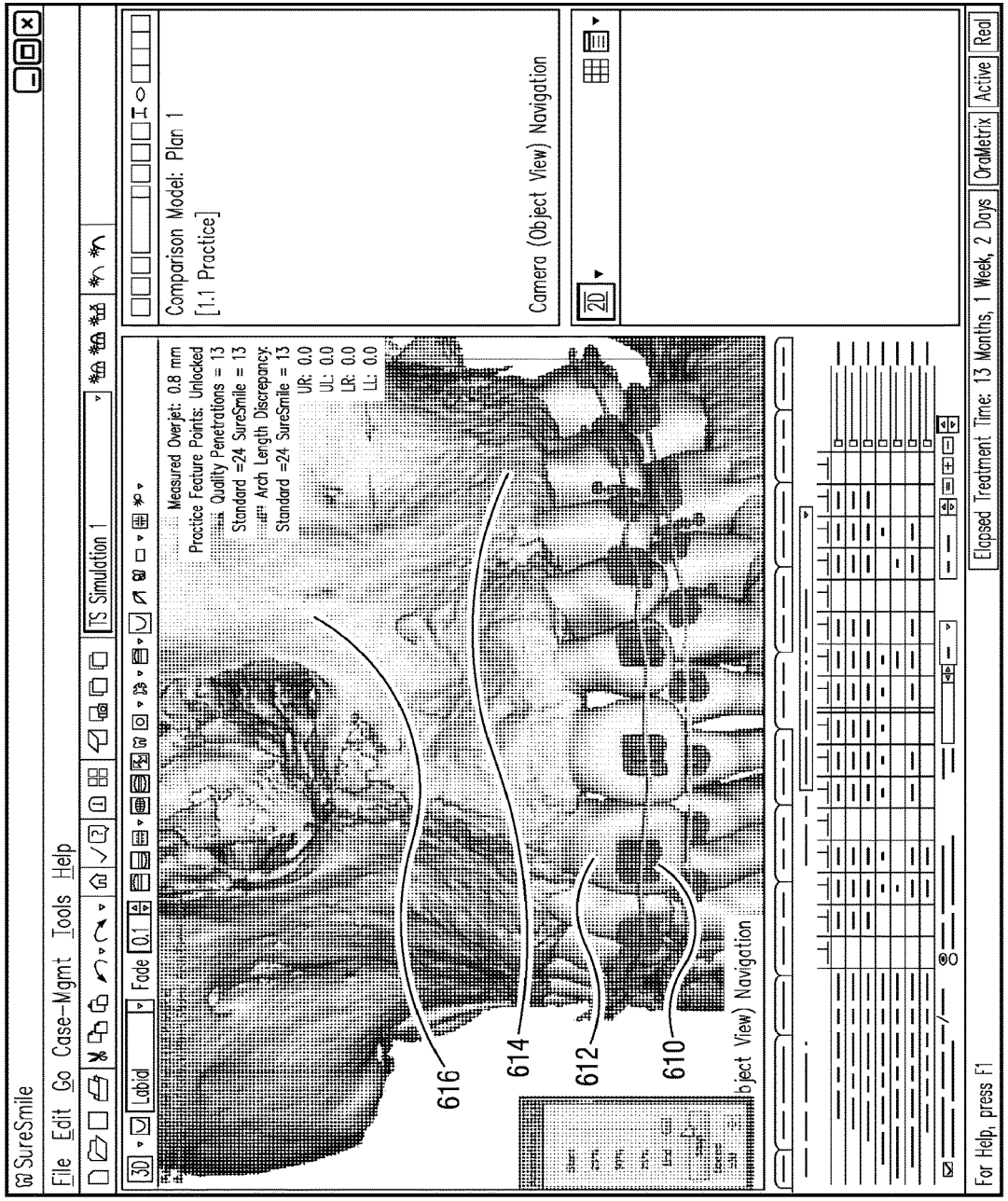

FIG. 30 shows models of the specific brackets 610, derived from the scanned images of the bracket, mounted on the models of the teeth 612 of the patient, along with the models of the jaw 614 and other facial bones 616 of the patient.

FIGS. 31-35 show model of the patient's bite obtained through surface scanning, and its integration with the patient's jaws and teeth.

Another preferred embodiment of the invention discloses method of planning comprehensive treatment of a patient, having a craniofacial deformity, skeletal abnormalities, soft tissue abnormalities, dental malocclusion, and dysfunction, by a practitioner, using a workstation comprising a computing platform having a graphical user interface, a processor and a computer storage medium containing digitized records pertaining to a patient, said digitized records including image data, and a set of software instructions providing graphical user interface tools for access to said digitized records, the method comprising the steps of:

(a) loading into the workstation a unified three dimensional virtual craniofacial and dentition model of said patient; wherein said unified three dimensional virtual craniofacial and dentition model comprises:

(i) facial bone structure including upper jaw and lower jaw;

(ii) facial soft tissue;

(iii) teeth including crowns and roots; wherein said roots are positioned relative to each other and relative to bones of said upper jaw and bones of said lower jaw;

(iv) upper and lower gingiva; and (v) data representing function of the patient's jaw movements and smile; wherein said data representing function of the patient's jaw movements and smile are obtained through video imaging, jaw tracking, or photographs;

wherein the virtual model comprising elements from (i), (ii), (iii), (iv) and (v) are individual and separate data objects and viewable individually or in any combination via the graphical user interface;

(b) examining said unified three dimensional virtual craniofacial and dentition model of said patient;

(c) identifying one or more abnormalities requiring surgery for correcting said one or more abnormalities in said patient's craniofacial and/dentition;

(d) creating a post-surgery desired setup of said patient's teeth, including movements of one or more of said teeth and movements within said bone structure, for curing said malocclusion;

(e) creating a pre-surgical setup of said patient's teeth while retaining said movements of one or more of said teeth, but removing said movements within said bone structure; both from said post-surgery desired setup;

(f) creating a pre-surgical setup of said patient's teeth while retaining said movements of one or more of said teeth, but removing said movements within said bone structure;

(g) adjusting said movements of one or more of said teeth in said pre-surgical setup thereby allowing room for said surgery for removing said one or more abnormalities; and creating adjusted pre-surgical setup;

(h) designing orthodontic appliances for said patient in accordance with said adjusted pre-surgical setup;

(i) designing orthodontic appliances for said patient in accordance with said post-surgical setup;

(j) designing surgical appliances for said patient in accordance with said pre-surgical setup;

(k) designing surgical appliances for said patient in accordance with said post-surgical setup; and (l) sending data for manufacturing appliances.

Figure 31:
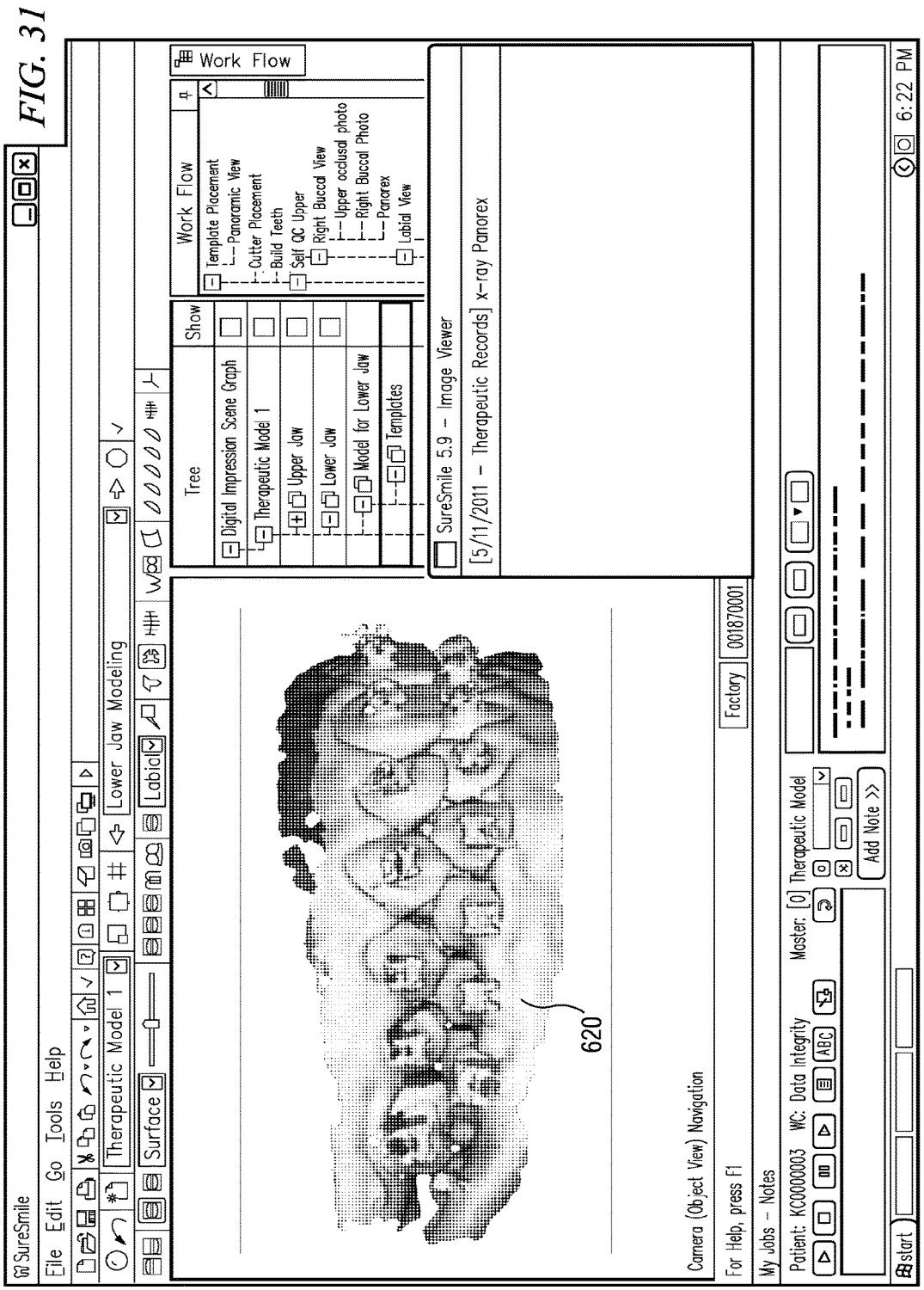
FIGS. 31-35 show model of the patient's bite obtained through surface scanning, and its integration with the patient's jaws and teeth.

FIG. 31 shows model of the patient's bite 620 obtained through surface scanning.

Figure 32:
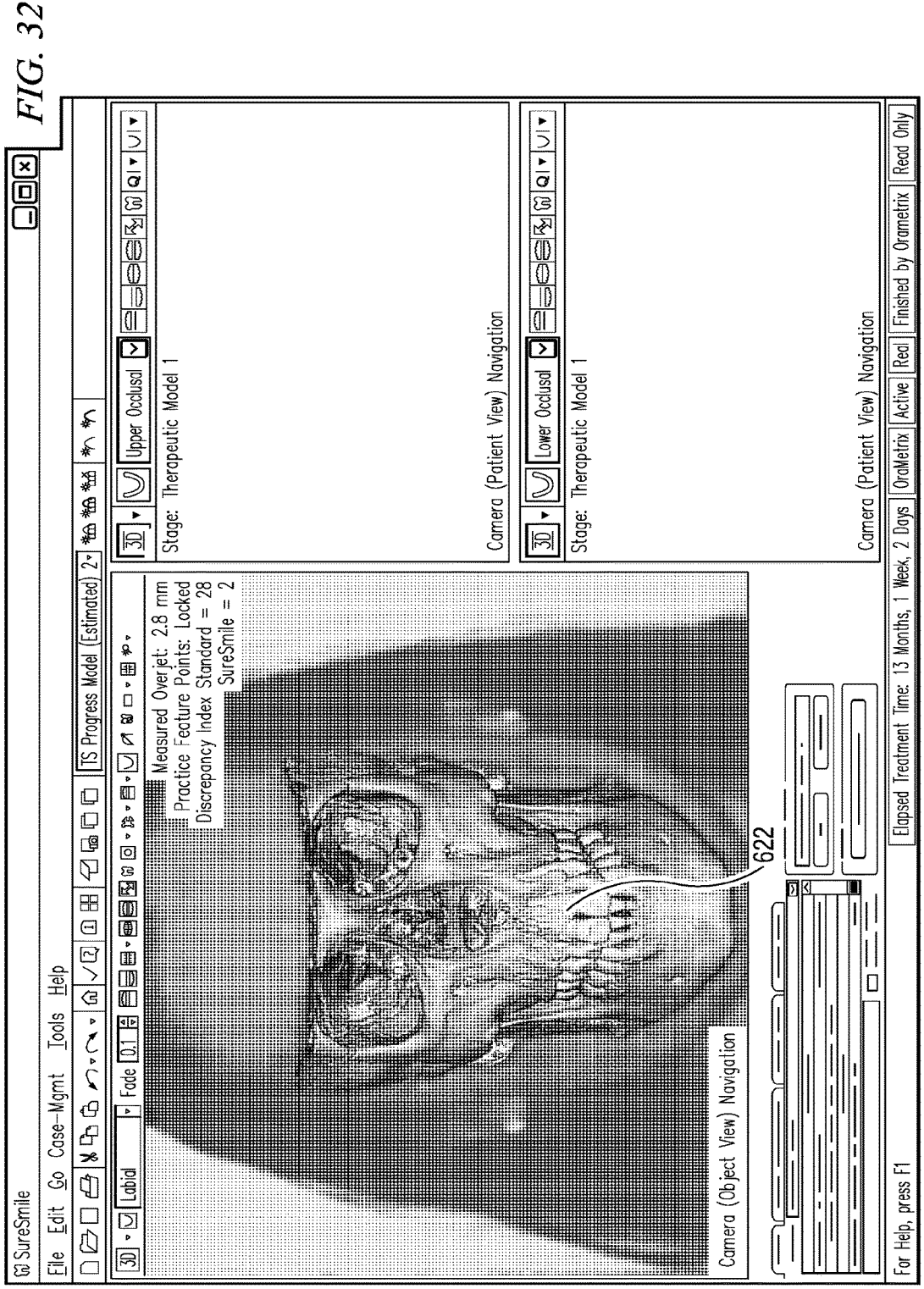

FIG. 32 shows integration of the bite scan model 622 with the jaw bones and teeth of the patient. The bite is shown in the closed position in this figure.

Figure 33:
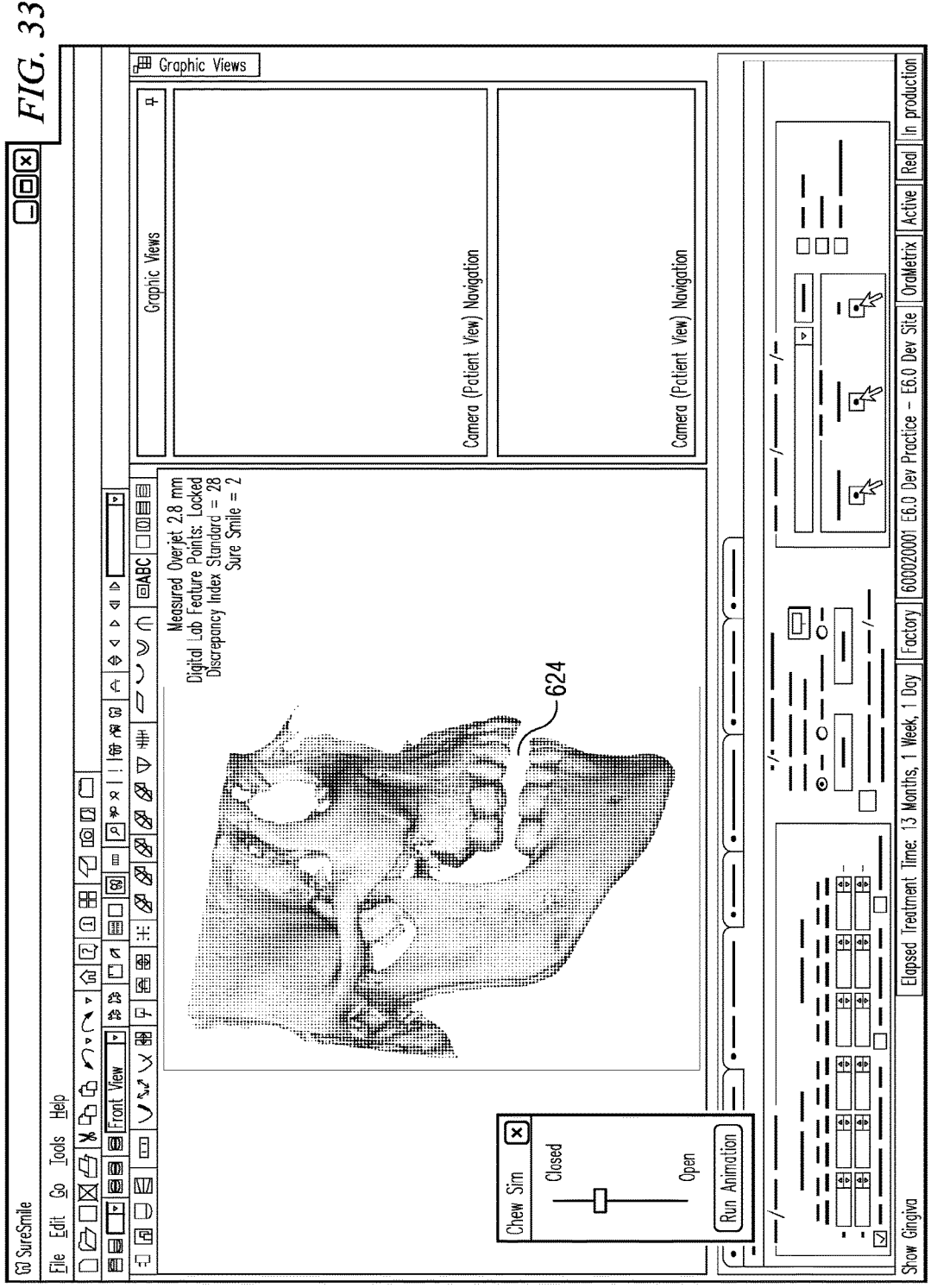

FIG. 33 shows bite in an open position 624 along with the facial and jaw bone structures of the patient in the right bucal view.

Figure 34:
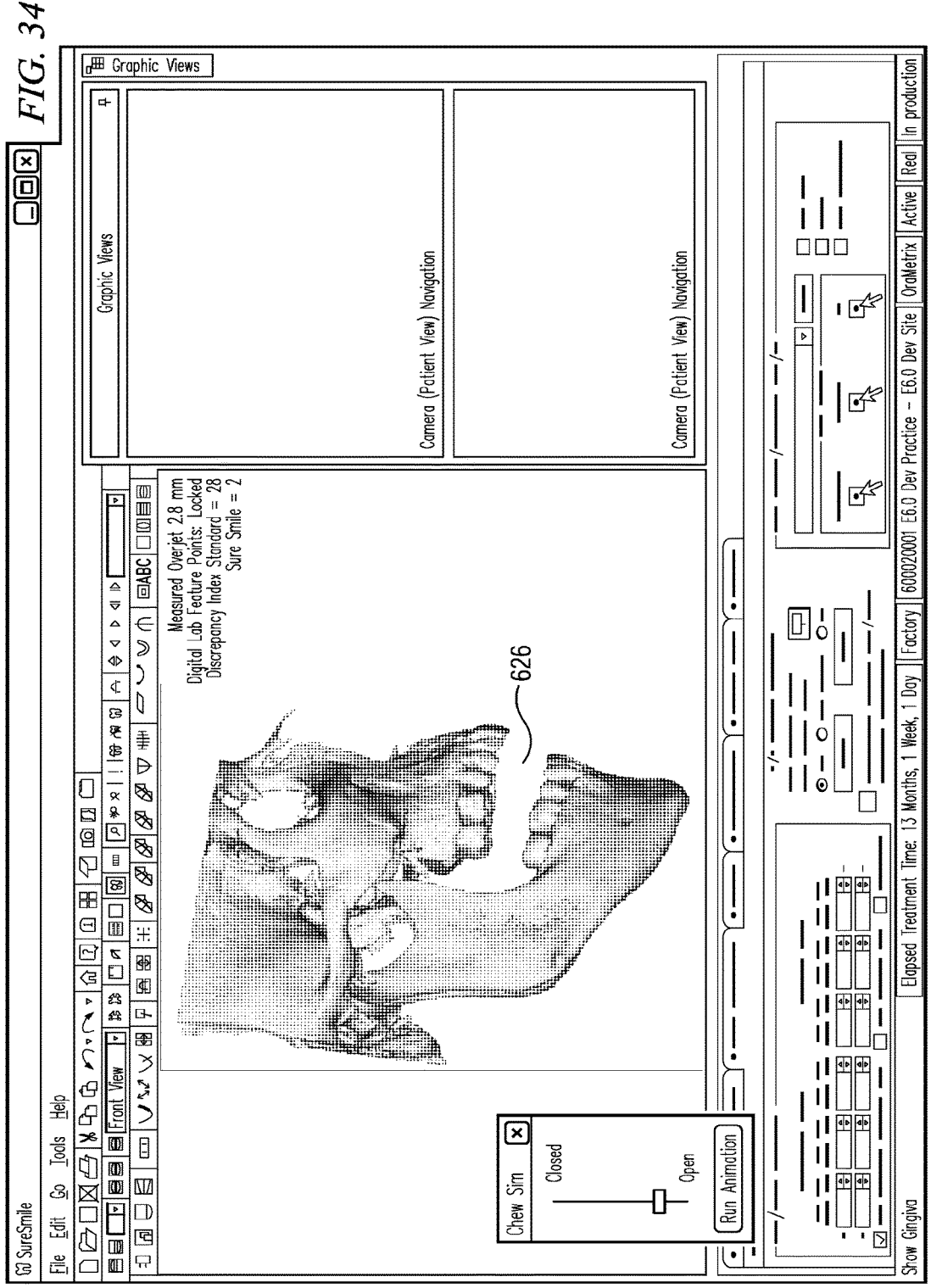

FIG. 34 also shows from the right bucal view bite 626 in a further open position compared to the bite in FIG. 33, along with the facial and jaw bone structures of the patient. Form the volume scan data, it is possible to identify the portion of the jaw bone which functions like a hinge for moving the jaw; and thereby simulate the movement of the jaws.

Figure 35:
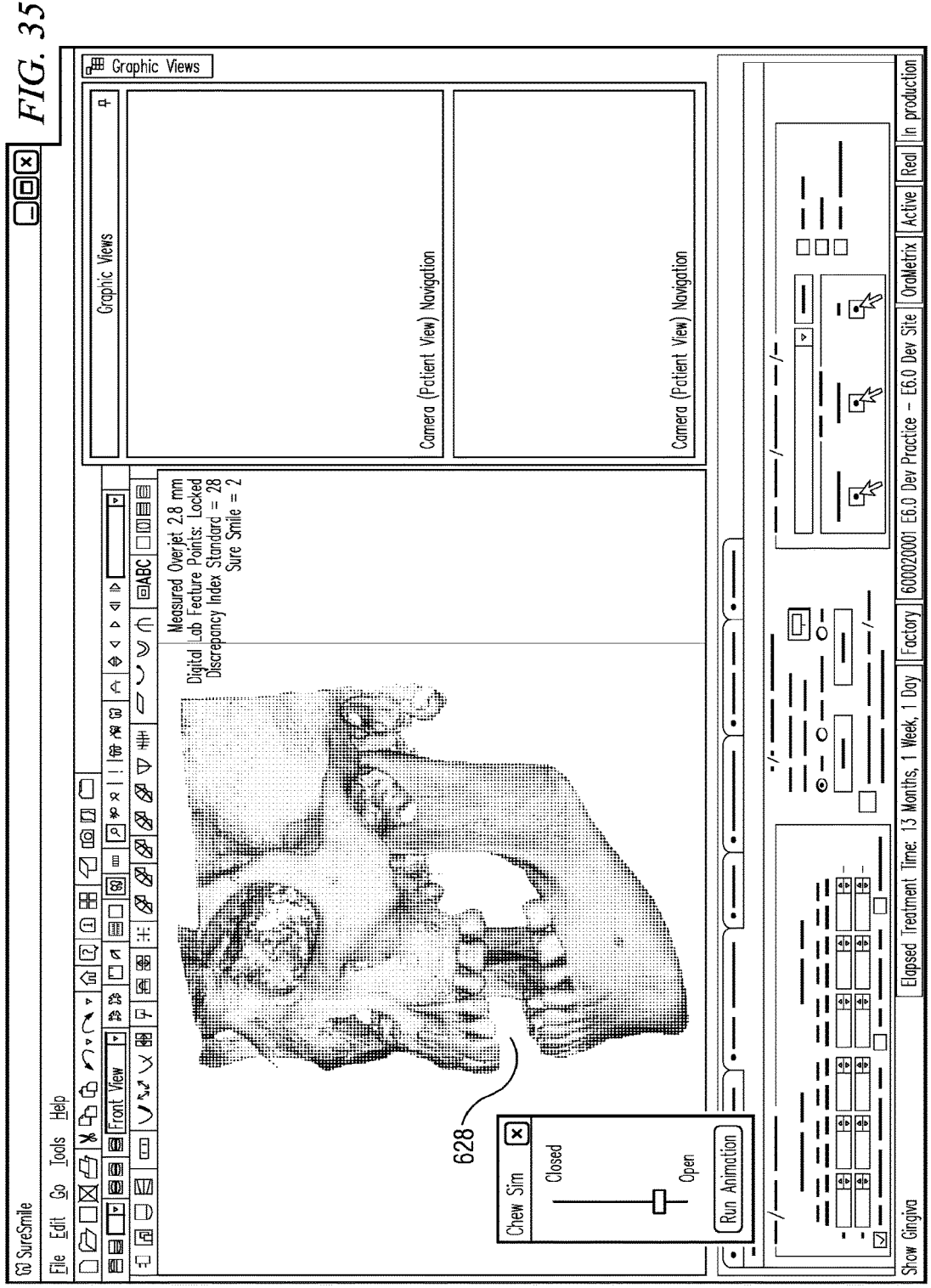

FIG. 35 shows a snap shot of the bite simulation 628 from the left bucal view.

Figure 36A:
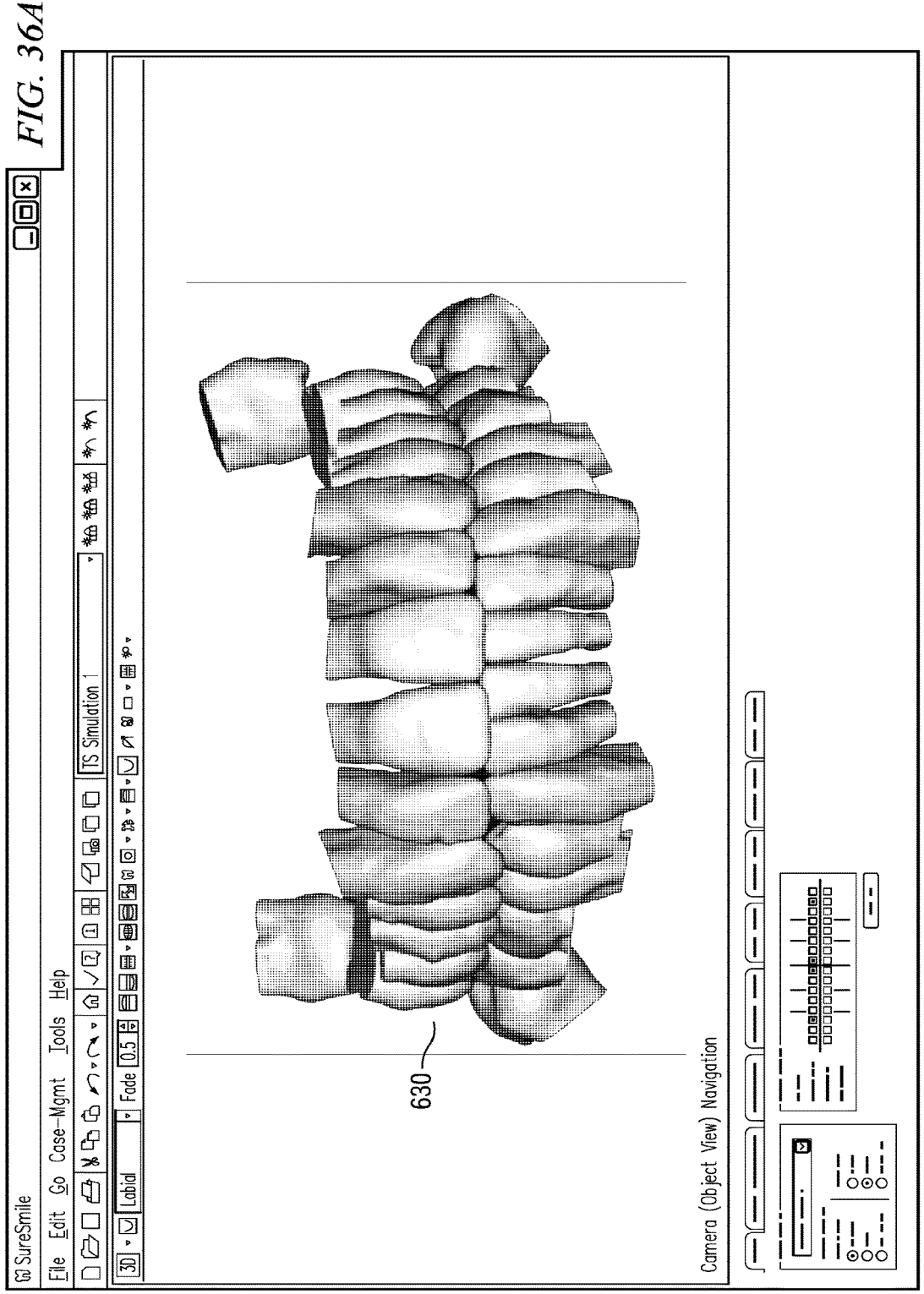
FIGS. 36A-36T show planning movement of one or more teeth including crowns and roots along with soft tissue, e.g., gingiva, and bone in order to realize the desired objectives.
Figure 36B:
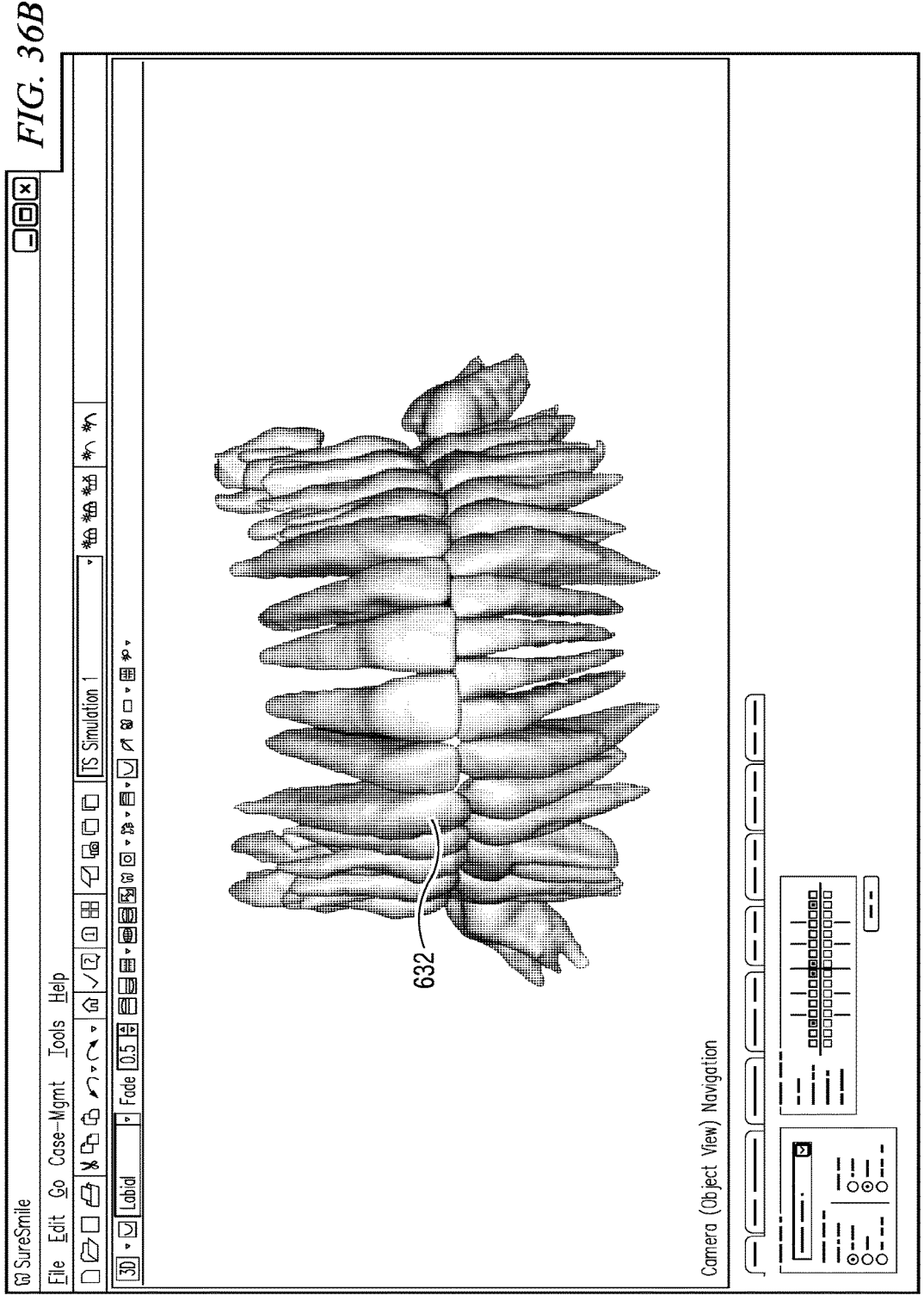
FIG. 36B shows patient's crowns with roots.
Figure 36C:
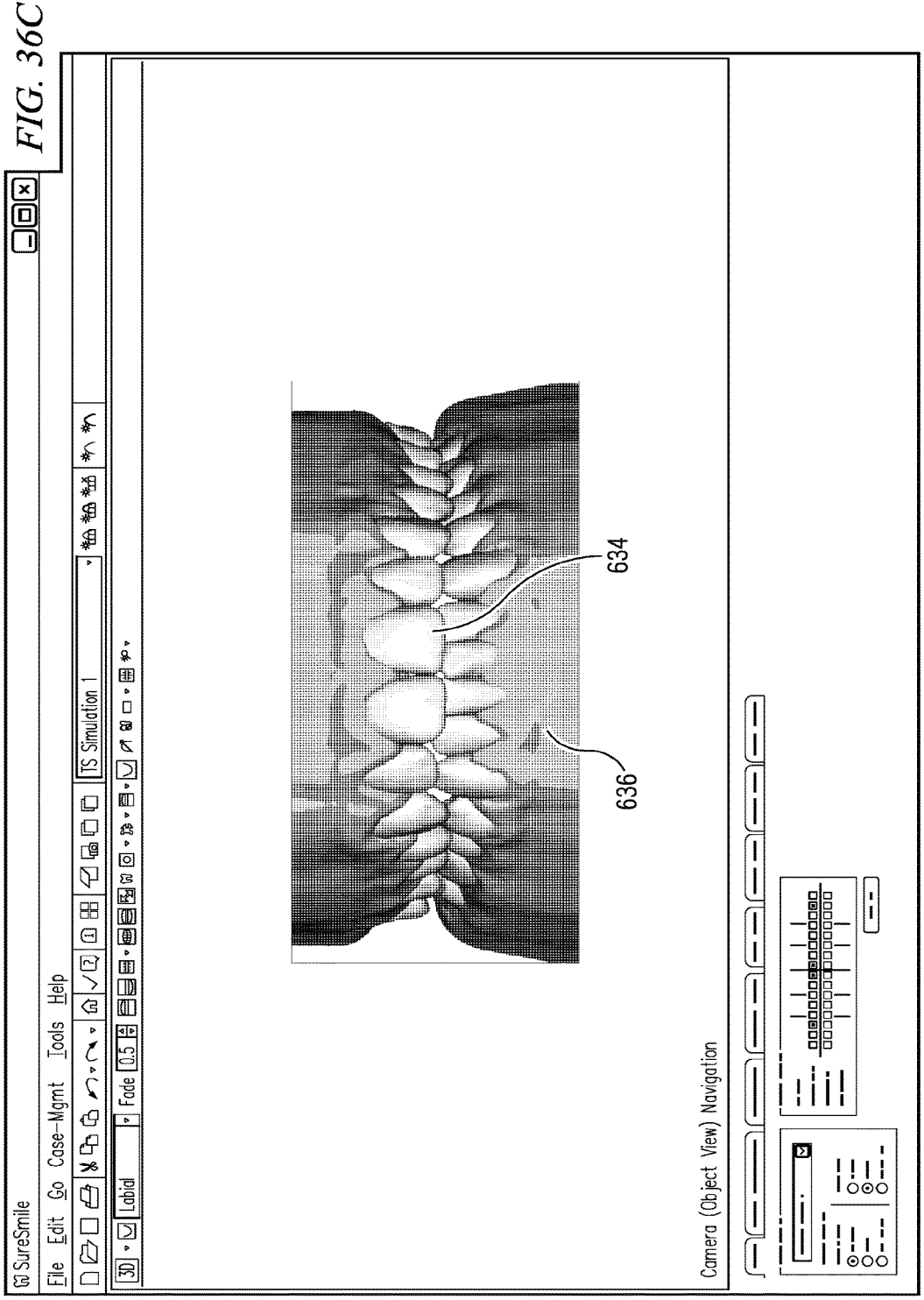
FIG. 36C shows patient's crowns and gingiva. Roots are hidden behind the gingiva and the bone.
Figure 36D:
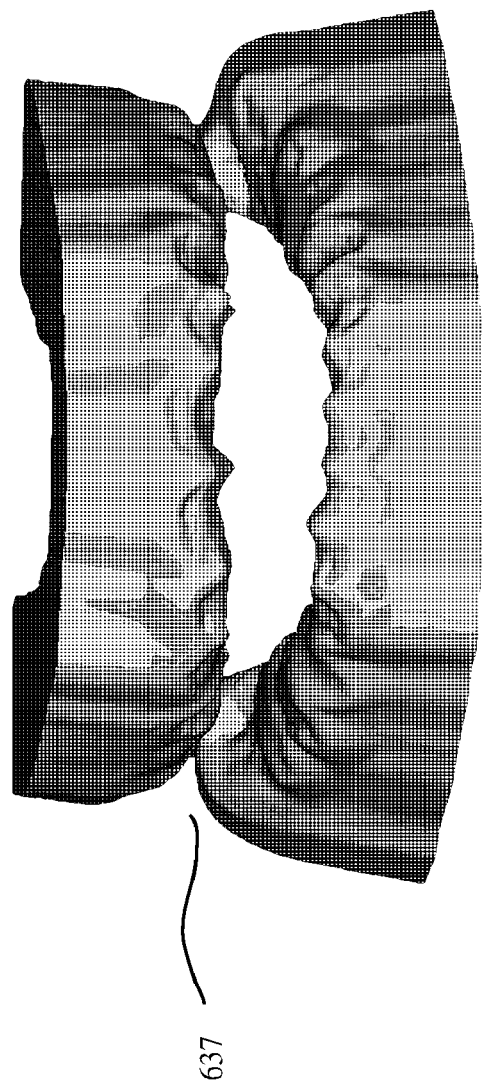
FIG. 36D shows 3-D isolated image of the gingival tissue.
Figure 36E:
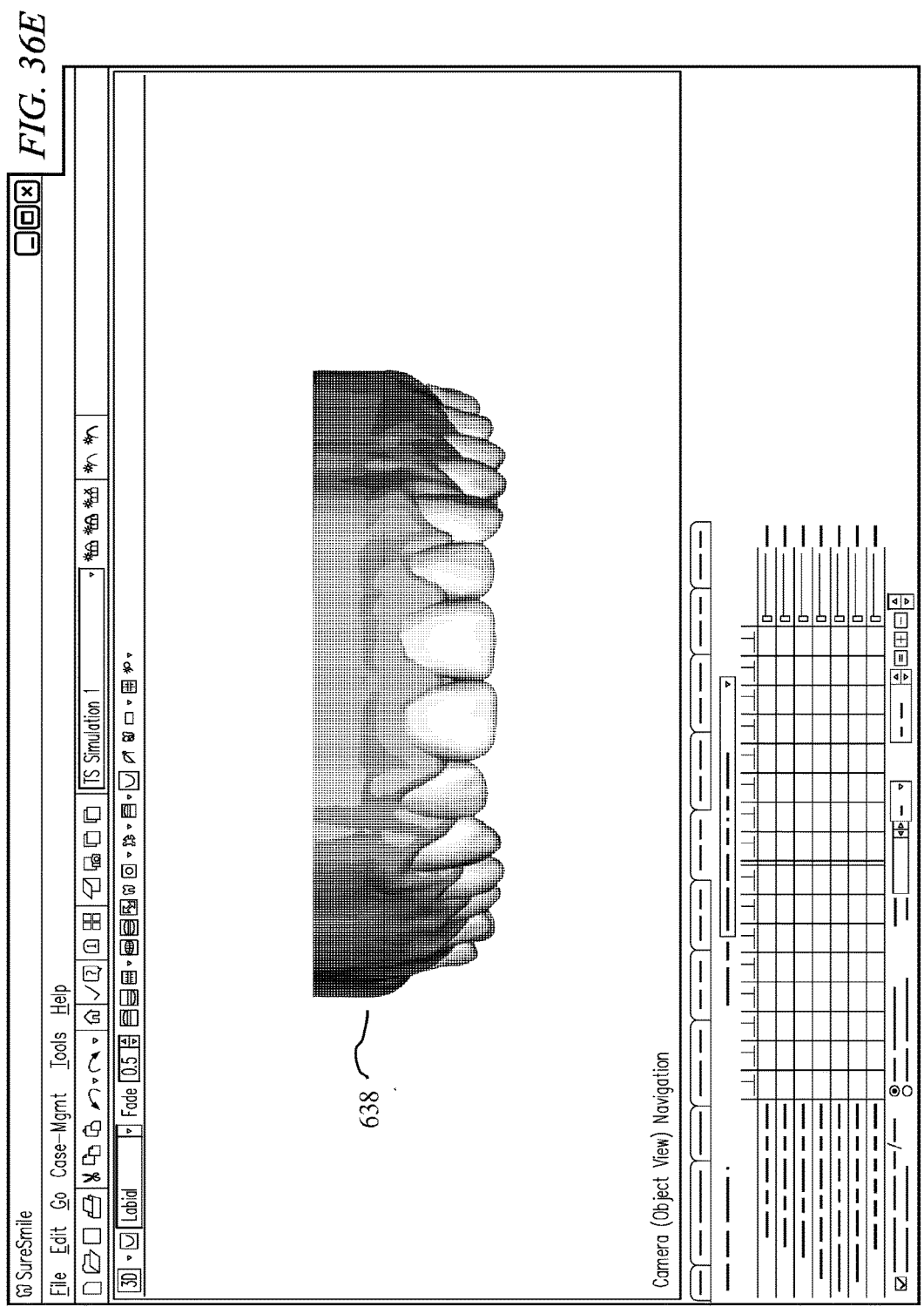
FIG. 36E shows image of the upper arch with teeth and roots hidden behind the gingival tissue and bone. Also bone is hidden by the gingival tissue.
Figure 36F:
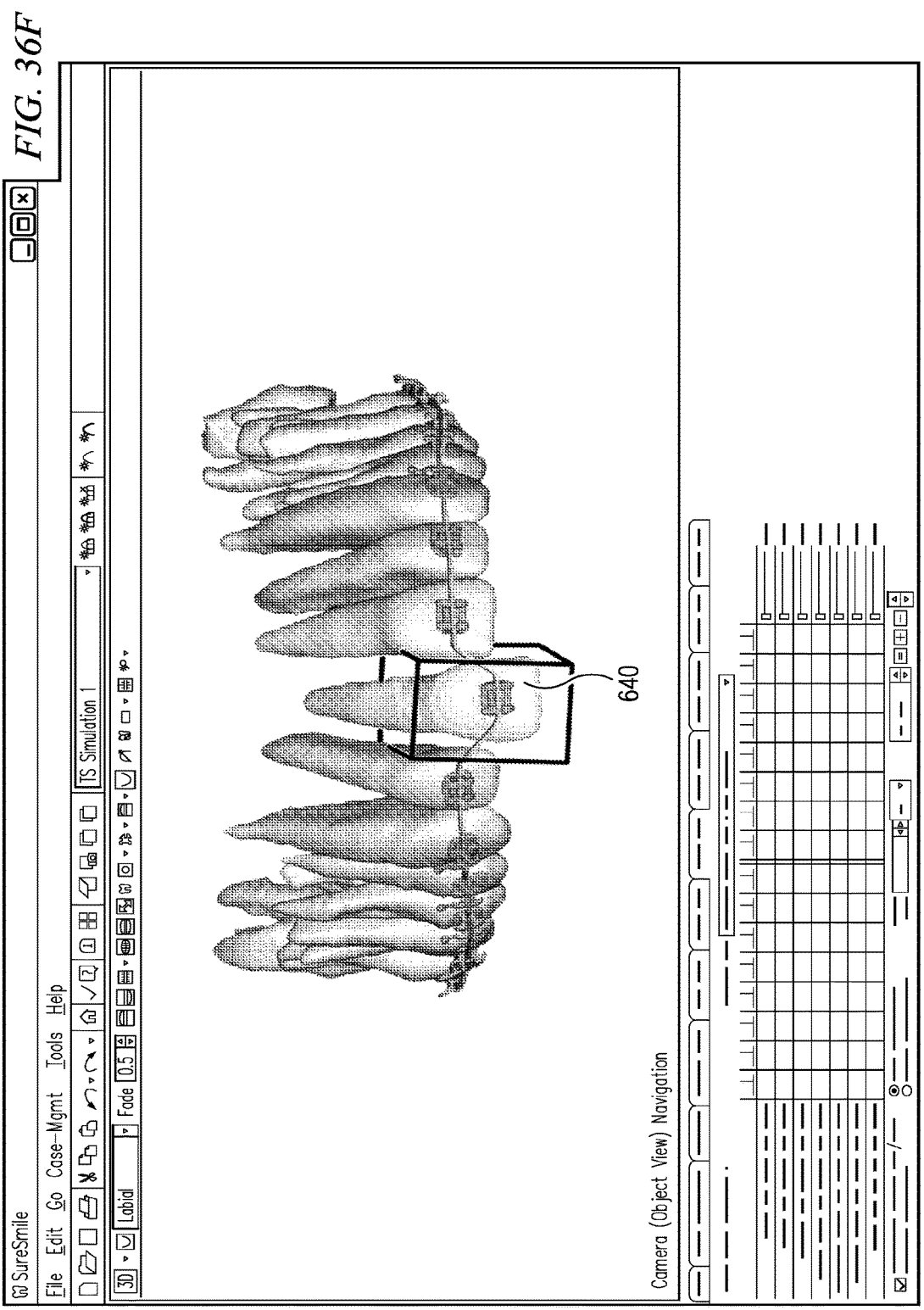
FIG. 36F shows appliances on patient's teeth and one tooth being extruded. The tooth has moved 4 mm.
Figure 36G:
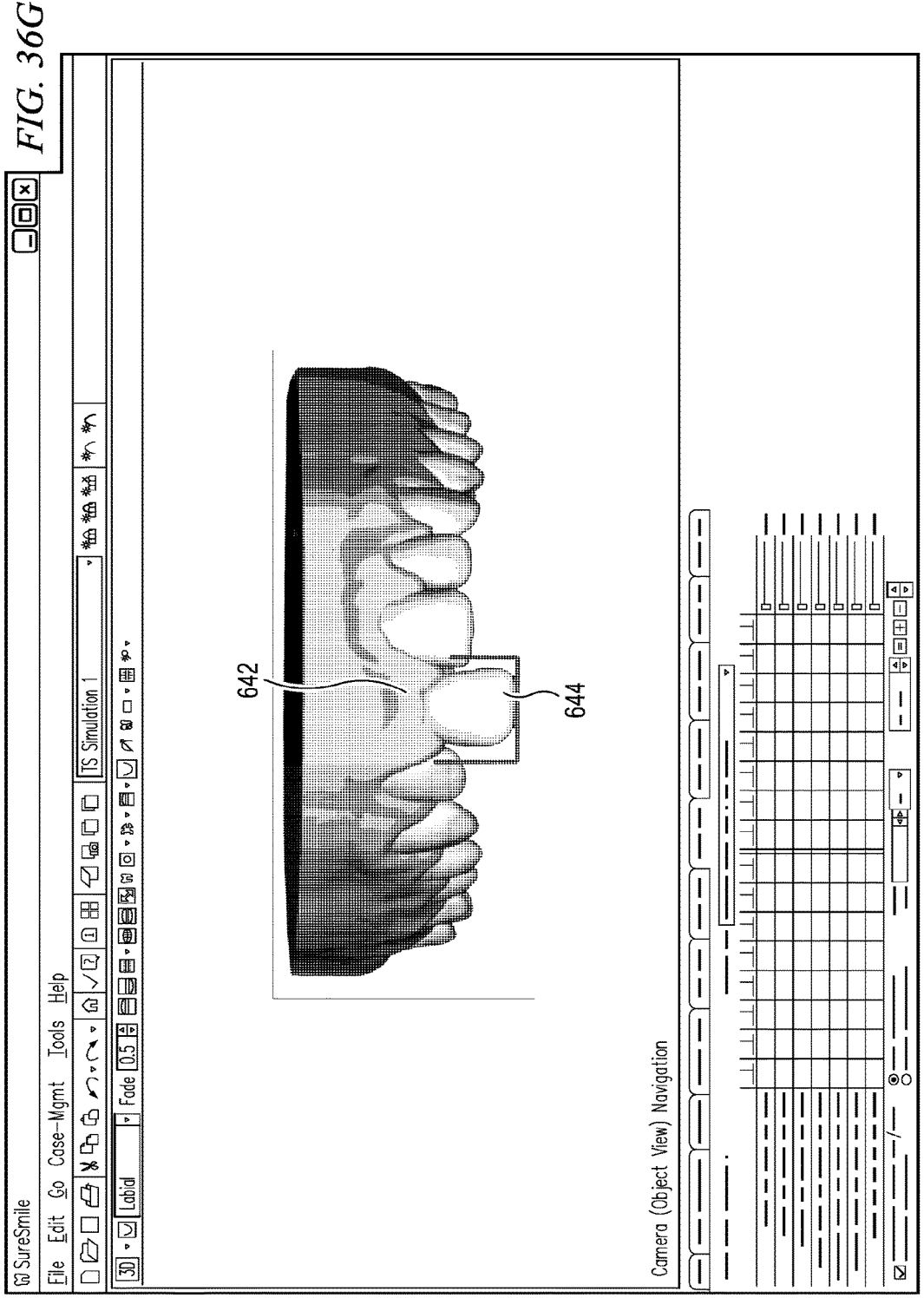
FIG. 36G shows simulation of gingival tissue as the tooth comes down. Note the gingival tissue follows tooth movement.
Figure 36H:
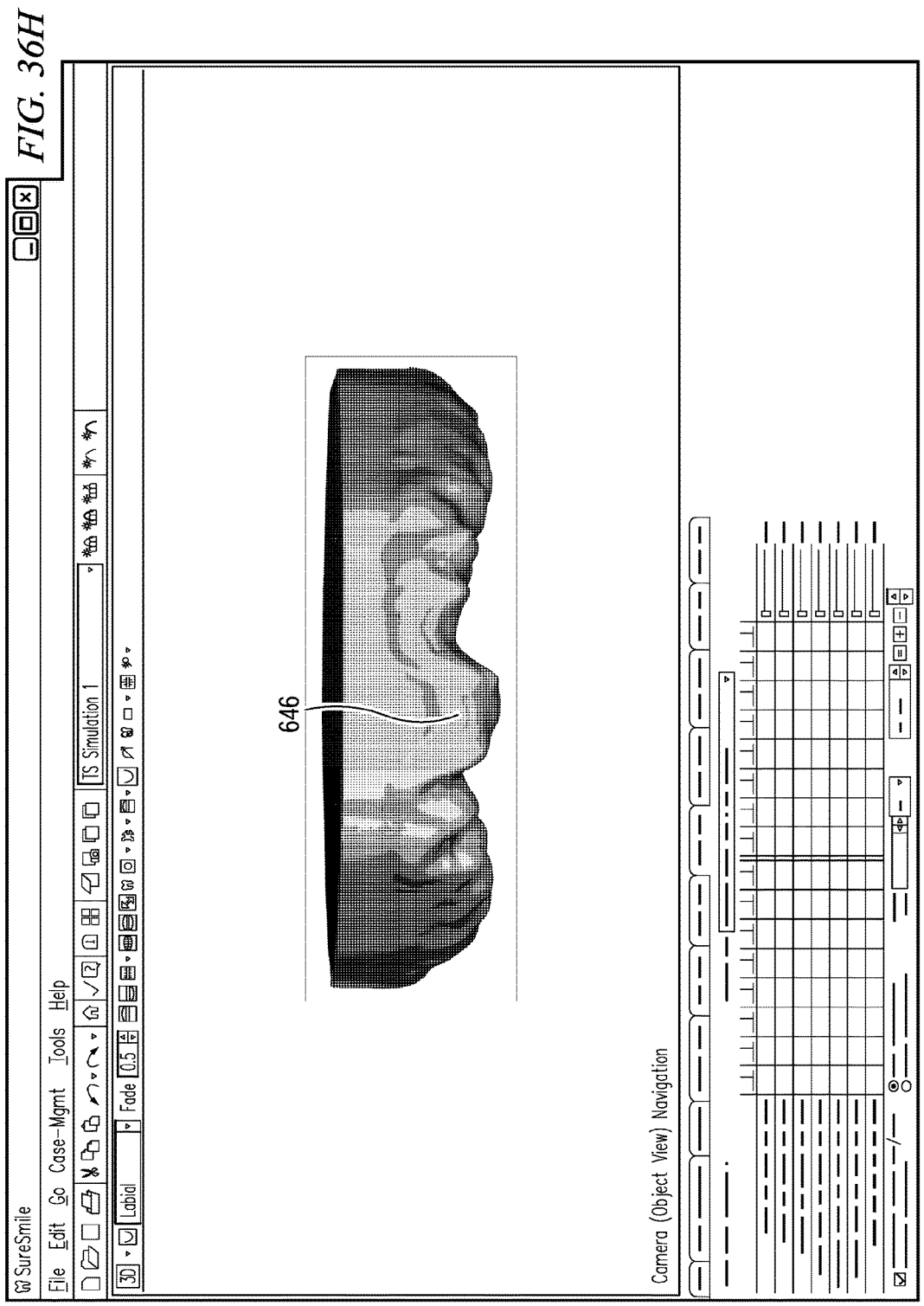
FIG. 36H shows change in architecture of gingival tissue as a result of the tooth movement.
Figure 36I:
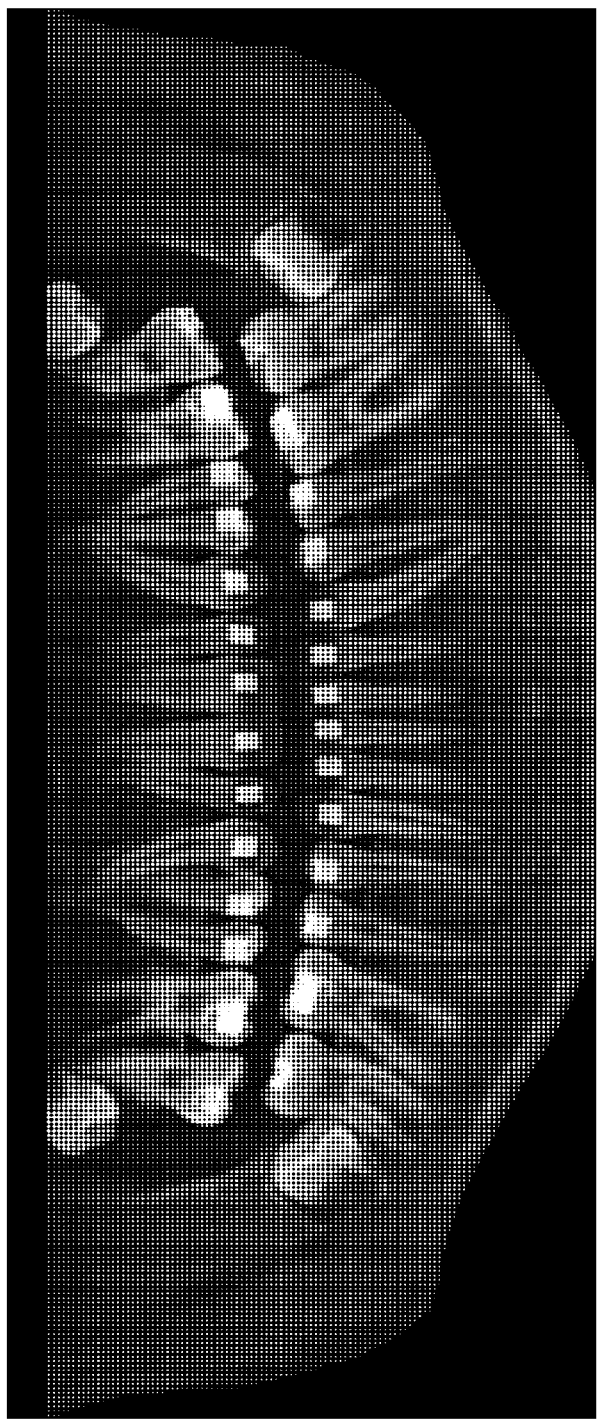
FIG. 36I shows a 2-D panorex X-ray view of a patient's teeth with roots and brackets.
Figure 36J:
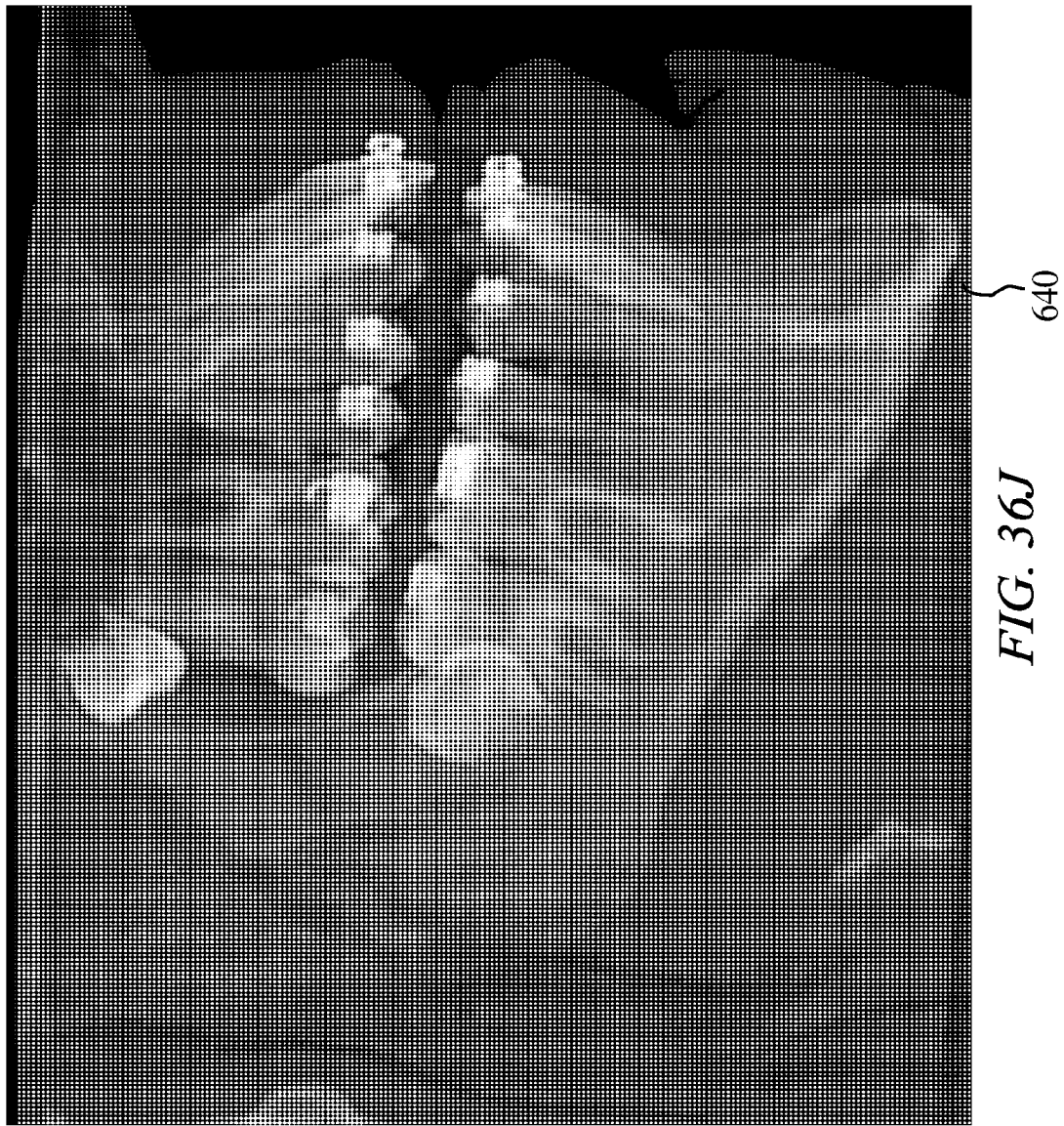
FIG. 36J shows a 2-D ceph X-ray view of a patient's teeth with roots and brackets.
Figure 36K:
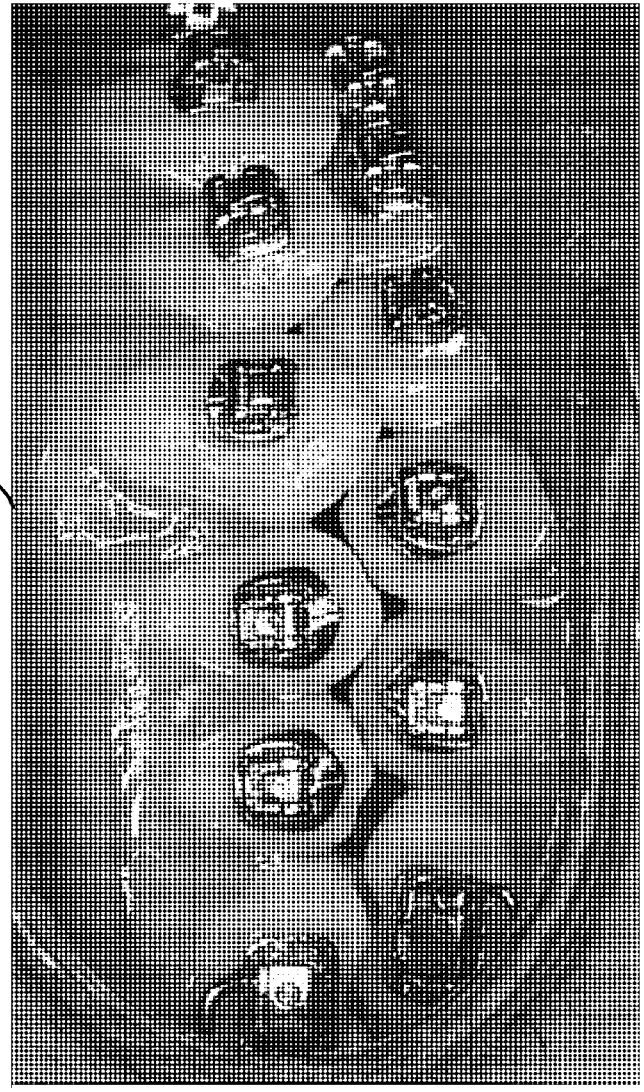
FIG. 36K shows 2-D photo of a patient's tooth crown, gum tissue and brackets.
Figure 36L:
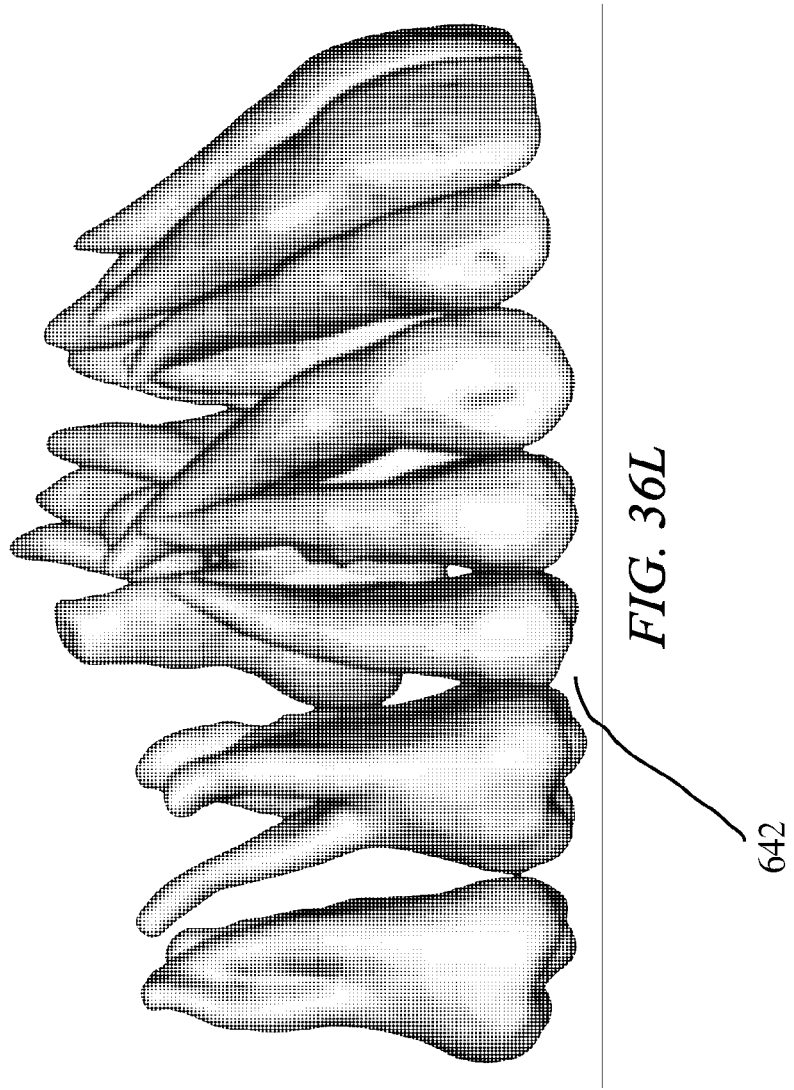
FIG. 36L shows a 3-D view of the same teeth with roots but without gum tissue and bone.
Figure 36M:
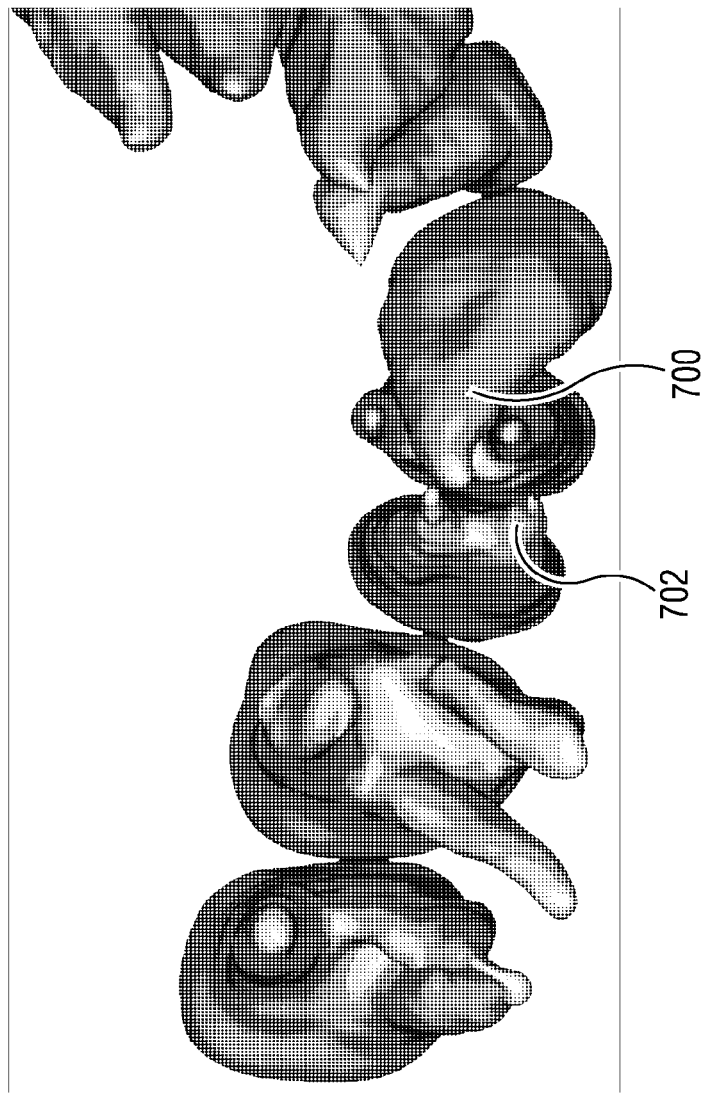
FIG. 36M shows a 3-D top view of the same teeth with roots but without gum tissue and bone. Note the root of the canine is trapped between the roots of the first premolar. This is unobservable in 2-D views.
Figure 36N:
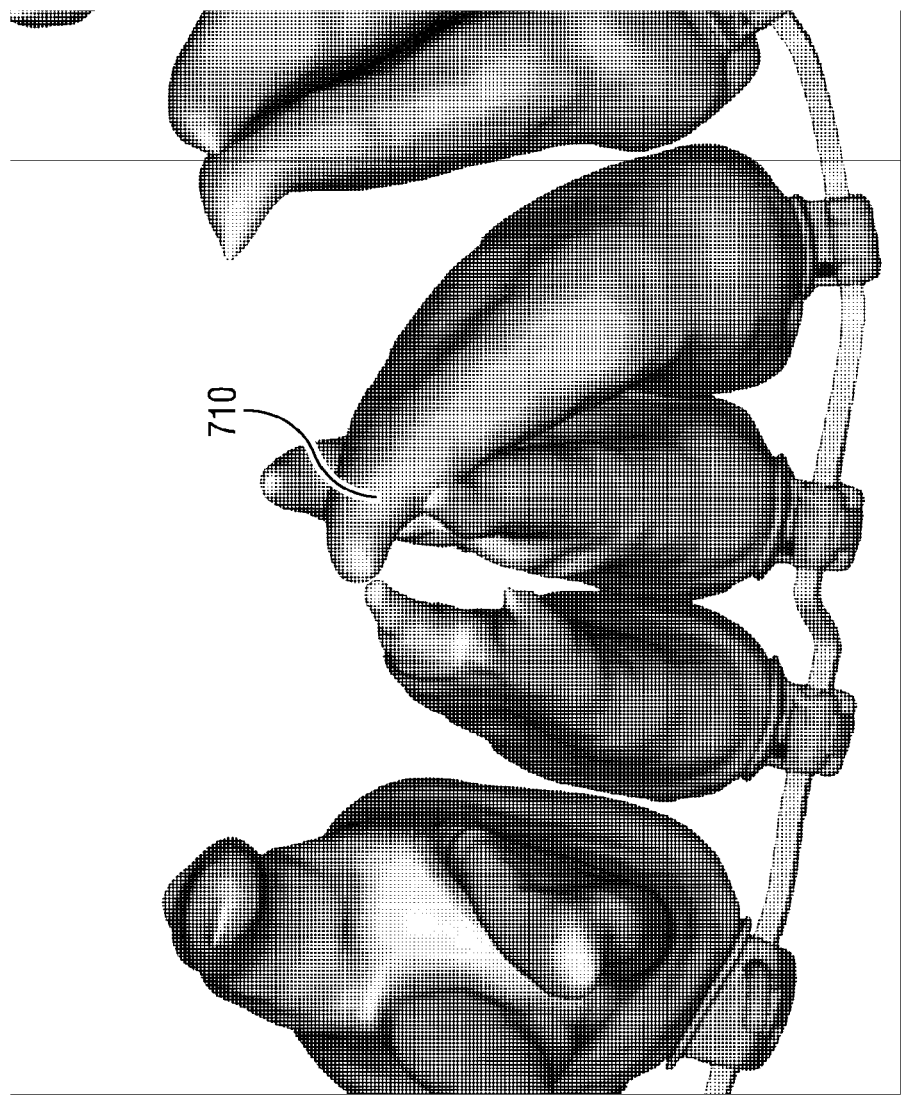
FIG. 36N shows that if the tooth movement is not planned correctly without considering the location of roots in 3-D space root collision may occur causing root resorption as shown.
Figure 36O:
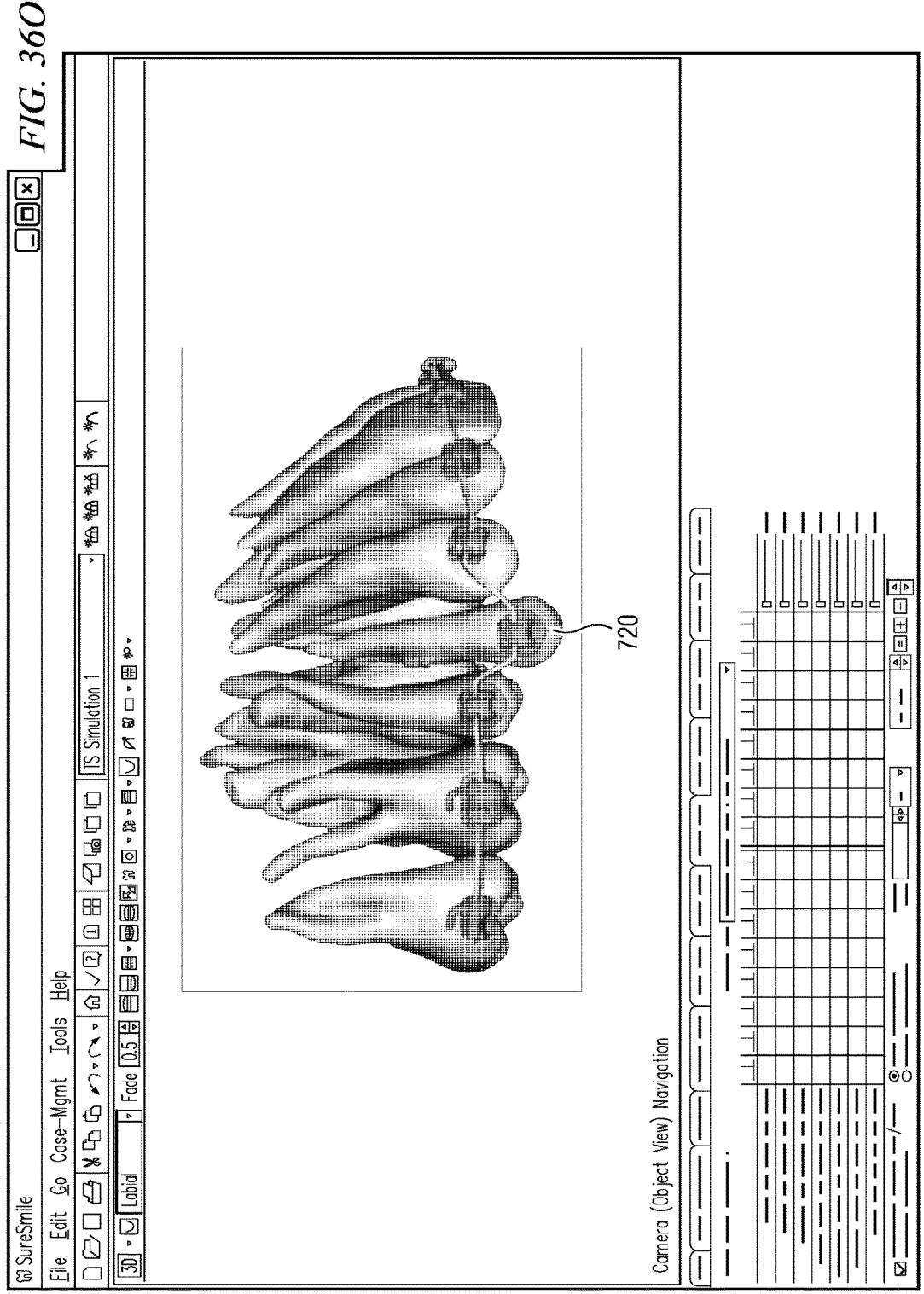
FIG. 36O shows avoidance of the root collision by planning extrusion of the first bicuspid.
Figure 36P:
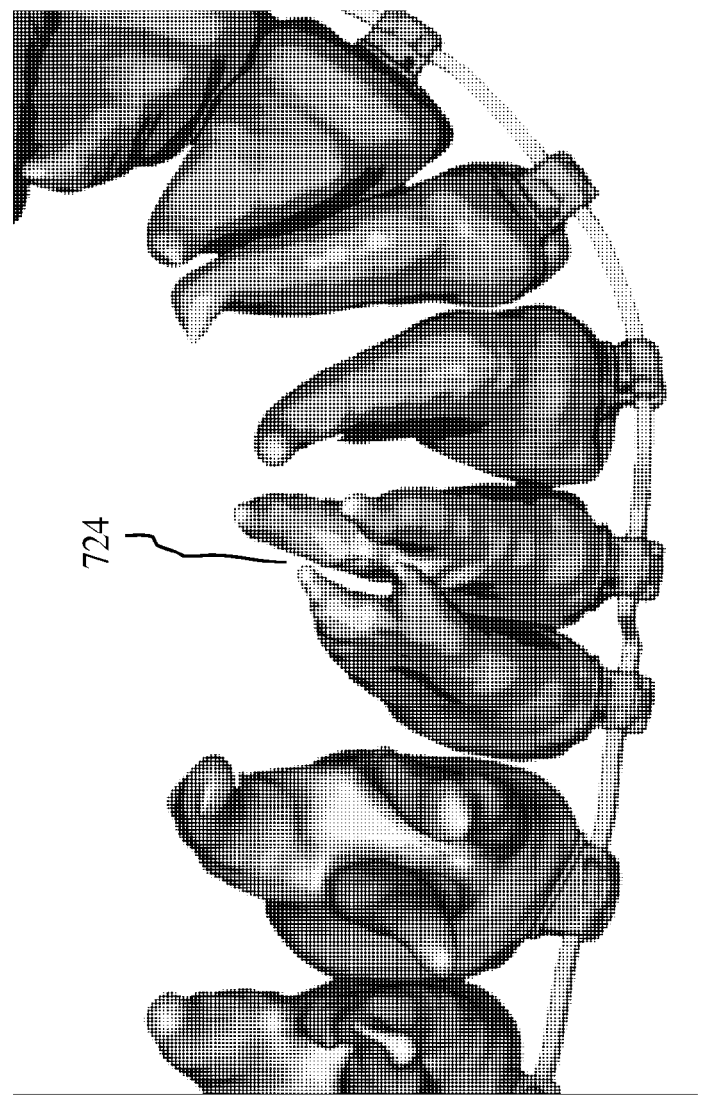
FIG. 36P shows avoidance of the root collision by proper planning of tooth and root movement in 3-D space.
Figure 36Q:
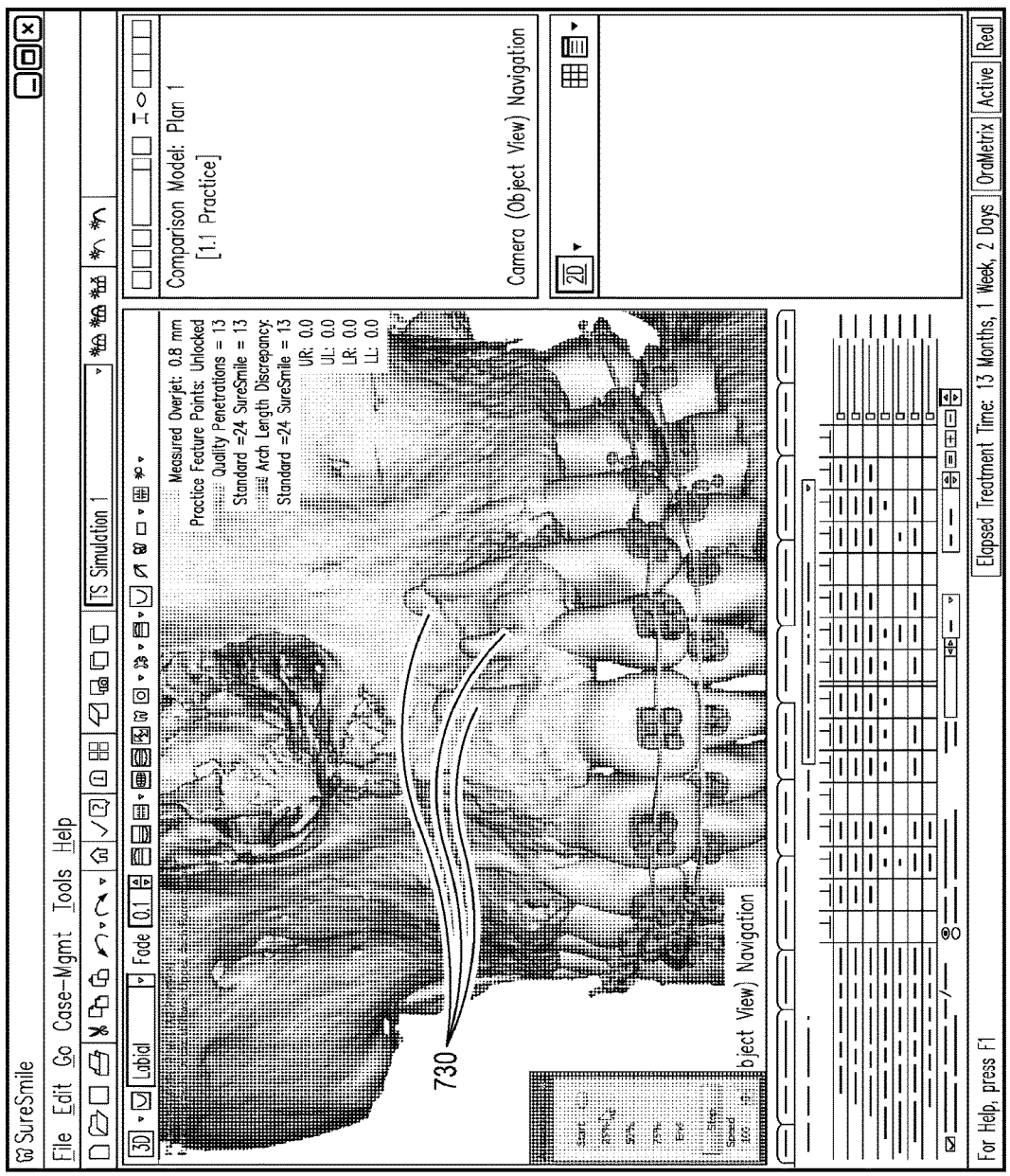
FIG. 36Q shows roots out of bone on a volumetric image.
Figure 36R:
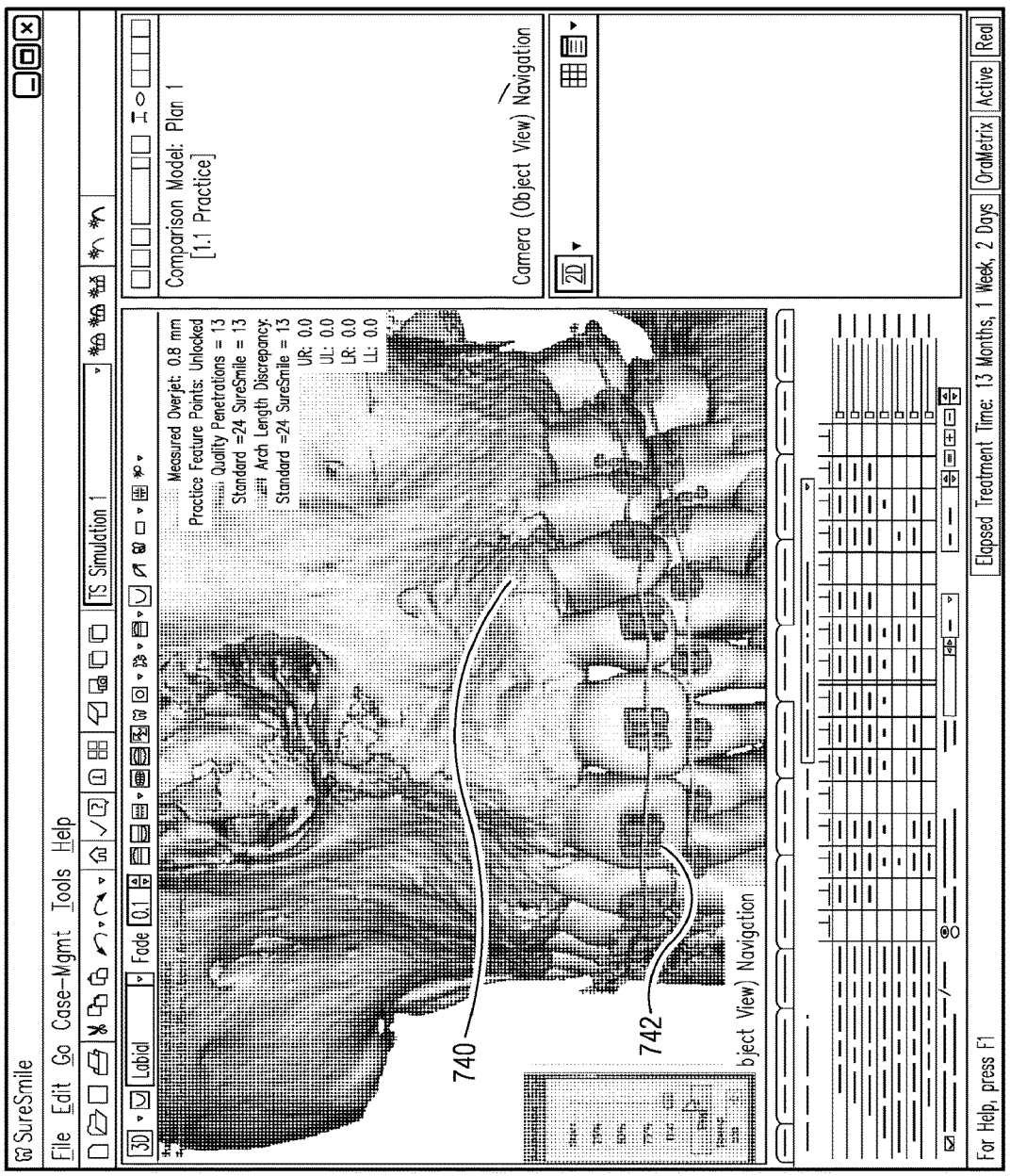
FIG. 36R shows the movement of the roots bringing them inside the bone to gain more support for the tooth; and the appliance designed to achieve it.
Figure 36S:
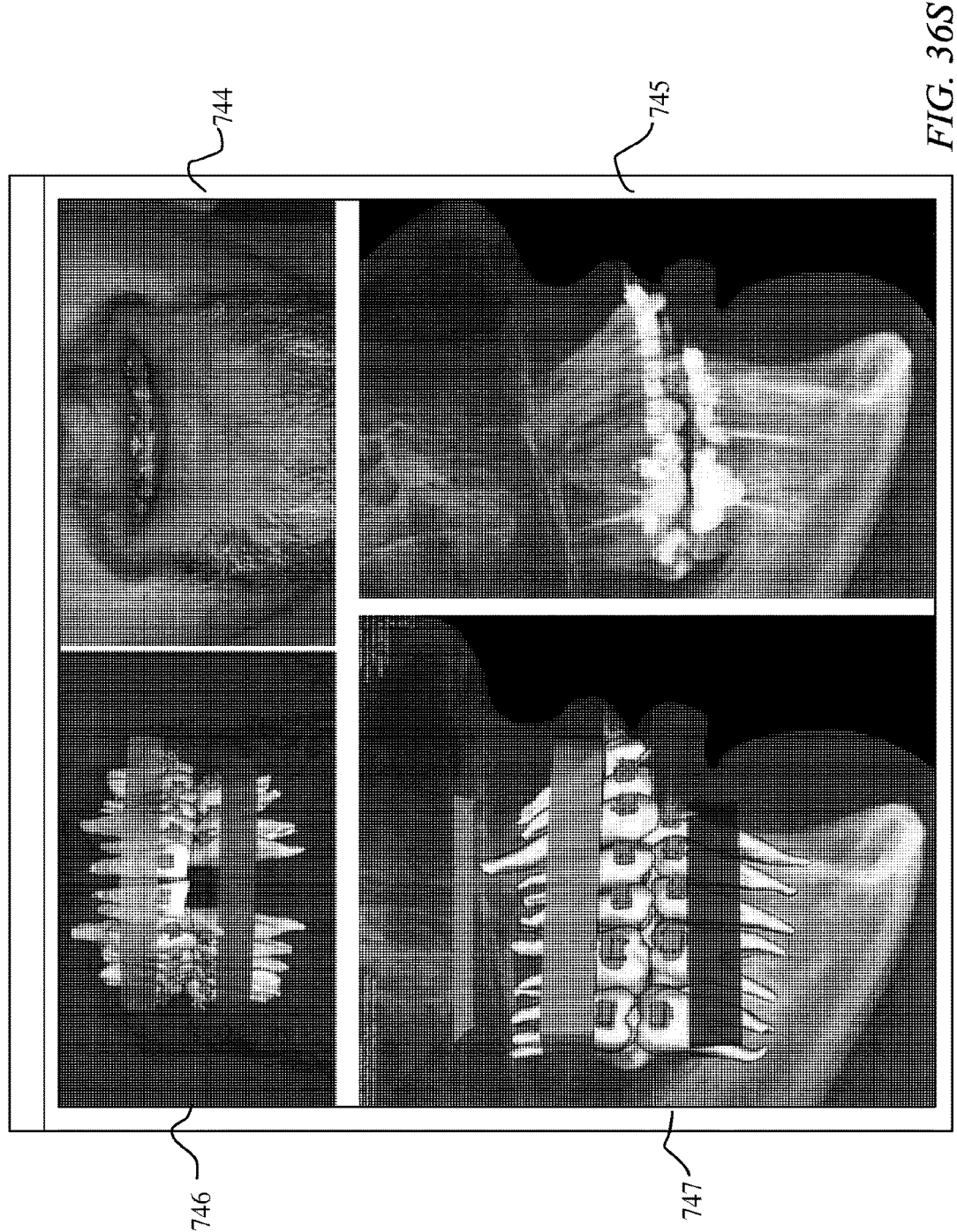
FIG. 36S shows planning of bone movement for surgery with appropriate 2-D and 3-D images and composites.
Figure 36T:
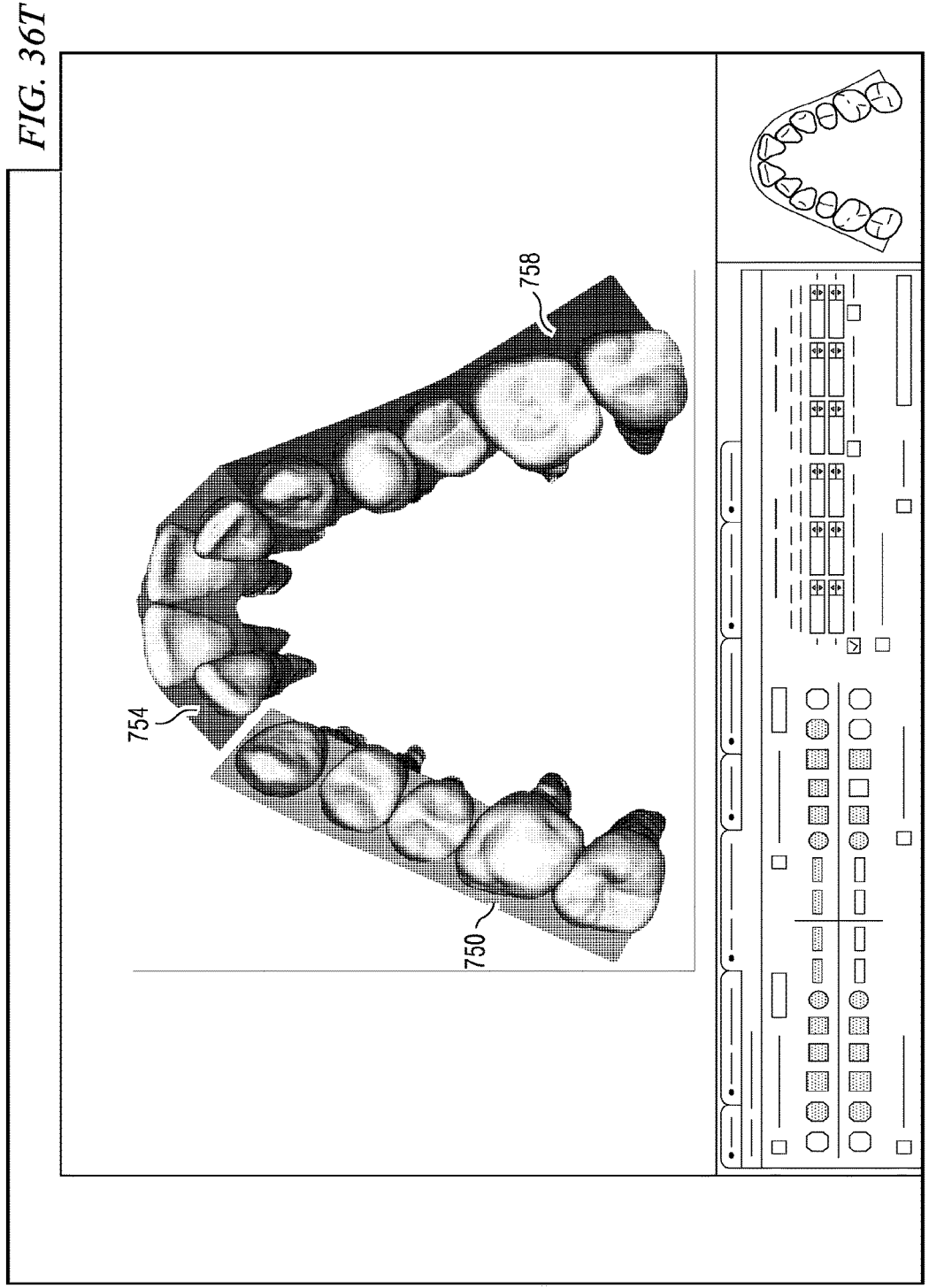

FIGS. 36A-36T show planning movement of one or more teeth including crowns and roots along with soft tissue, e.g., gingiva, and bone in order to realize the desired objectives. Another preferred embodiment of the invention discloses a method of orthodontic treatment planning for a patient having tooth-roots abnormalities, using a workstation having a processing device, a storage device, and an user interface with a display, comprising the steps of:

(a) obtaining a three dimensional virtual model of dentition of the patient; wherein the virtual model of dentition is constructed solely from volume scanned digital images of actual craniofacial and dentition structure of the patient, and comprises the patient's teeth with three-dimensional crowns and three-dimensional roots and three-dimensional upper and lower jaw bones;

(b) identifying the tooth-roots abnormalities; and (c) planning corrective treatment steps to cure the tooth-roots abnormalities.

FIG. 36A shows image of patient's tooth crowns 630.

FIG. 36B shows patient's crowns with roots 632.

FIG. 36C shows patient's crowns 634 and gingiva 636. Roots are hidden behind the gingiva and the bone.

FIG. 36D shows 3-D isolated image 637 of the gingival tissue.

FIG. 36E shows image of the upper arch 638 with teeth and roots hidden behind the gingival tissue and bone. Also bone is hidden by the gingival tissue.

FIG. 36F shows appliances on patient's teeth and one tooth 640 being extruded. The tooth 640 has moved 4 mm.

FIG. 36G shows simulation of gingival tissue 642 as the tooth 644 comes down. Note the gingival tissue follows tooth movement.

FIG. 36H shows change in architecture of gingival tissue 646 as a result of the tooth movement.

FIG. 36I shows a 2-D panorex X-ray view 639 of a patient's teeth with roots and brackets.

FIG. 36J shows a 2-D ceph X-ray view 640 of a patient's teeth with roots and brackets.

FIG. 36K shows 2-D photo 641 of a patient's tooth crown, gum tissue and brackets.

FIG. 36L shows a 3-D view 642 of the same teeth with roots but without gum tissue and bone.

FIG. 36M shows a 3-D top view of the same teeth with roots but without gum tissue and bone. Note the root of the canine 700 is trapped between the roots of the first premolar 702. This is unobservable in 2-D views.

FIG. 36N shows that if the tooth movement is not planned correctly without considering the location of roots in 3-D space root collision 710 may occur causing root resorption as shown.

FIG. 36O shows avoidance of the root collision by planning extrusion of the first bicuspid 720.

FIG. 36P shows avoidance of the root collision 724 by proper planning of tooth and root movement in 3-D space.

FIG. 36Q shows roots 730 out of bone on a volumetric image.

FIG. 36R shows the movement of the roots 740 bringing them inside the bone to gain more support for the tooth; and the appliance 742 designed to achieve it.

FIG. 36S shows planning of bone movement for surgery with appropriate 2-D and 3-D images 744, 745 and composites 746, 747.

FIG. 36T shows the upper occlusal surfaces of the teeth and their roots below, three segments 750, 754 and 758 to plan for 3 piece maxillary surgery have been selected. The upper right segment has been expanded and its displacement value shown. Any number of segments can be chosen, and the site of the ostetotmy can be defined if the roots fall in to the ostetotmy site their movement can be planned pre-surgically away from the resection site to avoid damage. The segments can be moved in all three planes of space.

Figure 37A:
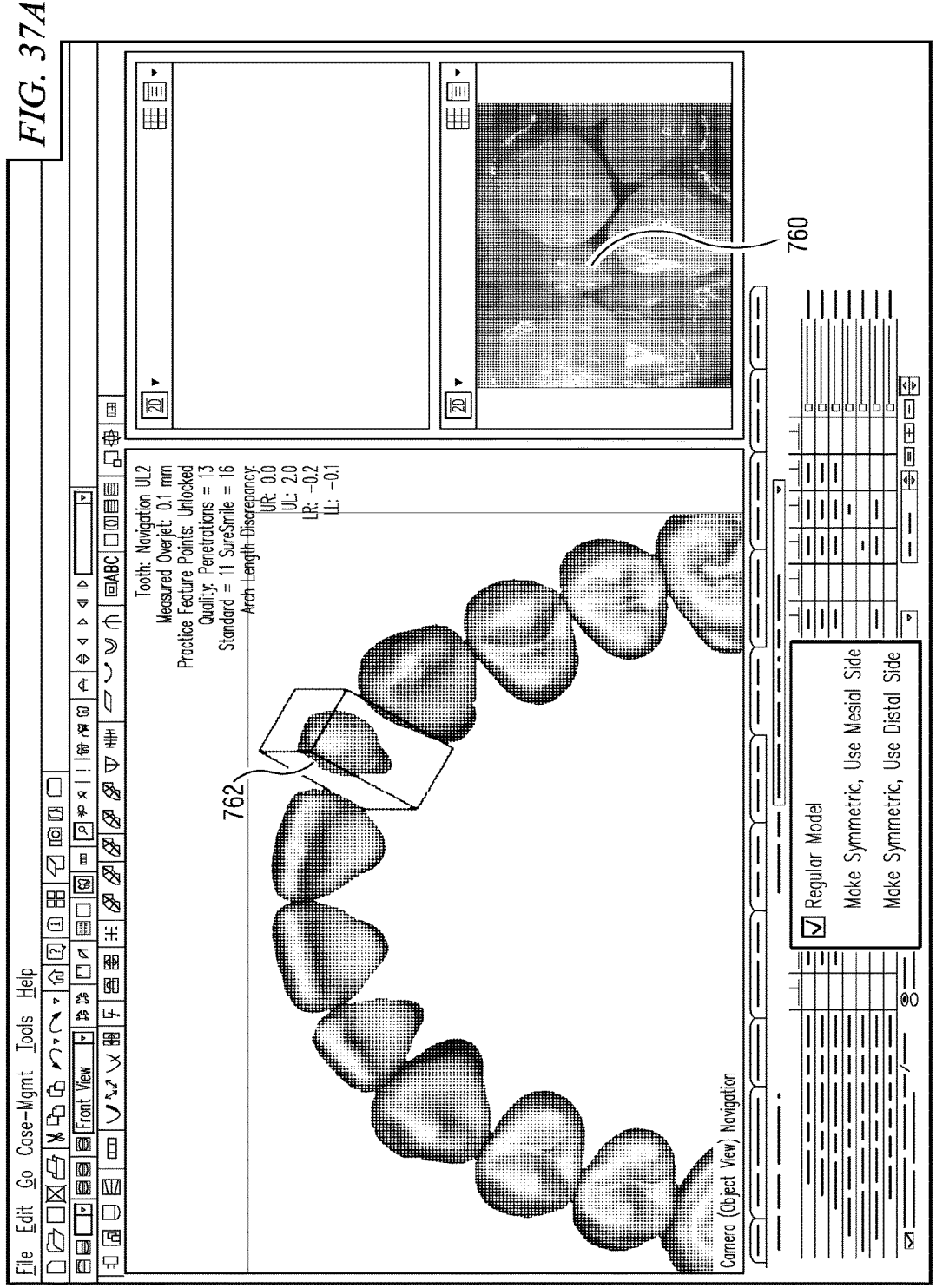
FIGS. 37A-37N show planning of tooth shape and form and restorations with and without orthodontic treatment to achieve maximum aesthetics as efficiently as possible.
Figure 37B:
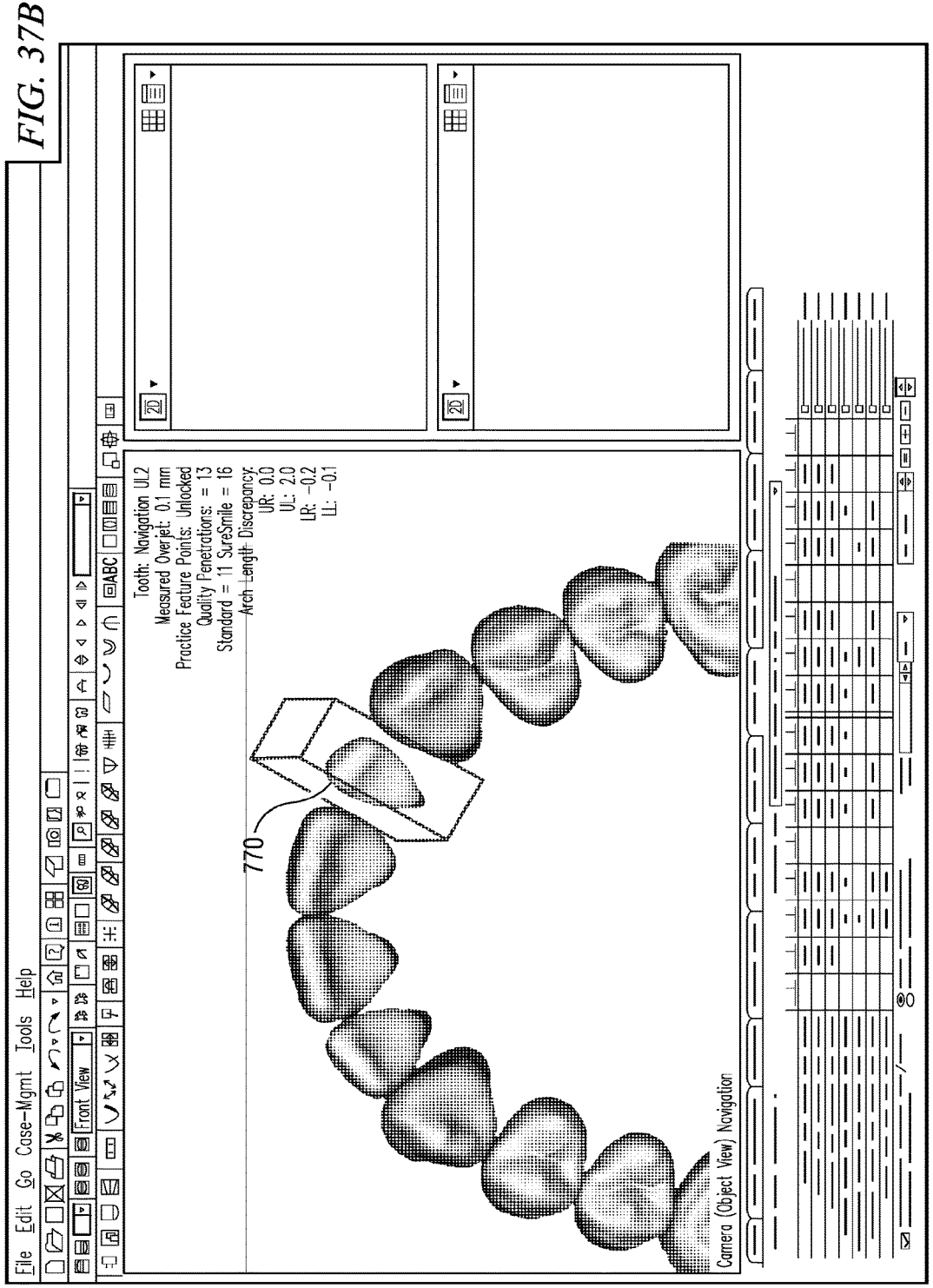
FIG. 37B shows planning to close the space on either side by restoring the tooth on either side by 1 mm.
Figure 37C:
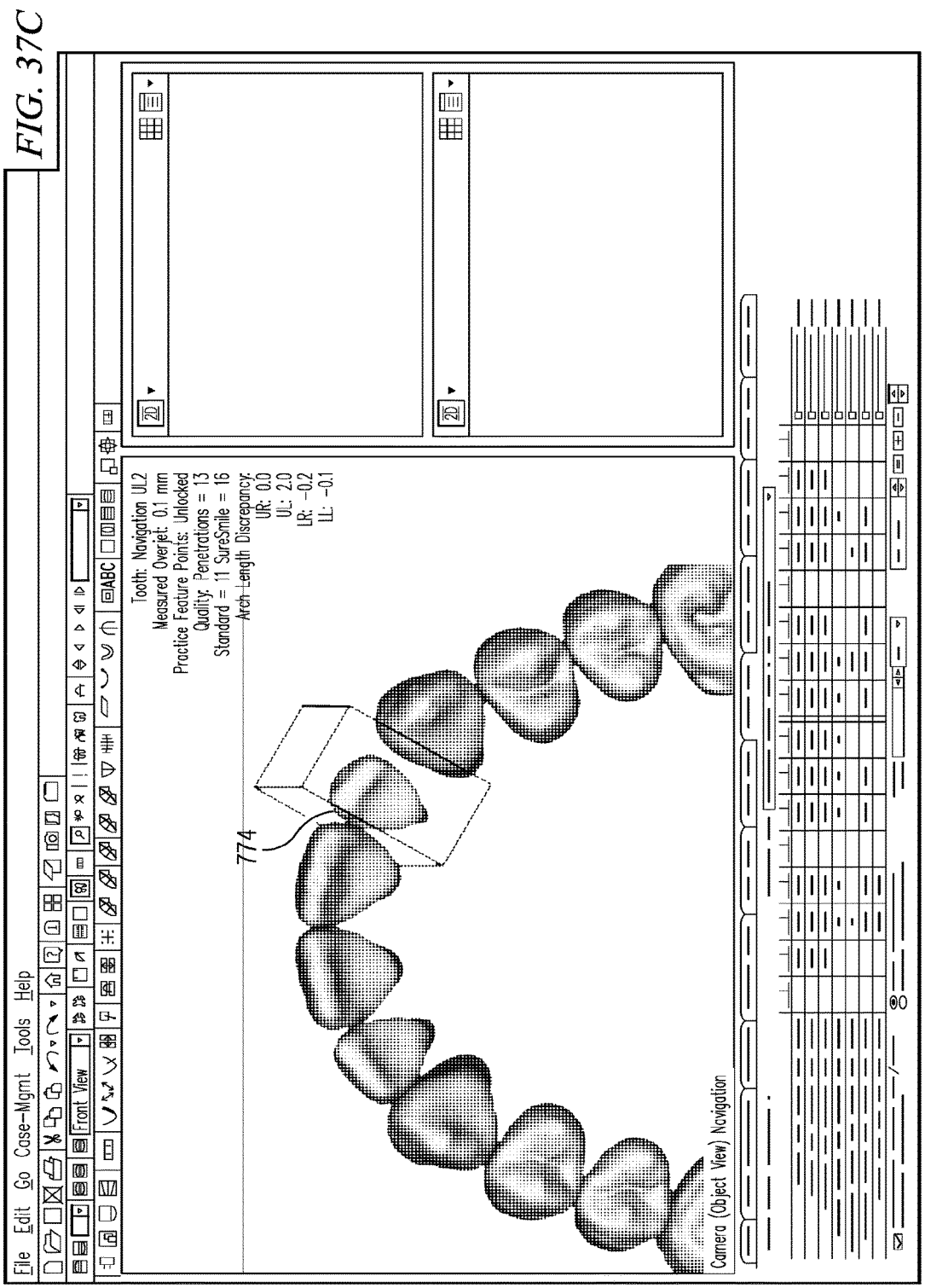
FIG. 37C shows that one side of the tooth has been restored to close the space and achieve normal tooth form.
Figure 37D:
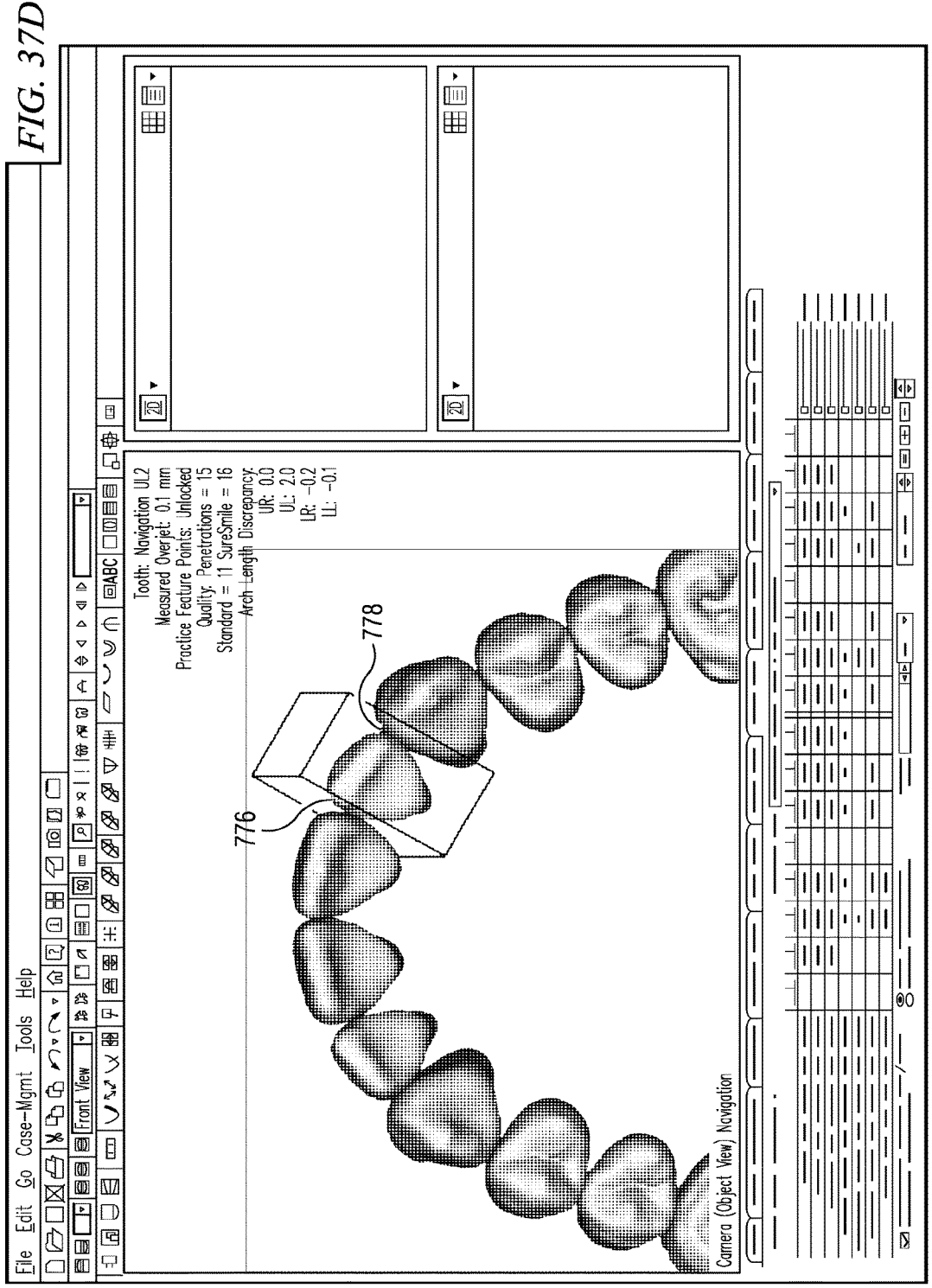
FIG. 37D shows that both sides of the tooth have been restored to close the space and achieve normal tooth form.
Figure 37E:
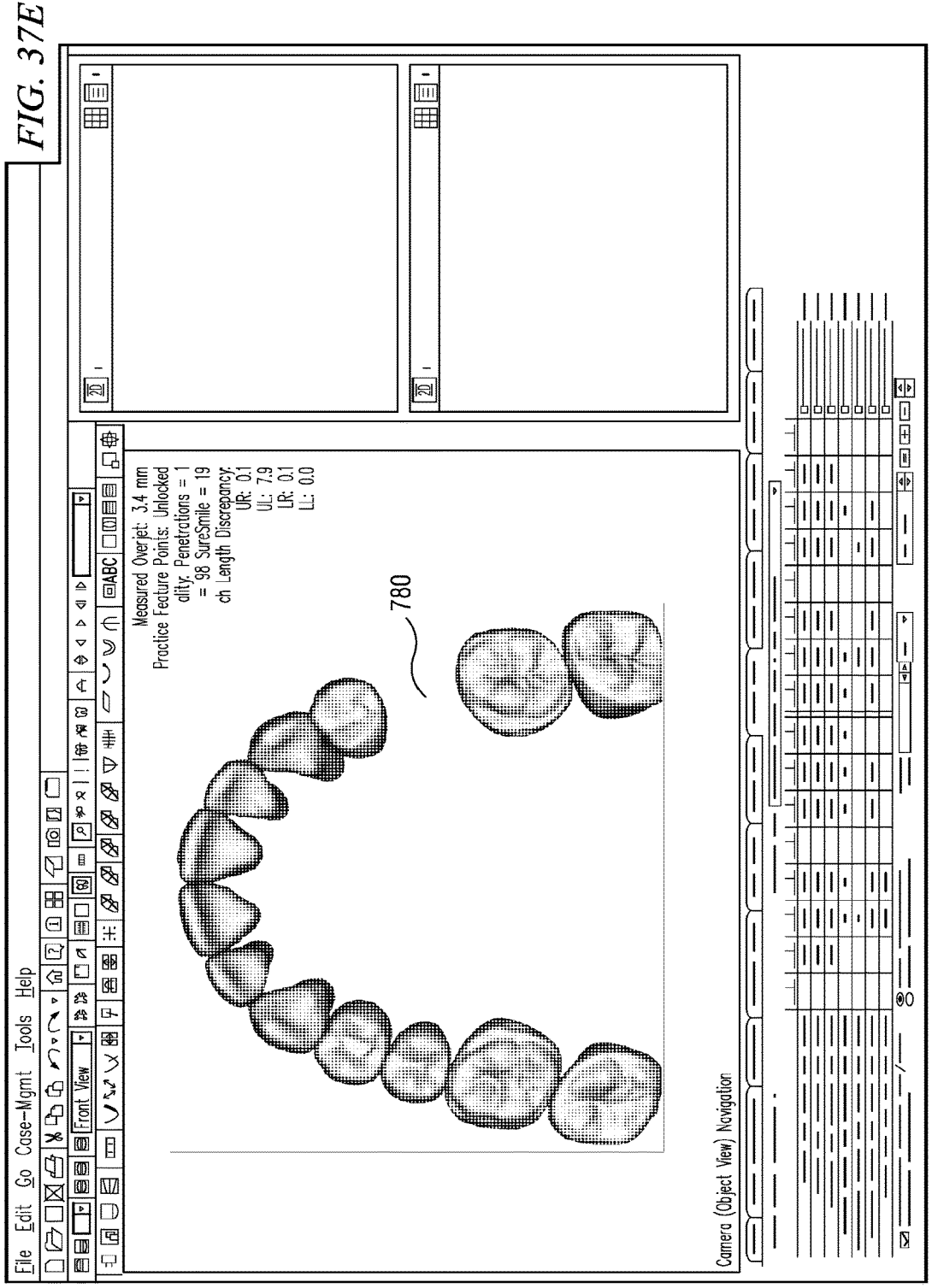
FIG. 37E shows missing second bicuspid tooth.
Figure 37F:
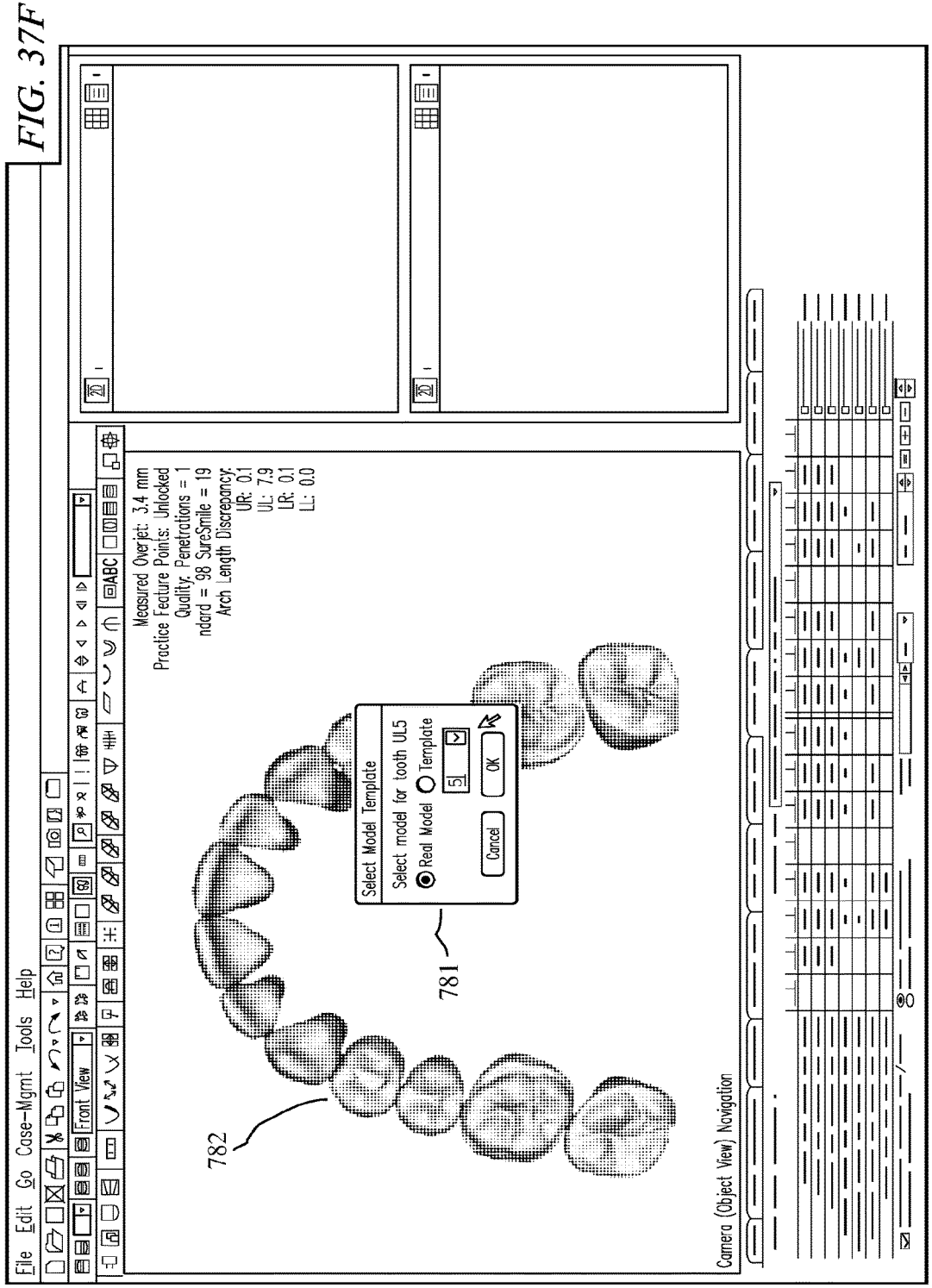
FIG. 37F shows dialogue box to select appropriate tooth to close space.
Figure 37G:
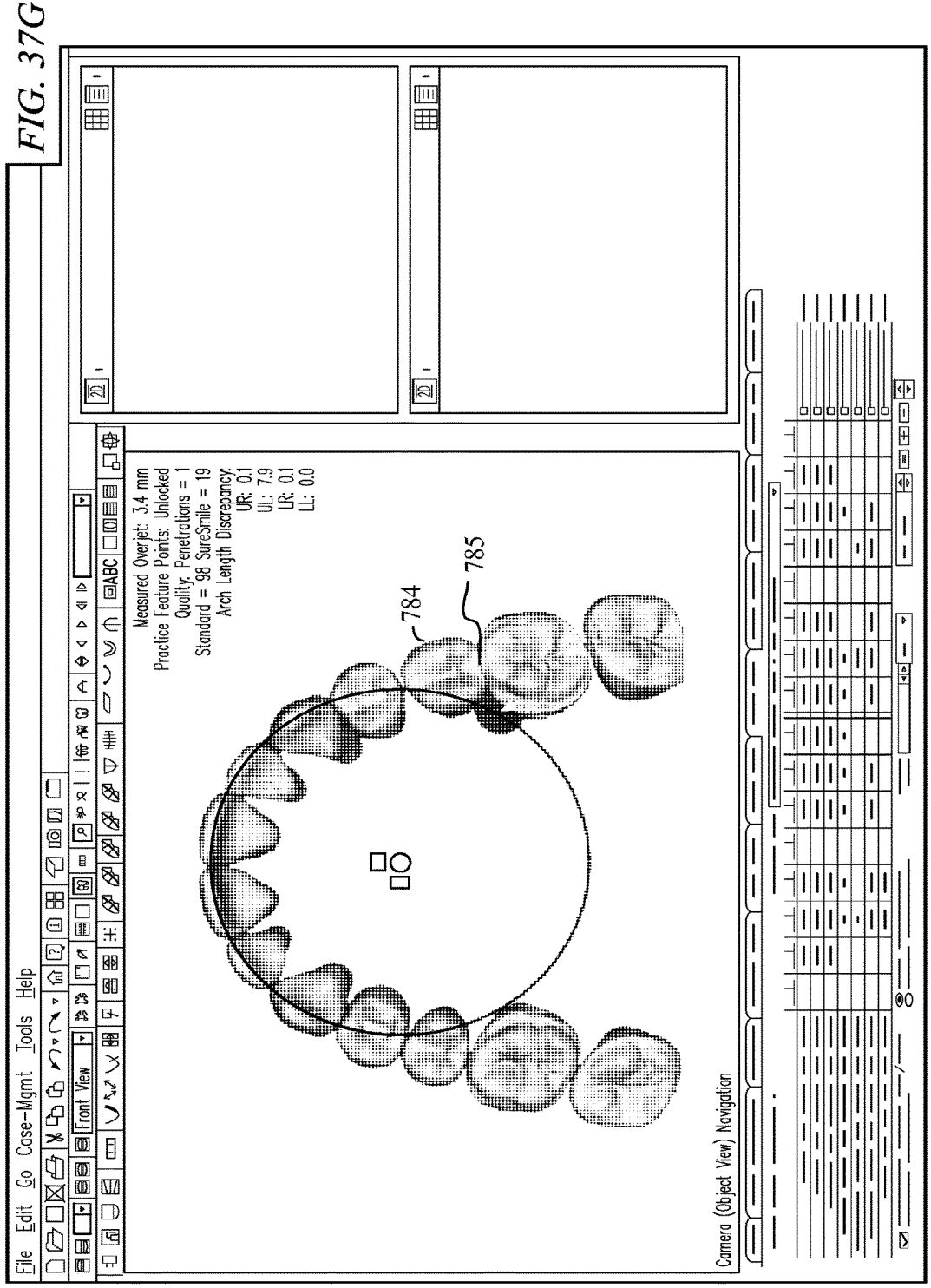
FIG. 37G shows tooth has been automatically selected to fill space. Note that it is over contoured.
Figure 37H:
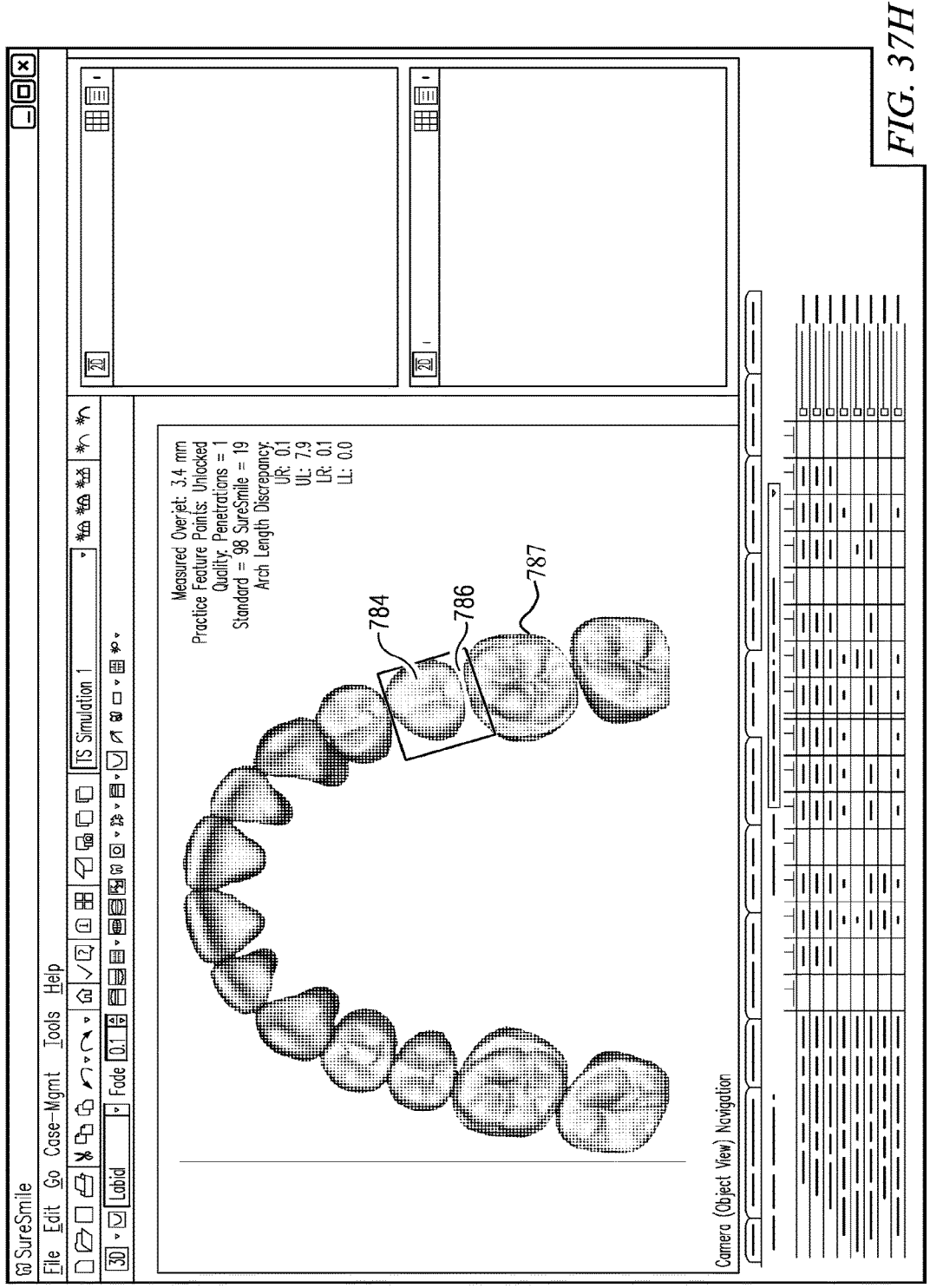
FIG. 37H shows that the tooth form has been shaped to look more appropriate. Note that there is a little space left. This can be closed orthodontically by moving the molar forward.
Figure 37I:
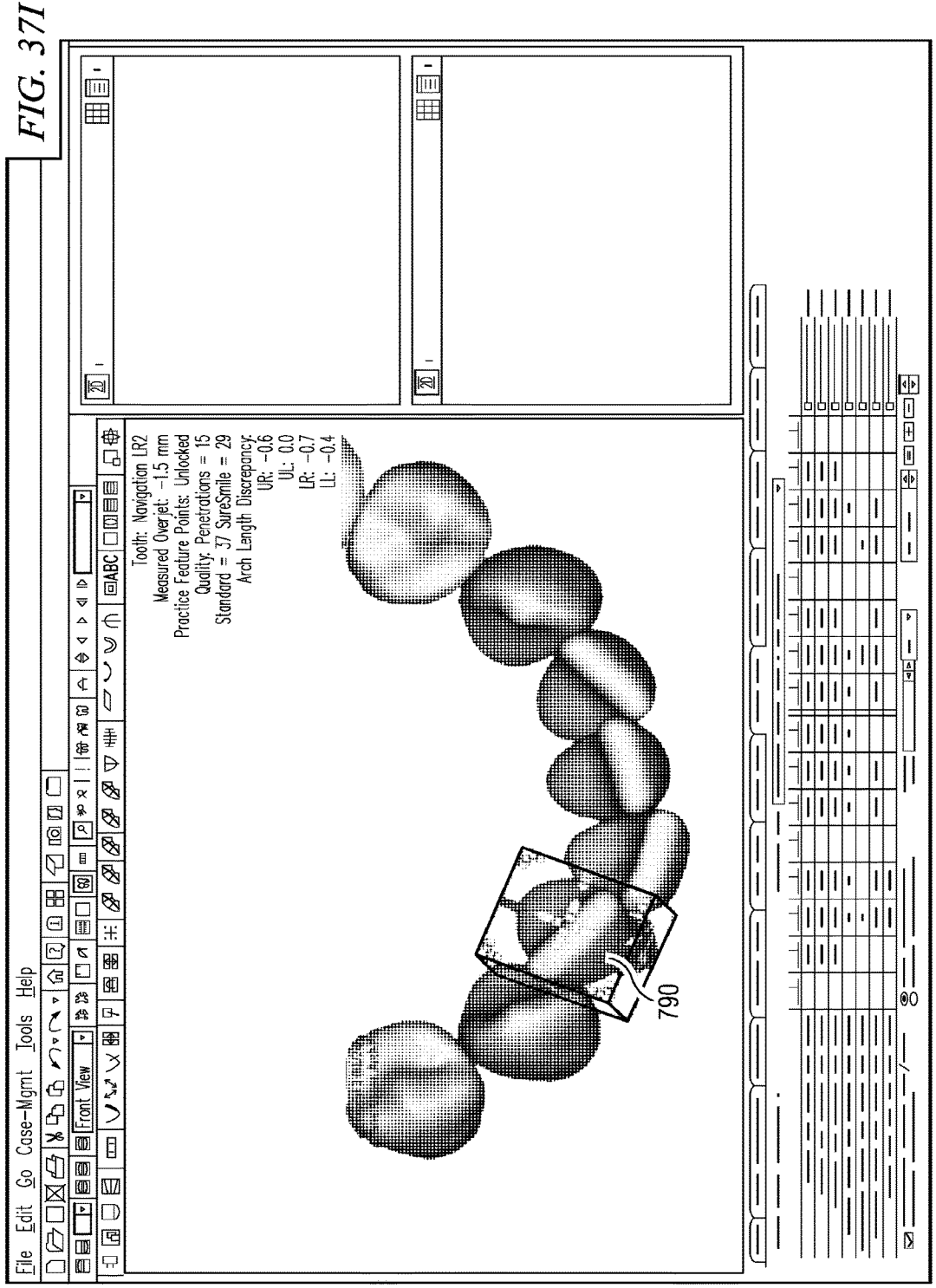
FIG. 37I shows that the patient has crowding. Efficient resolution of the crowding is planned by optimizing tooth movement and restoration with veneers.
Figure 37J:
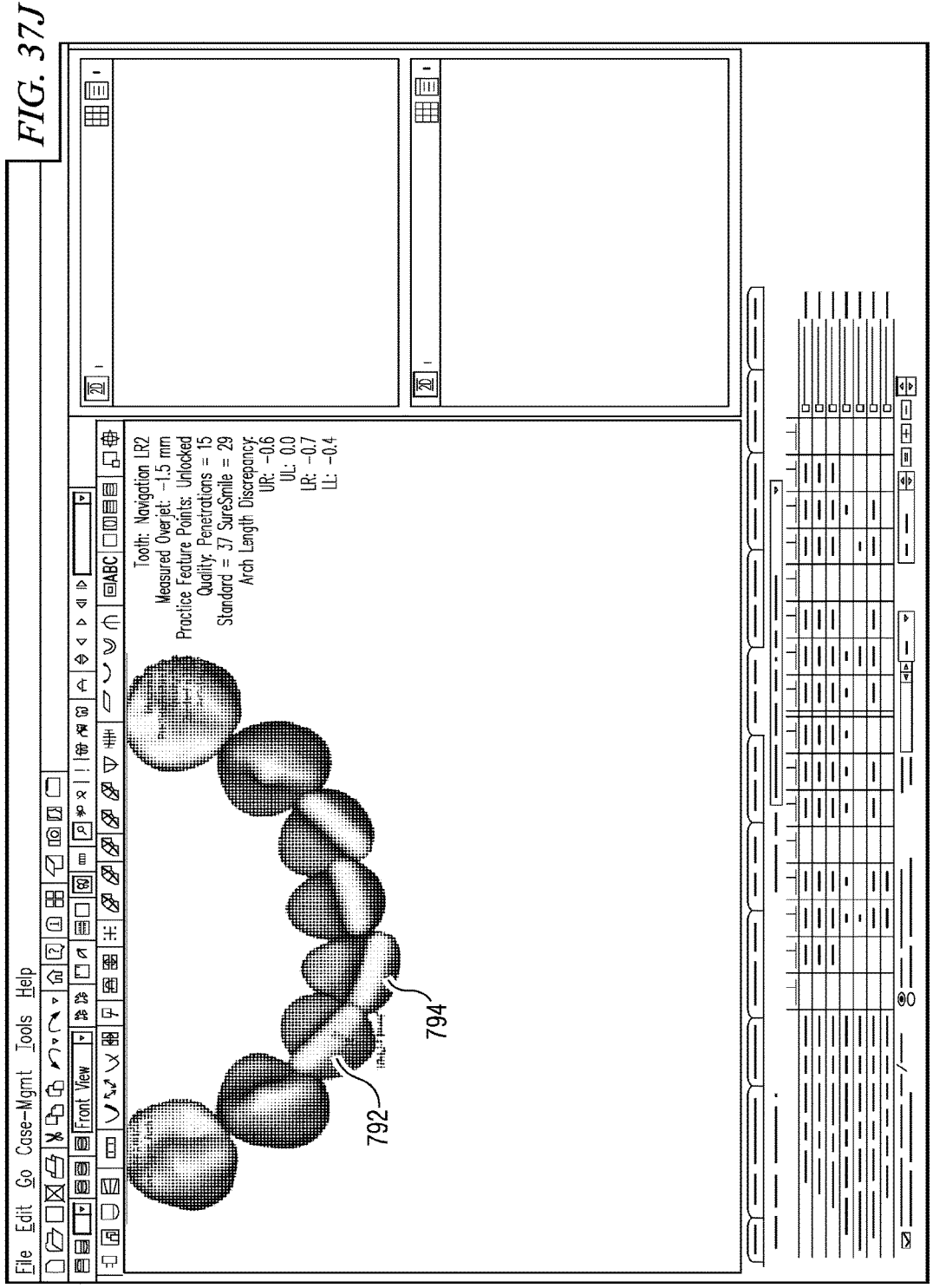
FIG. 37J shows that the teeth have been moved orthodontically to help resolve some of the crowding.
Figure 37K:
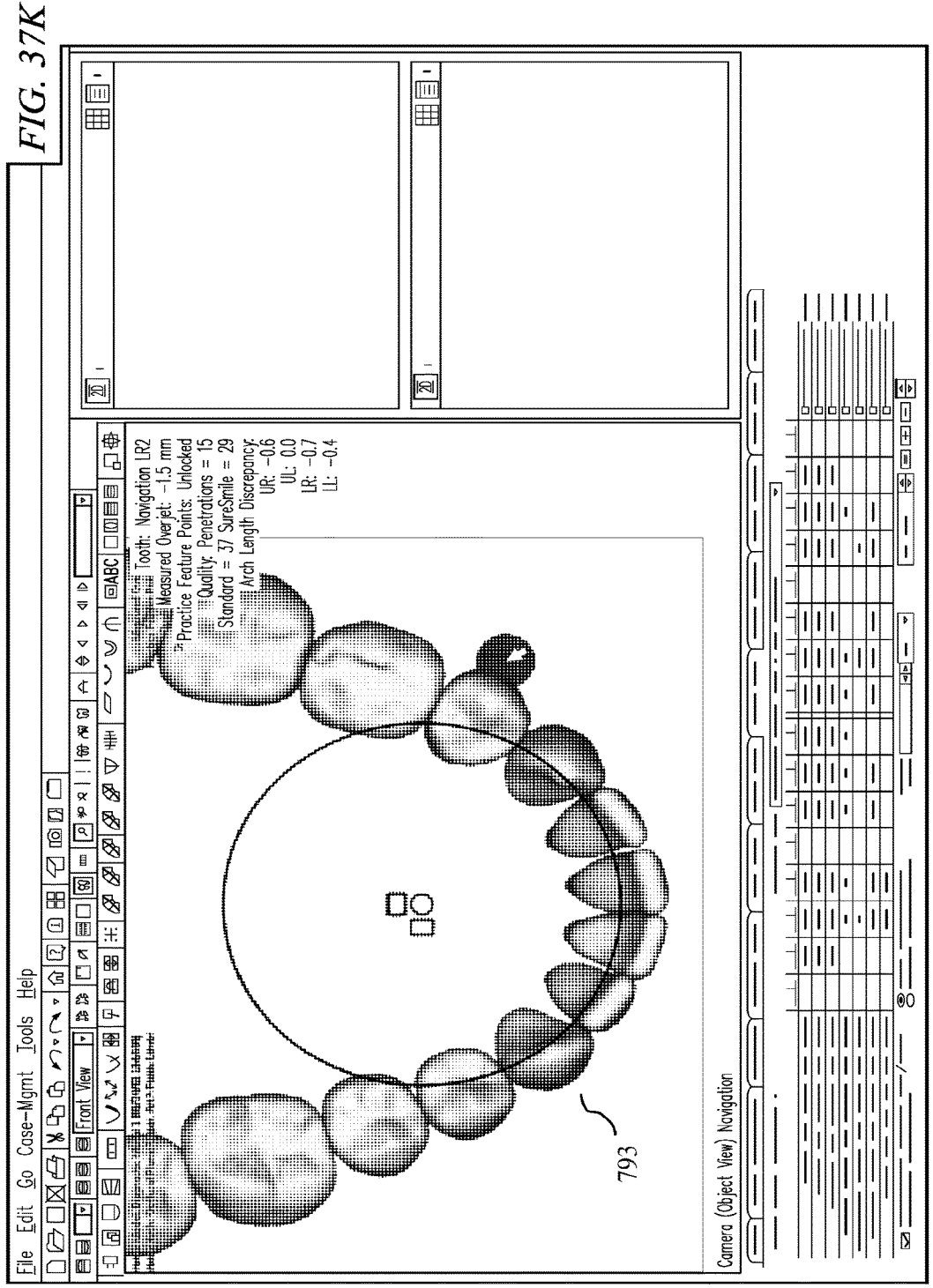
FIG. 37K shows that all teeth have been moved orthodontically to help resolve some of the crowding.
Figure 37M:
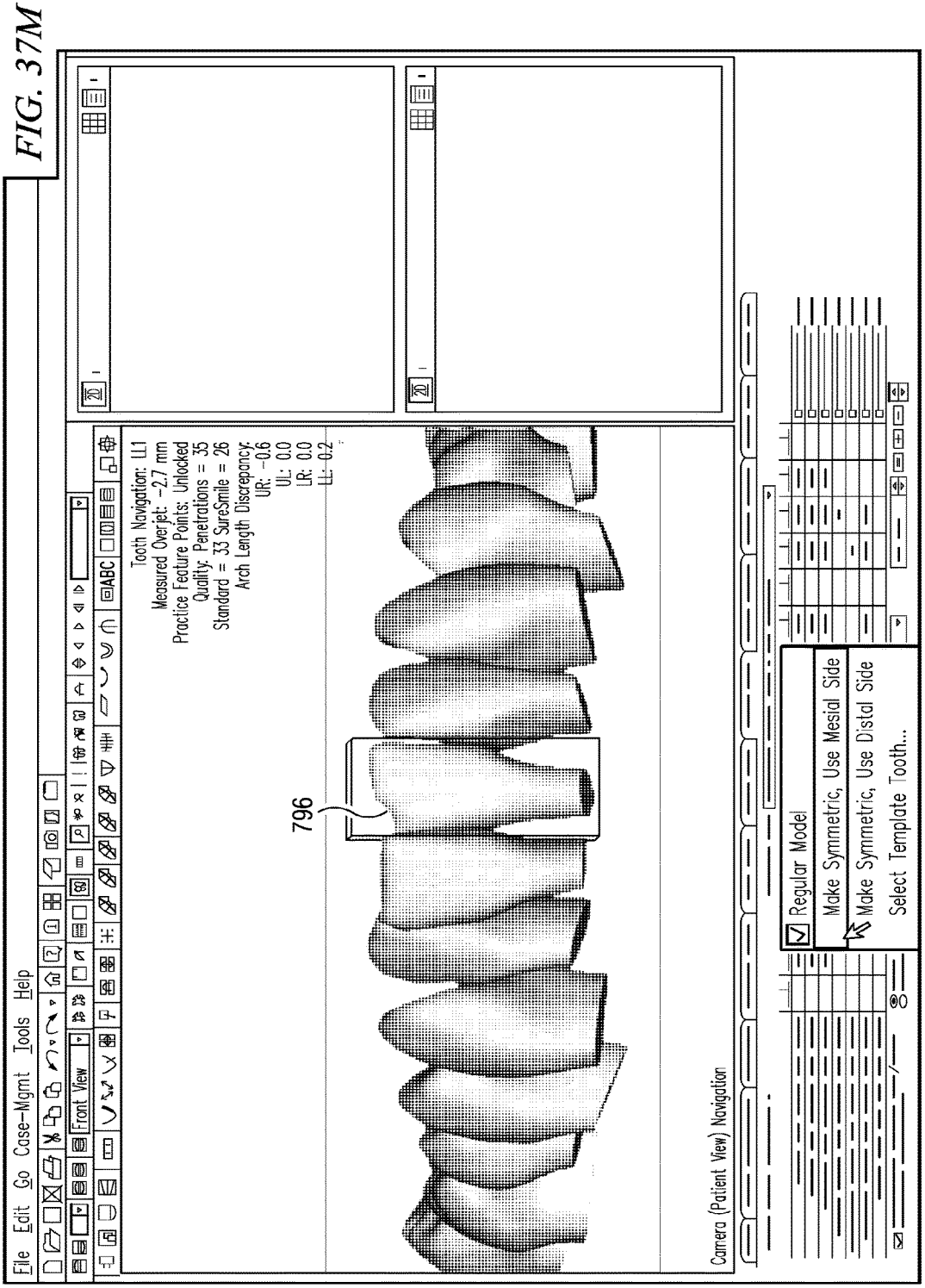
FIG. 37M shows fractured incisal edge. Choice of either restoring the fracture by using a template tooth, or a similar non-fractured tooth, or choosing either the mesial or distal side of any normal shaped tooth to restore edges or line angles.
Figure 37N:
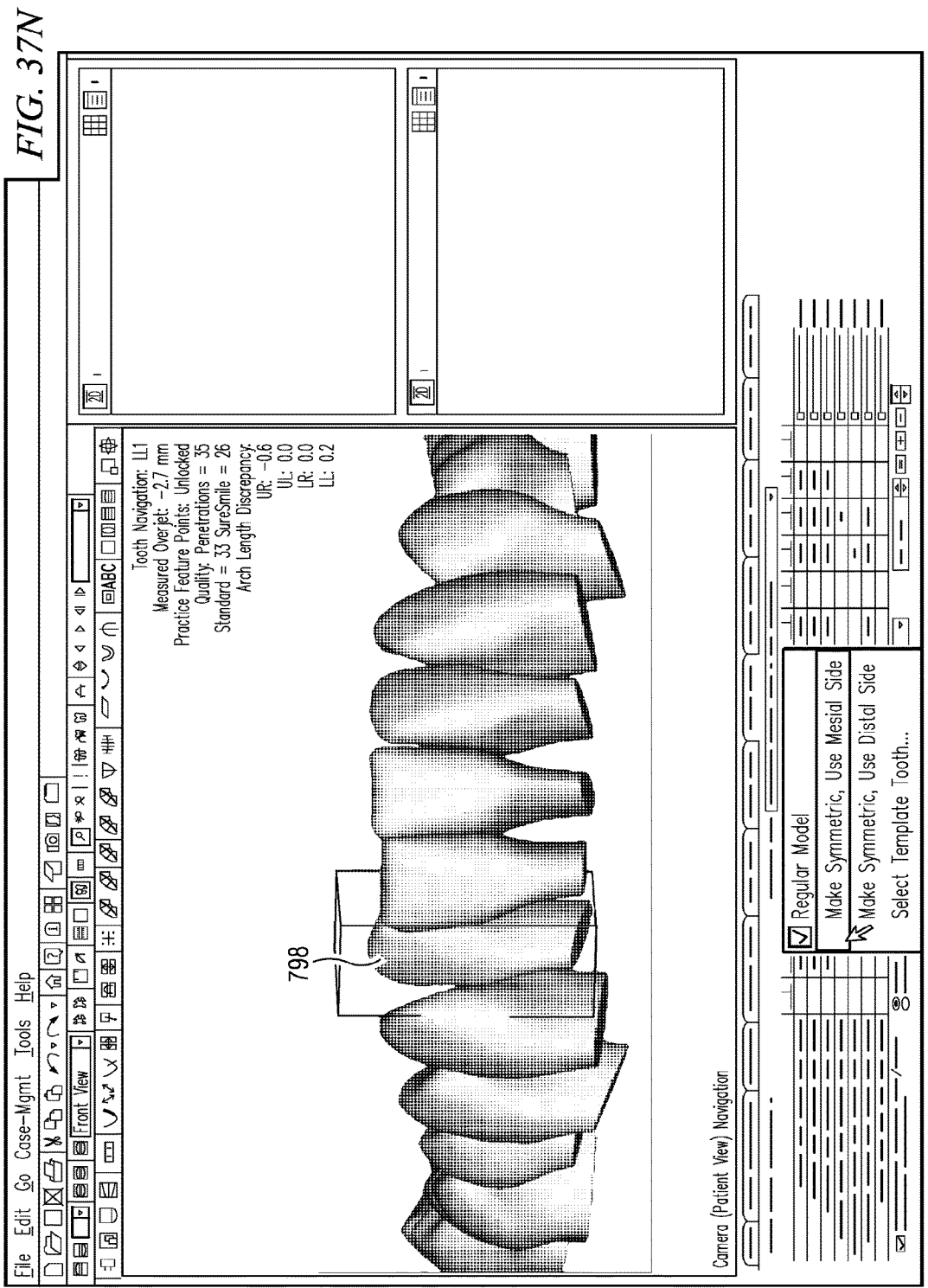

FIGS. 37A-37N show planning of tooth shape and form and restorations with and without orthodontic treatment to achieve maximum esthatics as efficiently as possible.

FIG. 37A shows both a 2-D view 760 and a 3-D view 762 of the mal-formed tooth, and the space on either side of the mal-formed tooth. This space can be closed orthodontically or the shape or the shape and form of the tooth can be restored.

FIG. 37B shows planning to close the space on either side by restoring the tooth 770 on either side by 1 mm.

FIG. 37C shows that one side 774 of the tooth has been restored to close the space and achieve normal tooth form.

FIG. 37D shows that both sides 776 and 778 of the tooth have been restored to close the space and achieve normal tooth form.

FIG. 37E shows missing second bicuspid tooth 780.

FIG. 37F shows dialogue box to—781—select appropriate tooth from the dentition 782 to close space.

FIG. 37G shows tooth 784 has been automatically selected to fill space. Note that it is over contoured 785.

FIG. 37H shows that the tooth 784 form has been shaped to look more appropriate. Note that there is a little space 786 left. This can be closed orthodontically by moving the molar 787 forward.

FIG. 37I shows that the patient has crowding 790. Efficient resolution of the crowding is planned by optimizing tooth movement and restoration with veneers.

FIG. 37J shows that the teeth 792 and 794 have been moved orthodontically to help resolve some of the crowding.

FIG. 37K shows that all teeth 793 have been moved orthodontically to help resolve some of the crowding.

FIG. 37L shows the selection of automatic veneer build up 795 to resolve the crowding completely and to provide better shape and form. 3-D simulation planning has allowed the optimal planning of care from both restorative and orthodontic perspectives with minimal tooth movement and destruction of tooth.

FIG. 37M shows fractured incisal edge 796. Choice of either restoring the fracture by using a template tooth, or a similar non-fractured tooth, or choosing either the mesial or distal side of any normal shaped tooth to restore edges or line angles.

FIG. 37N shows fractured incisal edge restored in normal shape and form 798.

Figure 38A:
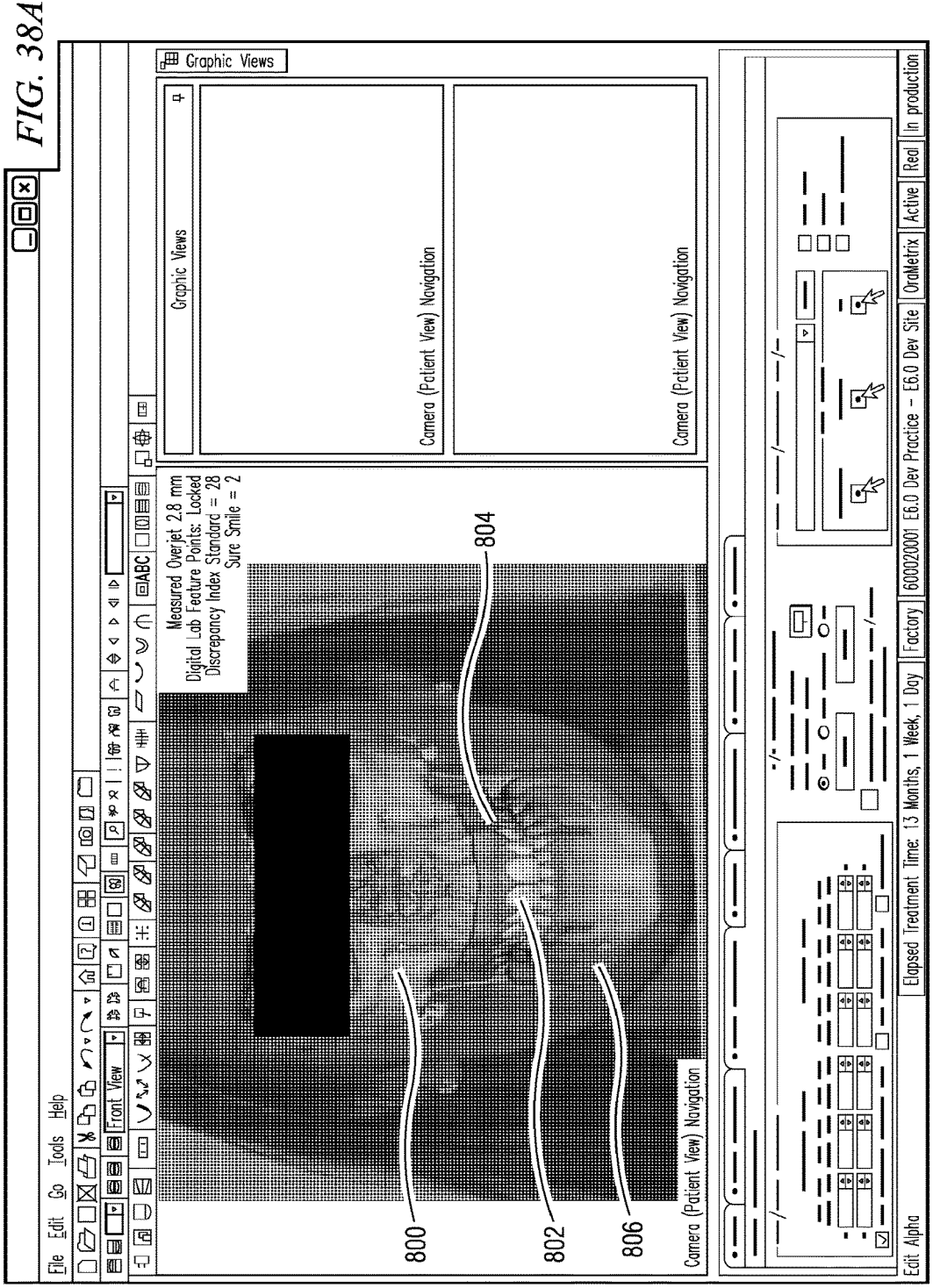
FIG. 38A shows composite image of craniofacial complex by combining craniofacial bones, tooth crown and roots from CBCT, gingival tissue from surface scanning, and facial soft tissue from 2-D photographs and tooth with roots; and the lower jaw and its teeth registered to the upper jaw and teeth using an intraoral bite registration scan.

FIG. 38A shows composite image of craniofacial complex by combining craniofacial bones 800, tooth crown and roots 802 from CBCT, gingival tissue 804 from surface scanning, and facial soft tissue 806 from 2-D photographs and tooth with roots; and the lower jaw and its teeth registered to the upper jaw and teeth using an intraoral bite registration scan.

Figure 38B:
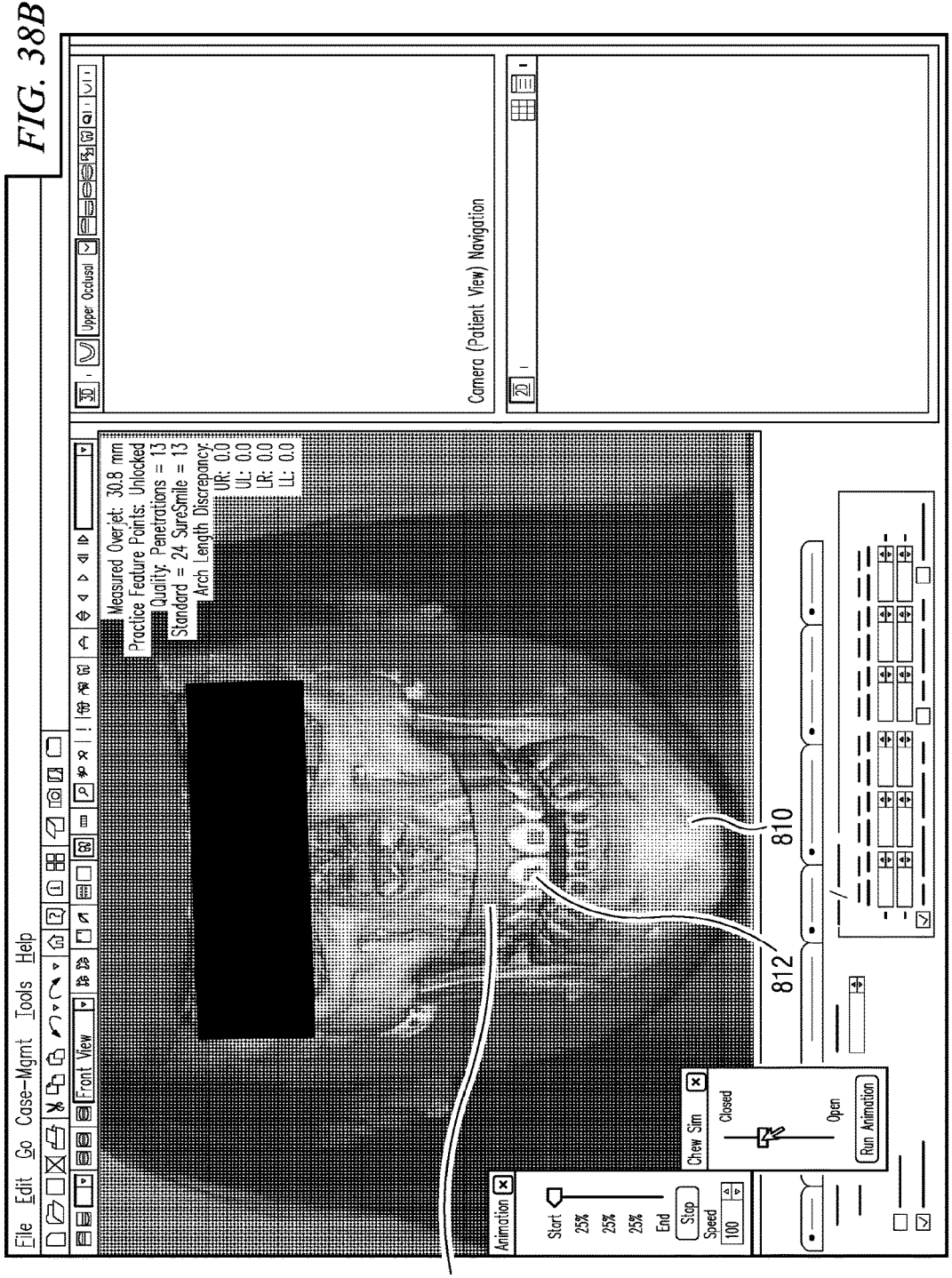
FIG. 38B shows composite image of craniofacial complex by combining craniofacial bones, tooth crown and roots from CBCT, gingival tissue from surface scanning, and facial soft tissue from 2-D photographs and tooth with roots; and the lower jaw and its teeth registered to the upper jaw and teeth using an intraoral bite registration scan. The figure also shows functional movements such as mouth opening.

FIG. 38B shows composite image of craniofacial complex by combining craniofacial bones 810, tooth crown 812 and roots from CBCT, gingival tissue 814 from surface scanning, and facial soft tissue from 2-D photographs and tooth with roots; and the lower jaw and its teeth registered to the upper jaw and teeth using an intraoral bite registration scan. The figure also shows functional movements such as mouth opening.

FIG. 38C shows volumetric 3-D image of teeth and gingival tissue 814 in relation to the patient's face in order to assess and plan for aesthetics.

Figure 39A:
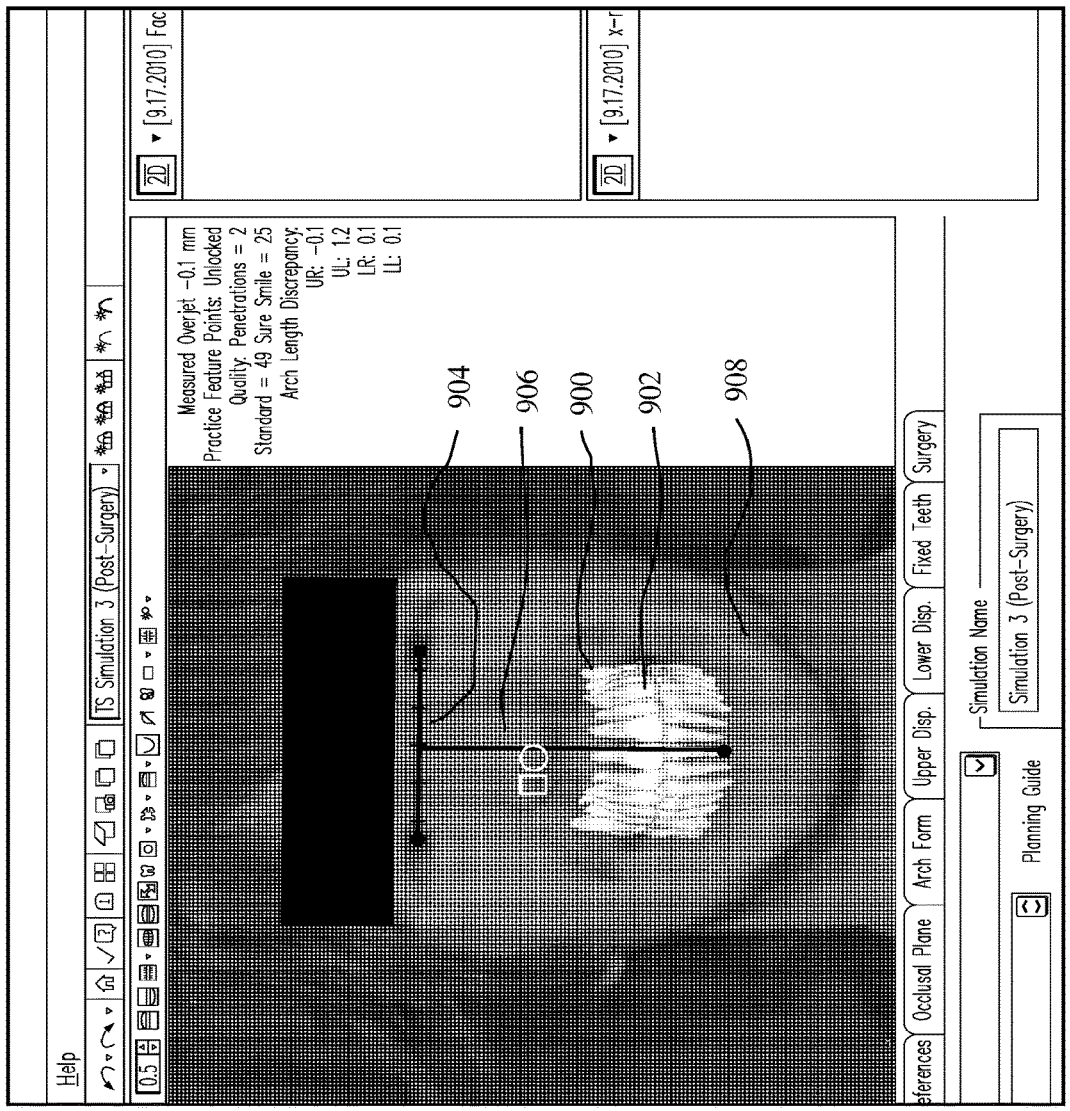
FIG. 39A shows the dental complex comprising the roots and the crowns, which can be oriented to user defined reference planes. For example reference from the frontal perspective has been defined by a line between the pupils of the eyes and perpendicular to this line. Similarly, user defined reference plane. A second reference plane has been chosen from the lateral perspective. The combination of frontal reference plane and lateral reference plane, with a common coordinate system with respect to the model and the face allows for correct orientation in 3-D space. The face and its accompanying structures can also be oriented by the user from any perspective including frontal and lateral.

FIG. 39A shows the dental complex comprising the roots—900—and the crowns 902, which can be oriented to user defined reference planes. For example reference from the frontal perspective has been defined by a line 904 between the pupils of the eyes and a line 906 perpendicular to this line 904. Similarly, user defined reference plane. A second reference plane (not shown) has been chosen from the lateral perspective. The combination of frontal reference plane and lateral reference plane, with a common coordinate system with respect to the model and the face allows for correct orientation in 3-D space. The face and its accompanying structures 908 can also be oriented by the user from any perspective including frontal and lateral.

Figure 39B:
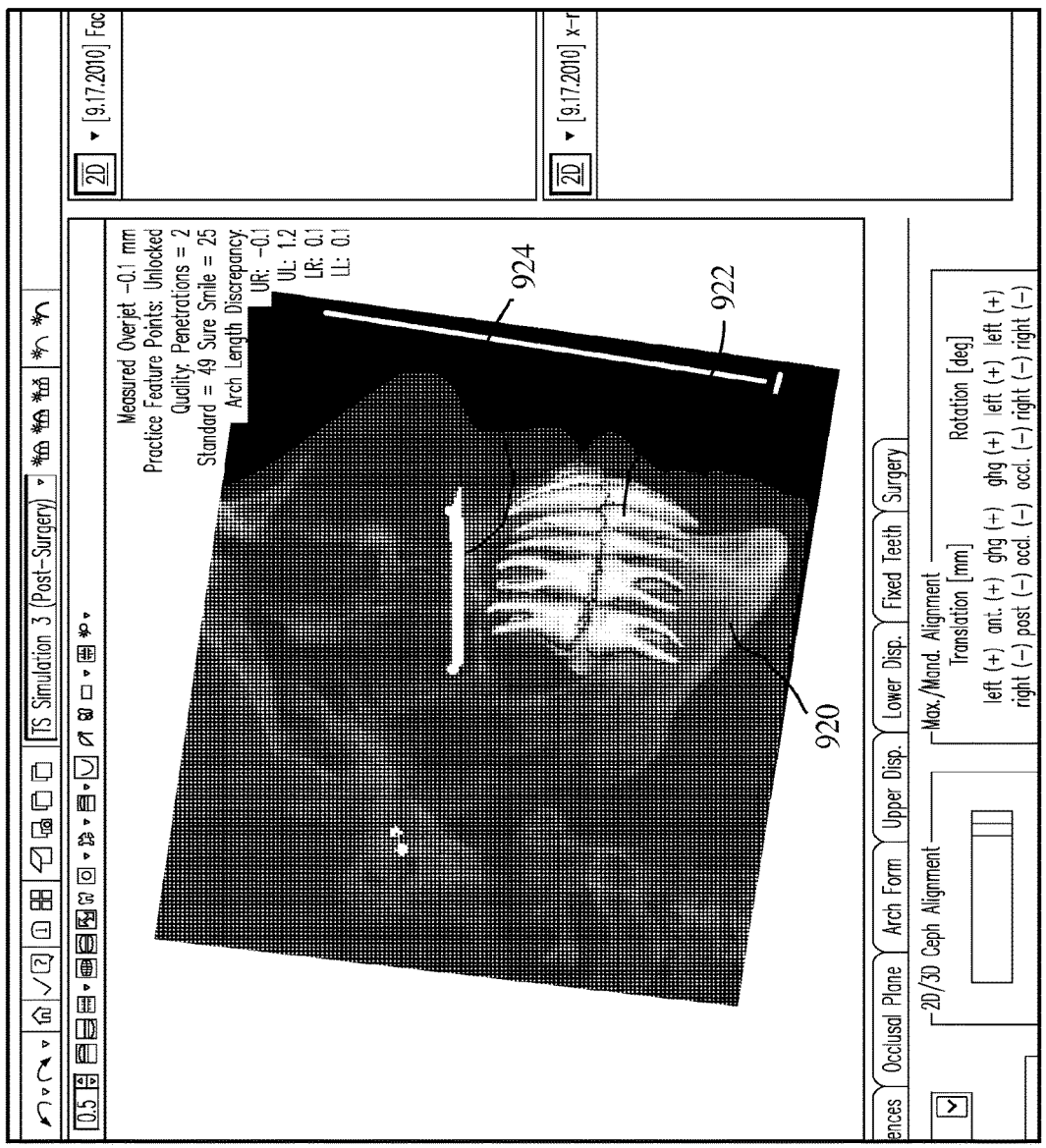
FIG. 39B shows a side view of the dental complex showing bones, teeth and a reference plane.

FIG. 39B shows a side view of the dental complex showing bones 920, teeth 922 and a reference plane 924.

Figure 39C:
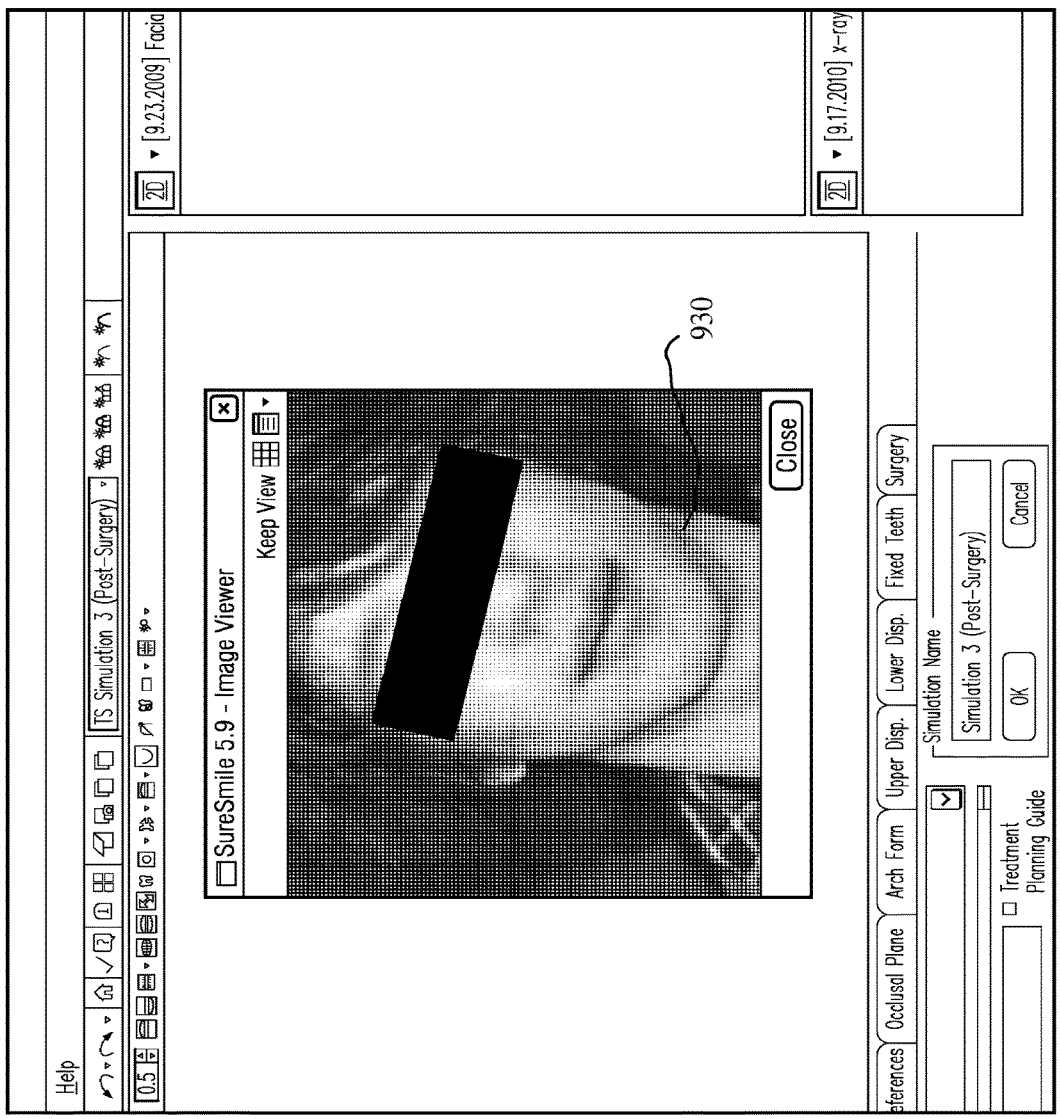
FIG. 39C shows different orientations of the face of the patient.

FIG. 39C shows different orientations of the face 930 of the patient.

The preferred embodiment of the invention combines volume scan data with surface scan data to get the benefit of both and compensate for weaknesses of each.

The advantages of volume scan data are (i). acquisition of invisible data (CBCT & MRI) such as (a) roots, bone, condile, Airways; whereas the advantages of the surface scan data are high accuracy and resolution on visible surfaces.

The goal of the invention is to obtain (a.) high accuracy representation of visible areas, especially small features on teeth, (b) representation of gingival, (c) representation of tooth roots, (d) representation of bones, (e) representation of condole, and (f) representation of brackets, all in very high precision 3-D modeling by combining surface scan data with the volume scan data.

In summary, method and workstation for generating three dimensional digital or virtual model of the dentition and surrounding anatomy of a patient from surface scan data and volume scan data are disclosed. Surface scans of a patient's dentition are obtained using in-vivo scanning or other types of scanning such as scanning an impression of the patient's dentition or scanning a physical model of the patient's dentition. Volume scan data of the patient's dentition are obtained using Cone Beam Computed Tomography (CBCT) or Magnetic Resonance Tomography (MRI) imaging equipment. By registering the surface scan data with the volume scan data three dimensional models of a patient's dentition and surrounding anatomy including roots, bones, soft tissues, airways, etc. are obtained.

First and foremost the essence of the patent is the ability to capture images from various CBCT, cat, MRI, ultrasound, still photos, intraoral scanners and videos both static and dynamic.

With these images a composite structure of the face can be constructed dynamic or static One can also track function or jaw movement and simulate the functional movements e.g., smile movement of the lower jaw, etc.

Most importantly from the CBCT one can extract root and bone data and soft tissue data and if there is any attached appliance such as orthodontic brackets, without taking multiple images in one sweep, and process each component to create separate objects to use for treatment planning and customized appliance selection or design and manufacture The simulations allow one to reposition any component bone soft tissue tooth with roots with respect to each other in a measured way and chosen reference planes. Furthermore one can change and restore both the shape and form of any of the structures to modify the appearance of any of these structures e.g., tooth shape or gum tissue, etc. These changes both in terms of position and shape can be driven by external data, e.g., templates or normative data or internal data the non-affected side of the patient or combination thereof.

One can also replace or remove any of the structures to achieve the desired goal, e.g., implants or extraction.

In essence, one can reposition restore replace or remove any of the said objects. The codependency of movement of one object and its effect on another can also be simulated for all three tissue types, e.g., when the tooth moves how does it affect the gum soft tissue when the tooth moves where does the root move in reference to the bone or how does the bone change how does the face change when the bones move. As a result all types of planning can be executed in by various professions in an interactive manner asynchronously or synchronously these may include the orthodontist, maxillofavcial surgeon, prosthodontist, perodontist, restorative dentist. Also function can be simulated or modeled based upon captured data to achieve the desired goals, e.g., the teeth with their roots can be appropriately positioned in the bone to withstand the stresses of jaw movement or that the position of the jaw joint i.e., the condyle is in harmony with the position of the teeth to prevent any source of dysfunction all these simulation involve natural anatomical structures being affected in 3d space with volumetric data or in combination with 2d data when appropriate The treatment plan can be used to generate any kind of dental orthodontic restorative prosthodontic or surgical device may it tissue borne dental borne or osseous borne or any combination singularly in serial or in parallel some devices e.g., brackets, indirect bonding trays, stents, fixation plates, screws, implants, surgical splints, crowns, implants, prosthetic devices, dentures, or prosthetic parts to replace or restore any tissue. Manufacture can be done by stereolithography milling or build up processes. Furthermore this data can be used to drive navigational systems for performing any procedure and simulations can be used to train and build skills or examine proficiency another example the output can be used to drive robots to perform procedures. Lastly the treatment plan can be printed to provide a solid model representation.

Registration can be made at three levels. One is the orientation of the face, secondly the orientation of any component soft tissue to teeth or bone by using appropriate reference planes that are user defined or anatomically defined, and finally the bite registration by taking the intramural scan and registering the CBCT to it or a scan of the bite registration material, e.g., wax and registering to it.

A model of the dentition is not fused into the crank facial structure—it is captured all at once and then one can extract/segregate individual features for treatment planning.

The optimization of the treatment plan can be accomplished by using different approaches, e.g., correcting crowding by minimizing tooth movement and planning veneers or minimizing tooth preparation for veneer construction by positioning the teeth appropriately. This can be said for any structure and the decision can be driven by the patients need, time constraints, cost risk benefit, skill of operator, etc.

The process to extract roots based on well-known concepts is as follows:

1. Interactively, select a good threshold value which captures the roots
2. Extract the surface or surfaces identified in step 1, representing them as triangles
3. Interactively, apply any needed clean up—remove unwanted data and merge any needed, disconnected fragments
4. Interactively, separate the data (triangles) into separate, individual tooth objects
5. Interactively, apply any needed clean up to each tooth object The bone surface can be extracted similarly, as follows:
1. Interactively, select a good threshold value which captures the mandible, maxilla, and potentially, the teeth
2. Extract the surface or surfaces identified in step 1, representing them as triangles
3. Interactively, apply any needed clean up—remove unwanted data and merge any needed, disconnected fragments
4. Using boolean (set) operators, subtract the tooth objects from the extracted surfaces
5. Interactively, separate the mandible from the maxilla by removing any edges and triangles which connect one to the other.

This process can be executed in any of various available tools that can read a CBCT data set (DICOM) and find an iso-surface based on a threshold value. One such software tool is Amira.

While presently preferred embodiments of the invention have been described for purposes of illustration of the best mode contemplated by the inventors for practicing the invention, wide variation from the details described herein is foreseen without departure from the spirit and scope of the invention. This true spirit and scope is to be determined by reference to the appended claims. The term "bend", as used in the claims, is interpreted to mean either a simple translation movement of the work-piece in one direction or a twist (rotation) of the work-piece, unless the context clearly indicates otherwise.

We claim:

1. A method of registering an upper arch and a lower arch of a patient, with accompanying teeth with or without roots, with respect to jaw bones or facial tissue structure, comprising the steps of:
   capturing a three dimensional volumetric scan of a craniofacial complex and a dentofacial complex of the patient;
   defining reference planes; and
   registering (1) the three dimensional volumetric scan of the dentofacial complex with accompanying roots and (2) the patient's facial structure to the defined reference planes.

2. The method of claim 1, wherein the three dimensional volumetric scan data includes crowns and roots of the teeth, bone, soft tissue, and appliances attached to any of these structures.

3. The method of claim 1, wherein one of the defined reference planes is defined from a frontal perspective.

4. The method of claim 1, wherein one of the defined reference planes is defined from a lateral perspective.

5. A method of registering an upper arch and a lower arch of a patient, with crowns accompanying teeth without roots, with respect to 2D images or 3-D images of jaw bones or facial tissue structure, comprising the steps of:
   capturing a three dimensional volumetric scan of a craniofacial complex and a dentofacial complex of the patient;
   capturing surface data of a dentition of the patient;
   capturing one or more 2D photographic images of the facial structure of the patient;
   defining reference planes; and
   registering the surface data of the dentition with respect to (1) the patient's jaw bones, and/or facial structure from the three dimensional volumetric scan, (2) the facial structure in the one or more 2D photographic images and (3) the defined reference planes.

6. The method of claim 5, wherein the three dimensional volumetric scan data includes crowns and roots of the teeth, bone, soft tissue, and appliances attached to any of these structures.

7. The method of claim 5, wherein one of the defined reference planes is defined from a frontal perspective.

8. The method of claim 5, wherein one of the defined reference planes is defined from a lateral perspective.

* * * * *